US006971391B1

(12) United States Patent
Wang et al.

(10) Patent No.: US 6,971,391 B1
(45) Date of Patent: Dec. 6, 2005

(54) PROTECTIVE ASSEMBLY

(75) Inventors: Xingwu Wang, Wellsville, NY (US); Howard J. Greenwald, Rochester, NY (US); Jeffrey L. Helfer, Webster, NY (US); Robert W. Gray, Rochester, NY (US)

(73) Assignee: Nanoset, LLC, East Rochester, NY (US)

( * ) Notice: Subject to any disclaimer, the term of this patent is extended or adjusted under 35 U.S.C. 154(b) by 357 days.

(21) Appl. No.: 10/373,377

(22) Filed: Feb. 24, 2003

Related U.S. Application Data

(63) Continuation-in-part of application No. 10/324,773, filed on Dec. 18, 2002, now Pat. No. 6,864,418.

(51) Int. Cl.[7] .............................................. A61F 13/00

(52) U.S. Cl. ........................ 128/846; 607/96; 607/115; 607/116; 607/9; 606/27; 606/32; 601/3; 600/410

(58) Field of Search .................. 128/846; 607/96–156, 607/2–38, 63–64; 606/27–52; 601/2–5; 600/407, 600/410–423

(56) References Cited

U.S. PATENT DOCUMENTS

| 4,320,763 | A | * | 3/1982 | Money ........................... 607/9 |
| 4,745,923 | A | * | 5/1988 | Winstrom ....................... 607/9 |
| 5,433,732 | A | * | 7/1995 | Hirschberg et al. ............. 607/7 |
| 5,591,218 | A | * | 1/1997 | Jacobson ...................... 607/63 |
| 5,833,710 | A | * | 11/1998 | Jacobson ....................... 607/4 |
| 5,968,083 | A | * | 10/1999 | Ciciarelli et al. .............. 607/2 |
| 6,161,040 | A | * | 12/2000 | Blunsden ....................... 607/5 |

* cited by examiner

*Primary Examiner*—Fadi H. Dahbour
(74) *Attorney, Agent, or Firm*—Howard J. Greenwald

(57) ABSTRACT

An assembly for protecting biological tissue from the effects of heating. The assembly contains a conductor in contact with the biological tissue and forming an electrical circuit comprising the biological tissue. The assembly contains a device for modifying the impedance of the electrical circuit such that, at a frequency of from about 10 megahertz to about 150 megahertz, such impedance is at least about 0.5 ohms per centimeter of length of said conductor. The assembly also contains a device for limiting the flow of current through the biological tissue such that, when the assembly is exposed to an alternating current electromagnetic field at a frequency of 64 megahertz and a magnetic field strength of 1.5 Tesla for 15 minutes, the temperature of the biological tissue does not exceed 42 degrees Celsius.

45 Claims, 16 Drawing Sheets

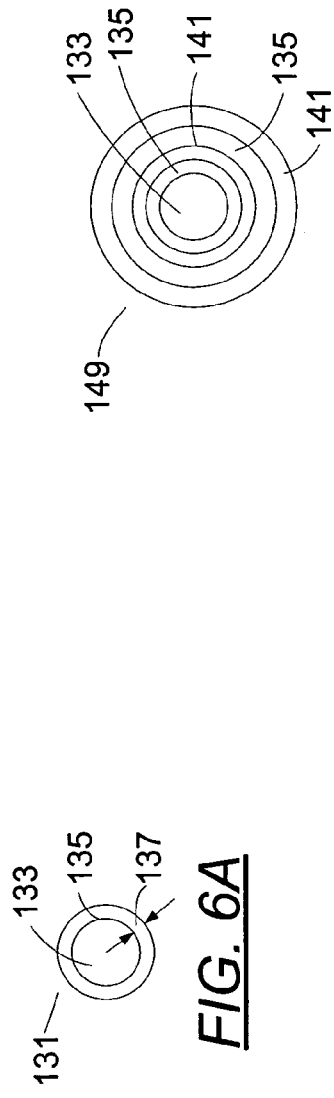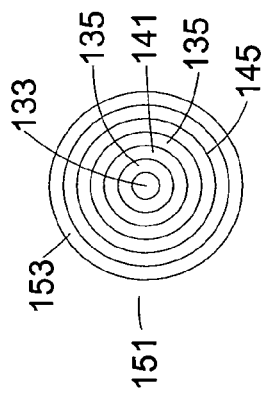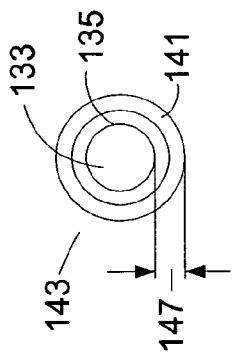

PROTECTIVE ASSEMBLY

CROSS-REFERENCE TO RELATED PATENT APPLICATION

This patent application is a continuation-in-part of applicants' patent application U.S. Ser. No. 10/324,773, filed on Dec. 18, 2002 now U.S. Pat. No. 6,864,418.

FIELD OF THE INVENTION

An assembly for protecting biological tissue from the effects of heating comprising a conductor in contact with such biological tissue and forming an electrical circuit comprising such biological tissue, wherein such assembly is comprised of means for modifying the impedance of the electrical circuit such that, at a frequency of from about 10 megahertz to about 150 megahertz, such impedance is at least about 0.5 ohms per centimeter of length of said conductor, and wherein said assembly is comprised of means for limiting the flow of current through said biological tissue such that, when said assembly is exposed to an alternating electromagnetic field at a frequency of 64 megahertz and a direct current magnetic field strength of 1.5 Tesla for 15 minutes, the temperature of said biological tissue does not exceed 42 degrees Celsius.

BACKGROUND OF THE INVENTION

U.S. Pat. No. 5,217,010 discloses a device for monitoring a patient which can operate safely in an MRI system. At columns 1 and 2 of this patent, it is disclosed that: "Until now, however, there has been a reluctance to place patients with pacemakers in an MRI apparatus . . . . The RF field produced in the MRI system represents a form of electromagnetic interference (EMI) that is very harzardous to the pacemaker. The RF pulses can produce two distinct categories of problems: 1) heating, and 2) voltage generation in the pacemaker . . . . " The entire disclosure of this United States patent is hereby incorporated by reference into this specification.

Many other United States patents have described processes and/or devices for mitigating the effects of high current in and/or near biological tissue.

Thus, for example, U.S. Pat. No. 4,320,763 discloses a device for preventing tissue damage when high-currents flow through the tissue as a result of high voltage differentials. The patent has, as one of its objects, " . . . to protect the heart tissue of a pacemaker implantee from damage upon application of high voltages to the users body."

By way of further illustration, U.S. Pat. No. 4,440,174 has, as one of its objects, " . . . to provide a protection device that protects both a pacemaker or other implantable device and the heart tissue near a lead thereof against damage from high current and voltage levels . . . . "

U.S. Pat. No. 4,745,923 describes and claims: "An apparatus for protecting an implantable electrical device having a plurality of electrically conductive terminals . . . . " The patent discloses that " . . . in the past, a number of attempts have been made to provide adequate protection against excessive currents and voltages for pacemakers and other medical devices such as electrocardiogram (ECG) amplifiers. For example, it is known to connect one or more zener diodes between the opposite leads of a pacemaker to limit the voltage differential therebetween . . . . However . . . this approach is not effective to limit the current flow between the heart tissue and the electrode at the distal end of the pacemaker lead. As a result, the heart tissue near the point of contact with the electrode can be severely damaged when high-voltage defibrillation pulses are applied to the heart." U.S. Pat. No. 4,320,763 also discloses that such tissue damage can be prevented by connecting a current limiting device such as a diode or a pair of field effect transistors (FETs) in series between a pacemaker output terminal and a distal electrode.

By way of yet further illustration, U.S. Pat. No. 5,833,710 provides a device for protecting cardiac tissue near low energy implanted electrodes. As is disclosed in column 3 of this patent, " . . . the present invention pertains to protecting the circuitry connected to the low energy leads, and protecting the patient's tissue at the low energy lead sites, from the high energy pulses . . . and from high energy pulses from other medical electronic devices . . . . "

U.S. Pat. No. 5,591,218 describes a "current limiter for implantable electronic device lead" which, like the device of U.S. Pat. No. 5,833,710, " . . . protects cardiac tissue near the low energy electrodes" (see the abstract).

U.S. Pat. No. 6,161,040 discloses, at column 1 thereof, that " . . . because the impedance of the heart tissues through which the shocks are discharged are unknown, it is difficult to control the current delivered through the shocks. Abnormally high current levels are undesirable because a high current may damage the heart tissues."

Applicants' U.S. Pat. No. 6,502,972 describes and claims a magnetically shielded conductor assembly comprised of a first conductor disposed within an insulating matrix, and a layer comprised of nanomagnetic material disposed around said first conductor, provided that such nanomagnetic material is not contiguous with said first conductor. In this assembly, the first conductor has a resistivity at 20 degrees Centigrade of from about 1 to about 100 micro ohm-centimeters, the insulating matrix is comprised of nano-sized particles wherein at least about 90 weight percent of said particles have a maximum dimension of from about 10 to about 100 nanometers, the insulating matrix has a resistivity of from about 1,000,000,000 to about 10,000,000,000,000 ohm-centimeter, the nanomagnetic material has an average particle size of less than about 100 nanometers, the layer of nanomagnetic material has a saturation magnetization of from about 200 to about 26,000 Gauss and a thickness of less than about 2 microns, and the magnetically shielded conductor assembly is flexible, having a bend radius of less than 2 centimeters.

The entire disclosure of each of U.S. Pat. Nos. 5,217,010, 4,320,763, 4,440,174, 5,745,923, 5,833,710, 5,591,218, 6,161,040, and 6,502,972 is hereby incorporated by reference into this specification. In spite of their disclosures, and the disclosures of many comparable United States and foreign patents, it does not appear that anyone has yet come up with a satisfactory solution to the problem of heat-induced tissue damage that occurs during MRI imaging processes.

Thus, e.g., in a publication by S. Achenbach et al. ("Effects of MRI on Cardiac Pacing and Electrodes," American Heart Journal, 1997, 134, 467–473), experimental studies were presented that showed that pacemaker electrodes could heat up to 100 degrees Centigrade within 90 seconds of magnetic resonance imaging (MRI) canning.

Thus, e.g., in an article by M. Konings et al., of the Department of Radiology of University Hospital, Utrecht, The Netherlands (see Medica Mundi, 45/1, March 2001, page 35), it was disclosed that " . . . it is not possible to design a device for use in an MR environment incorporating long metallic parts such as guide wires, mechanical cables, or electrical leads, and be completely sure of safety. The safe length of any metallic part used within an MR system is below 10 cm." In this paper, experimental studies were presented that showed temperature increases of 74 degrees Centigrade and higher in guide wires after 30 seconds of magnetic resonance scanning.

In articles by T. Sommer et al. ("MRI and cardiac pacemakers: In vitro eval. and in vivo studies in 51 patients at 0.5 T," Radiology 2000; 215–869–879) and R. Luechinger et al. ("Heating Effects of MRI on pacemaker leads: Effect of lead types, lead positioning, and reproducibility of finds [abstract] PACE 1999; 22:717), multiple studies were presented of the heating effects of MRI coils (including 0.5 Tesla coils) on endocardial pacemaker leads. In these studies, increases in lead tip temperatures of from 10 to 20 degrees Centigrade were "common."

Reference also may be had to a publication by J. Coman et al. ("Pacemaker safety during MRI at 1.5 Tesla [abstract], Journal of American College of Cardiology 2001; [37 [supplement A]:436A). This paper discussed a study of 25 MRI examinations at 1.5 Tesla in 24 patients with pacemakers; they indicated that 11 percent of the leads required a change in output to accommodate the altered threshold.

An article by F. Duru et al. ("Pacing in an MRI environment: Clinical and technical considerations on compatibility," European Heart Journal, 2001, 22: 113–124) presented data indicating that temperatures of almost 90 degrees Centigrade and myocardial necrosis were demonstrated in histologic studies.

An article by C. de Cock et al. ("Safety and feasibility of transesophageal pacing during MRI [MRI], European Heart Journal, 1005: 16 [Supplement]:401) presented animal studies using tranesophogeal pacing; these studies demonstrated that MRI induced heating resulted in tissue necrosis.

The Food and Drug Administration (FDA) has promulgated standard EN-45502-1 ("Active Implantable Medical Devices"). As is indicated in the S. Achenbach et al. reference, this standard allows for a maximum temperature increase during MRI imaging of only 2 degrees. Inasmuch as human body temperature is about 37 degrees Centigrade, it is desirable that an implanted medical device in contact with human biological tissue not exceed a temperature of greater than 39 degrees Centigrade when being exposed to MRI scanning.

It is an object of this invention to provide an assembly for protecting biological tissue from the adverse effects of heating during MRI scanning.

SUMMARY OF THE INVENTION

In accordance with this invention, there is provided an assembly for protecting biological tissue from the effects of heating. This assembly contains a conductor in contact with the biological tissue and forming an electrical circuit comprising the biological tissue. The assembly contains a device for modifying the impedance of the electrical circuit such that, at a frequency of from about 10 megahertz to about 150 megahertz, such impedance is at least about 0.5 ohms per centimeter of length of said conductor. The assembly also contains a device for limiting the flow of current through the biological tissue such that, when the assembly is exposed to an alternating electromagnetic field at a frequency of 64 megahertz and a direct current magnetic field strength of 1.5 Tesla for 15 minutes, the temperature of the biological tissue does not exceed 42 degrees Celsius.

BRIEF DESCRIPTION OF THE DRAWINGS

The present invention will be more fully understood by reference to the following detailed thereof, when read in conjunction with the attached drawings, wherein like reference numerals refer to like elements, and wherein:

FIGS. 6A through 6E are schematic representations of several preferred magnetic shields;

DESCRIPTION OF THE PREFERRED EMBODIMENTS

Figure 1:
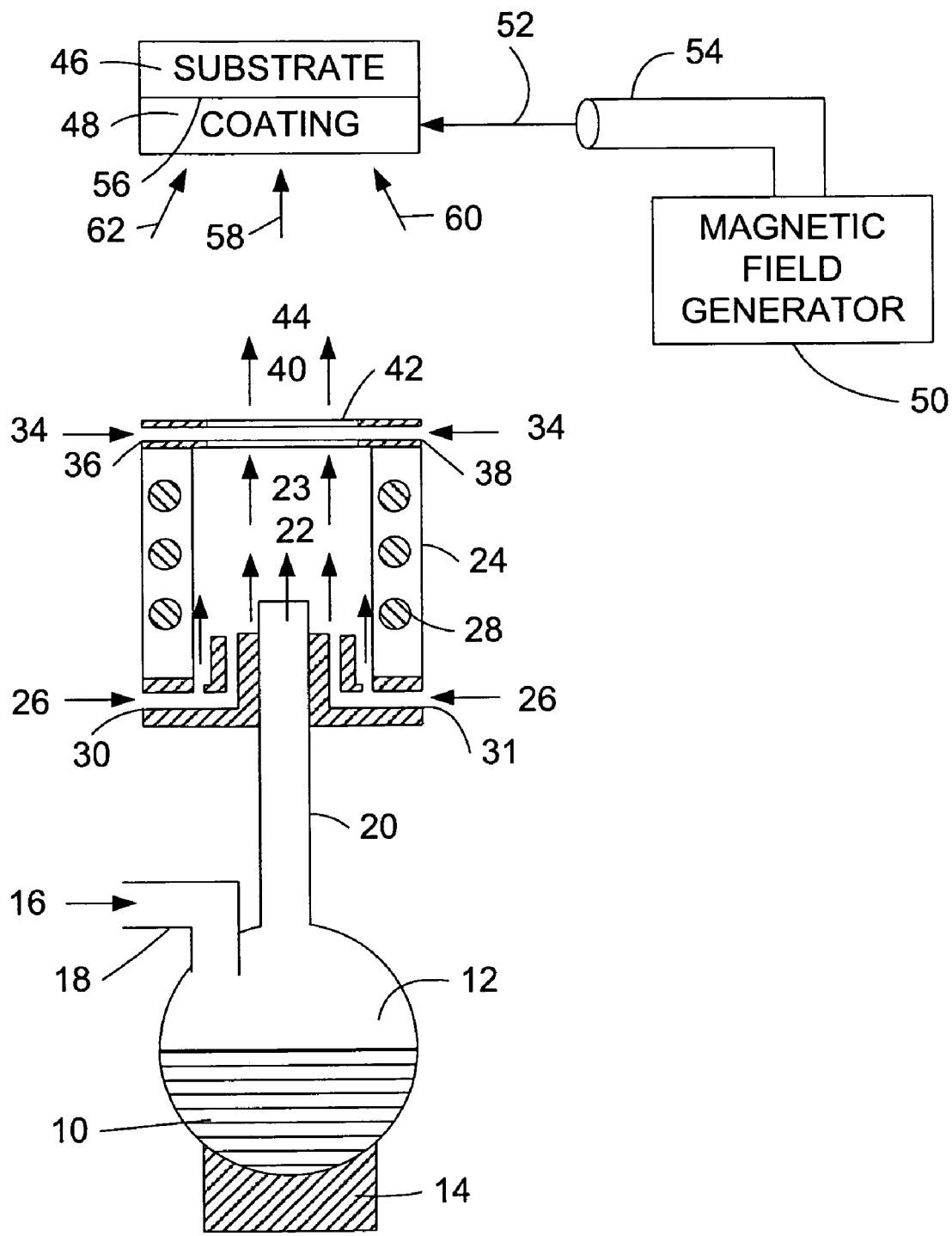
FIG. 1 is a schematic illustration of one preferred embodiment of the process of the invention.

FIG. 1 is a schematic illustration of one process of the invention which may be used to make nanomagnetic material. This FIG. 1 is similar in many respects to the FIG. 1 of U.S. Pat. No. 5,213,851, the entire disclosure of which is hereby incorporated by reference into this specification.

Referring to FIG. 1, and in the preferred embodiment depicted therein, it is preferred that the reagents charged into misting chamber 12 will be sufficient to form a nano-sized ferrite in the process. The term ferrite, as used in this specification, refers to a material that exhibits ferromagnetism. Ferromagnetism is a property, exhibited by certain metals, alloys, and compounds of the transition (iron group) rare earth and actinide elements, in which the internal magnetic moments spontaneously organize in a common direction; ferromagnetism gives rise to a permeability considerably greater than that of vacuum and to magnetic hysteresis. See, e.g, page 706 of Sybil B. Parker's "McGraw-Hill Dictionary of Scientific and Technical Terms," Fourth Edition (McGraw-Hill Book Company, New York, N.Y., 1989).

In one embodiment, the ferromagnetic material contains $Fe_2O_3$. See, for example, U.S. Pat. No. 3,576,672 of Harris et al., the entire disclosure of which is hereby incorporated by reference into this specification.

In one embodiment, the ferromagnetic material contains garnet. Pure iron garnet has the formula $M_3Fe_5O_{12}$; see, e.g., pages 65–256 of Wilhelm H. Von Aulock's "Handbook of Microwave Ferrite Materials" (Academic Press, New York, 1965). Garnet ferrites are also described, e.g., in U.S. Pat. No. 4,721,547, the disclosure of which is hereby incorporated by reference into this specification.

In another embodiment, the ferromagnetic material contains a spinel ferrite. Spinel ferrites usually have the formula $MFe_2O_4$, wherein M is a divalent metal ion and Fe is a trivalent iron ion. M is typically selected from the group consisting of nickel, zinc, magnesium, manganese, and like. These spinel ferrites are well known and are described, for example, in U.S. Pat. Nos. 5,001,014, 5,000,909, 4,966,625, 4,960,582, 4,957,812, 4,880,599, 4,862,117, 4,855,205, 4,680,130, 4,490,268, 3,822,210, 3,635,898, 3,542,685, 3,421,933, and the like. The disclosure of each of these patents is hereby incorporated by reference into this specification. Reference may also be had to pages 269–406 of the Von Aulock book for a discussion of spinel ferrites.

In yet another embodiment, the ferromagnetic material contains a lithium ferrite. Lithium ferrites are often described by the formula $(Li_{0.5}Fe_{0.5})_2+(Fe_2)3+O_4$. Some illustrative lithium ferrites are described on pages 407–434 of the aforementioned Von Aulock book and in U.S. Pat. Nos. 4,277,356, 4,238,342, 4,177,438, 4,155,963, 4,093,781, 4,067,922, 3,998,757, 3,767,581, 3,640,867, and the like. The disclosure of each of these patents is hereby incorporated by reference into this specification.

In yet another embodiment, the ferromagnetic material contains a hexagonal ferrite. These ferrites are well known and are disclosed on pages 451–518 of the Von Aulock book and also in U.S. Pat. Nos. 4,816,292, 4,189,521, 5,061,586, 5,055,322, 5,051,201, 5,047,290, 5,036,629, 5,034,243, 5,032,931, and the like. The disclosure of each of these patents is hereby incorporated by reference into this specification.

Figure 3:
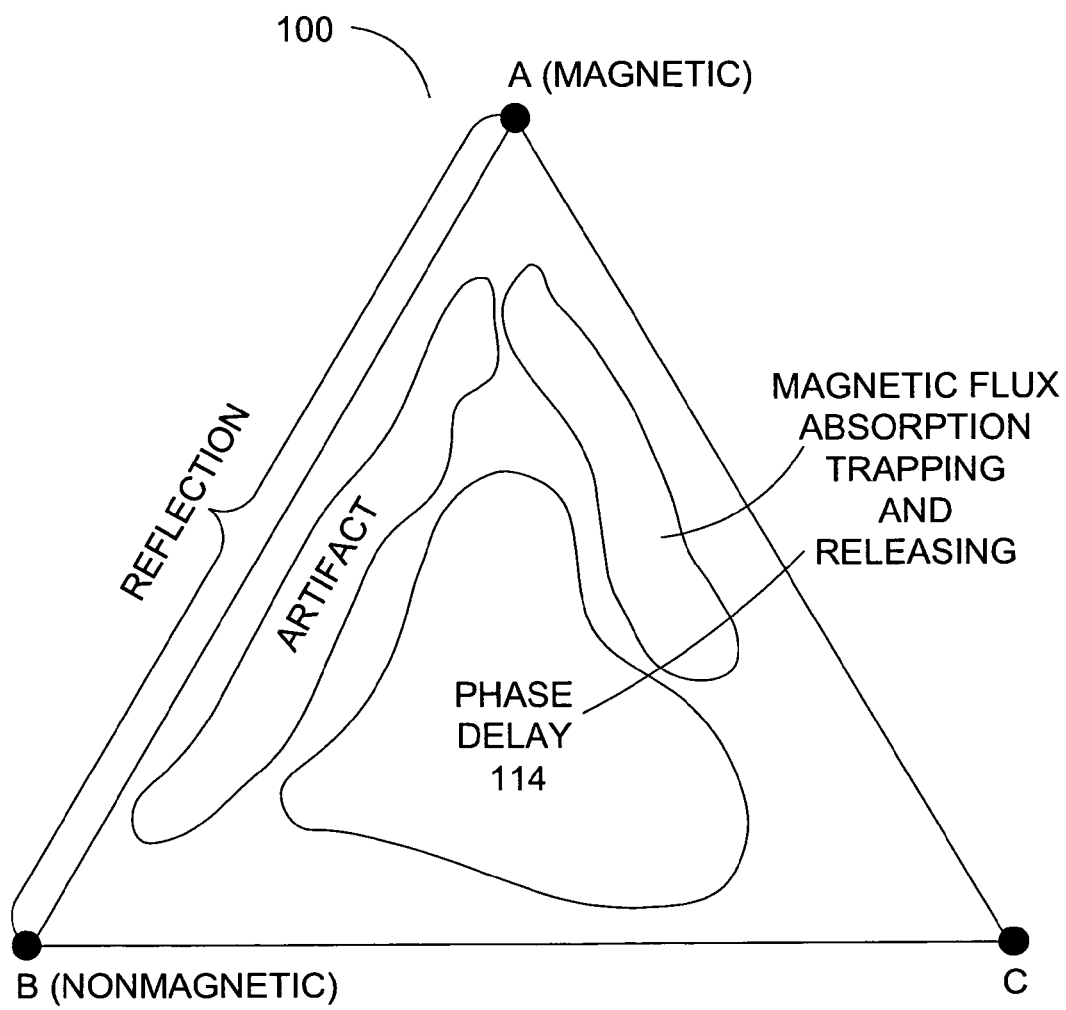
FIG. 3 is a phase diagram of a preferred nanomagnetic material.

In yet another embodiment, the ferromagnetic material contains one or more of the moieties A, B, and C disclosed in the phase diagram of FIG. 3 and discussed elsewhere in this specification.

Referring again to FIG. 1, and in the preferred embodiment depicted therein, it will be appreciated that the solution 10 will comprise reagents necessary to form the required ferromagnetic material. For example, in one embodiment, in order to form the spinel nickel ferrite of the formula $NiFe_2O_4$, the solution should contain nickel and iron, which may be present in the form of nickel nitrate and iron nitrate. By way of further example, one may use nickel chloride and iron chloride to form the same spinel. By way of further example, one may use nickel sulfate and iron sulfate.

It will be apparent to skilled chemists that many other combinations of reagents, both stoichiometric and nonstoichiometric, may be used in applicants' process to make many different ferromagnetic materials.

In one preferred embodiment, the solution 10 contains the reagent needed to produce a desired ferrite in stoichiometric ratio. Thus, to make the $NiFe_2O_4$ ferrite in this embodiment, one mole of nickel nitrate may be charged with every two moles of iron nitrate.

In one embodiment, the starting materials are powders with purities exceeding 99 percent.

In one embodiment, compounds of iron and the other desired ions are present in the solution in the stoichiometric ratio.

In one preferred embodiment, ions of nickel, zinc, and iron are present in a stoichiometric ratio of 0.5/0.5/2.0, respectively. In another preferred embodiment, ions of lithium and iron are present in the ratio of 0.5/2.5. In yet another preferred embodiment, ions of magnesium and iron are present in the ratio of 1.0/2.0. In another embodiment, ions of manganese and iron are present in the ratio 1.0/2.0. In yet another embodiment, ions of yttrium and iron are present in the ratio of 3.0/5.0. In yet another embodiment, ions of lanthanum, yttrium, and iron are present in the ratio of 0.5/2.5/5.0. In yet another embodiment, ions of neodymium, yttrium, gadolinium, and iron are present in the ratio of 1.0/1.07/0.93/5.0, or 1.0/1.1/0.9/5.0, or 1/1.12/0.88/5.0. In yet another embodiment, ions of samarium and iron are present in the ratio of 3.0/5.0. In yet another embodiment, ions of neodymium, samarium, and iron are present in the ratio of 0.1/2.9/5.0, or 0.25/2.75/5.0, or 0.375/2.625/5.0. In yet another embodiment, ions of neodymium, erbium, and iron are present in the ratio of 1.5/1.5/5.0. In yet another embodiment, samarium, yttrium, and iron ions are present in the ratio of 0.51/2.49/5.0, or 0.84/2.16/5.0, or 1.5/1.5/5.0. In yet another embodiment, ions of yttrium, gadolinium, and iron are present in the ratio of 2.25/0.75/5.0, or 1.5/1.5/5.0, or 0.75/2.25/5.0. In yet another embodiment, ions of terbium, yttrium, and iron are present in the ratio of 0.8/2.2/5.0, or 1.0/2.0/5.0. In yet another embodiment, ions of dysprosium, aluminum, and iron are present in the ratio of 3/x/5−x, when x is from 0 to 1.0. In yet another embodiment, ions of dysprosium, gallium, and iron are also present in the ratio of 3/x/5−x. In yet another embodiment, ions of dysprosium, chromium, and iron are also present in the ratio of 3/x/5−x.

The ions present in the solution may be holmium, yttrium, and iron, present in the ratio of z/3−z/5.0, where z is from about 0 to 1.5.

The ions present in the solution may be erbium, gadolinium, and iron in the ratio of 1.5/1.5/5.0. The ions may be erbium, yttrium, and iron in the ratio of 1.5/1.5/1.5, or 0.5/2.5/5.0.

The ions present in the solution may be thulium, yttrium, and iron, in the ratio of 0.06/2.94/5.0.

The ions present in the solution may be ytterbium, yttrium, and iron, in the ratio of 0.06/2.94/5.0.

The ions present in the solution may be lutetium, yttrium, and iron in the ratio of y/3−y/5.0, wherein y is from 0 to 3.0.

The ions present in the solution may be iron, which can be used to form $Fe_{6O8}$ (two formula units of $Fe_3O_4$). The ions present may be barium and iron in the ratio of 1.0/6.0, or 2.0/8.0. The ions present may be strontium and iron, in the ratio of 1.0/12.0. The ions present may be strontium, chromium, and iron in the ratio of 1.0/1.0/10.0, or 1.0/6.0/6.0. The ions present may be suitable for producing a ferrite of the formula $(Me_x)_3+Ba_{1-x}Fe_{12}O_{19}$, wherein Me is a rare earth selected from the group consisting of lanthanum, promethium, neodymium, samarium, europium, and mixtures thereof.

The ions present in the solution may contain barium, either lanthanum or promethium, iron, and cobalt in the ratio of 1−a/a/12−a/a, wherein a is from 0.0 to 0.8.

The ions present in the solution may contain barium, cobalt, titanium, and iron in the ratio of 1.0/b/b/12−2b, wherein b is from 0.0 to 1.6.

The ions present in the solution may contain barium, nickel or cobalt or zinc, titanium, and iron in the ratio of 1.0/c/c/12–2c, wherein c is from 0.0 to 1.5.

The ions present in the solution may contain barium, iron, iridium, and zinc in the ratio of 1.0/12–2d/d/d, wherein d is from 0.0 to 0.6.

The ions present in the solution may contain barium, nickel, gallium, and iron in the ratio of 1.0/2.0/7.0/9.0, or 1.0/2.0/5.0/11.0. Alternatively, the ions may contain barium, zinc, gallium or aluminum, and iron in the ratio of 1.0/2.0/3.0/13.0.

Each of these ferrites is well known to those in the ferrite art and is described, e.g., in the aforementioned Von Aulock book.

The ions described above are preferably available in solution 10 in water-soluble form, such as, e.g., in the form of water-soluble salts. Thus, e.g., one may use the nitrates or the chlorides or the sulfates or the phosphates of the cations. Other anions which form soluble salts with the cation(s) also may be used.

Alternatively, one may use salts soluble in solvents other than water. Some of these other solvents which may be used to prepare the material include nitric acid, hydrochloric acid, phosphoric acid, sulfuric acid, and the like. As is well known to those skilled in the art, many other suitable solvents may be used; see, e.g., J. A. Riddick et al., "Organic Solvents, Techniques of Chemistry," Volume II, 3rd edition (Wiley-Interscience, New York, N.Y., 1970).

In one preferred embodiment, where a solvent other than water is used, each of the cations is present in the form of one or more of its oxides. For example, one may dissolve iron oxide in nitric acid, thereby forming a nitrate. For example, one may dissolve zinc oxide in sulfuric acid, thereby forming a sulfate. One may dissolve nickel oxide in hydrochloric acid, thereby forming a chloride. Other means of providing the desired cation(s) will be readily apparent to those skilled in the art.

In general, as long as the desired cation(s) are present in the solution, it is not significant how the solution was prepared.

In general, one may use commercially available reagent grade materials. Thus, by way of illustration and not limitation, one may use the following reagents available in the 1988–1989 Aldrich catalog (Aldrich Chemical Company, Inc., Milwaukee, Wis.): barium chloride, catalog number 31,866-3; barium nitrate, catalog number 32,806-5; barium sulfate, catalog number 20,276-2; strontium chloride hexhydrate, catalog number 20,466-3; strontium nitrate, catalog number 20,449-8; yttrium chloride, catalog number 29,826-3; yttrium nitrate tetrahydrate, catalog number 21,723-9; yttrium sulfate octahydrate, catalog number 20,493-5. This list is merely illustrative, and other compounds which can be used will be readily apparent to those skilled in the art. Thus, any of the desired reagents also may be obtained from the 1989–1990 AESAR catalog (Johnson Matthey/AESAR Group, Seabrook, N.H.), the 1990/1991 Alfa catalog (Johnson Matthey/Alfa Products, Ward Hill, Ma.), the Fisher 88 catalog (Fisher Scientific, Pittsburgh, Pa.), and the like.

As long as the metals present in the desired ferrite material are present in solution 10 in the desired stoichiometry, it does not matter whether they are present in the form of a salt, an oxide, or in another form. In one embodiment, however, it is preferred to have the solution contain either the salts of such metals, or their oxides.

The solution 10 of the compounds of such metals preferably will be at a concentration of from about 0.01 to about 1,000 grams of said reagent compounds per liter of the resultant solution. As used in this specification, the term liter refers to 1,000 cubic centimeters.

In one embodiment, it is preferred that solution 10 have a concentration of from about 1 to about 300 grams per liter and, preferably, from about 25 to about 170 grams per liter. It is even more preferred that the concentration of said solution 10 be from about 100 to about 160 grams per liter. In an even more preferred embodiment, the concentration of said solution 10 is from about 140 to about 160 grams per liter.

In one preferred embodiment, aqueous solutions of nickel nitrate, and iron nitrate with purities of at least 99.9 percent are mixed in the molar ratio of 1:2 and then dissolved in distilled water to form a solution with a concentration of 150 grams per liter.

In one preferred embodiment, aqueous solutions of nickel nitrate, zinc nitrate, and iron nitrate with purities of at least 99.9 percent are mixed in the molar ratio of 0.5:0.5:2 and then dissolved in distilled water to form a solution with a concentration of 150 grams per liter.

In one preferred embodiment, aqueous solutions of zinc nitrate, and iron nitrate with purities of at least 99.9 percent are mixed in the molar ratio of 1:2 and then dissolved in distilled water to form a solution with a concentration of 150 grams per liter.

In one preferred embodiment, aqueous solutions of nickel chloride, and iron chloride with purities of at least 99.9 percent are mixed in the molar ratio of 1:2 and then dissolved in distilled water to form a solution with a concentration of 150 grams per liter.

In one preferred embodiment, aqueous solutions of nickel chloride, zinc chloride, and iron chloride with purities of at least 99.9 percent are mixed in the molar ratio of 0.5:0.5:2 and then dissolved in distilled water to form a solution with a concentration of 150 grams per liter.

In one preferred embodiment, aqueous solutions of zinc chloride, and iron chloride with purities of at least 99.9 percent are mixed in the molar ratio of 1:2 and then dissolved in distilled water to form a solution with a concentration of 150 grams per liter.

In one embodiment, mixtures of chlorides and nitrides may be used. Thus, for example, in one preferred embodiment, the solution is comprised of both iron chloride and nickel nitrate in the molar ratio of 2.0/1.0.

Referring again to FIG. 1, and to the preferred embodiment depicted therein, the solution 10 in misting chamber 12 is preferably caused to form into an aerosol, such as a mist.

The term aerosol, as used in this specification, refers to a suspension of ultramicroscopic solid or liquid particles in air or gas, such as smoke, fog, or mist. See, e.g., page 15 of "A dictionary of mining, mineral, and related terms," edited by Paul W. Thrush (U.S. Department of the Interior, Bureau of Mines, 1968), the disclosure of which is hereby incorporated by reference into this specification.

As used in this specification, the term mist refers to gas-suspended liquid particles which have diameters less than 10 microns.

The aerosol/mist consisting of gas-suspended liquid particles with diameters less than 10 microns may be produced from solution 10 by any conventional means which causes sufficient mechanical disturbance of said solution. Thus, one may use mechanical vibration. In one preferred embodiment, ultrasonic means are used to mist solution 10. As is known to those skilled in the art, by varying the means used to cause such mechanical disturbance, one can also vary the size of the mist particles produced.

As is known to those skilled in the art, ultrasonic sound waves (those having frequencies above 20,000 hertz) may be used to mechanically disturb solutions and cause them to mist. Thus, by way of illustration, one may use the ultrasonic nebulizer sold by the DeVilbiss Health Care, Inc. of Somerset, Pa.; see, e.g., the Instruction Manual for the "Ultra-Neb 99 Ultrasonic Nebulizer, publication A-850-C (published by DeVilbiss, Somerset, Pa., 1989), the disclosure of which is hereby incorporated by reference into this specification.

In the embodiment shown in FIG. 1, the oscillators of ultrasonic nebulizer 14 are shown contacting an exterior surface of misting chamber 12. In this embodiment, the ultrasonic waves produced by the oscillators are transmitted via the walls of the misting chamber 12 and effect the misting of solution 10.

In another embodiment, not shown, the oscillators of ultrasonic nebulizer 14 are in direct contact with solution 10.

In one embodiment, it is preferred that the ultrasonic power used with such machine should be in excess of one watt and, more preferably, in excess of 10 watts. In one embodiment, the power used with such machine exceeds about 50 watts.

During the time solution 10 is being caused to mist, it is preferably contacted with carrier gas to apply pressure to the solution and mist. It is preferred that a sufficient amount of carrier gas be introduced into the system at a sufficiently high flow rate so that pressure on the system is in excess of atmospheric pressure. Thus, for example, in one embodiment wherein chamber 12 has a volume of about 200 cubic centimeters, the flow rate of the carrier gas was from about 100 to about 150 milliliters per minute.

In one embodiment, the carrier gas 16 is introduced via feeding line 18 at a rate sufficient to cause solution 10 to mist at a rate of from about 0.5 to about 20 milliliters per minute. In one embodiment, the misting rate of solution 10 was from about 1.0 to about 3.0 milliliters per minute.

Substantially any gas that facilitates the formation of plasma may be used as carrier gas 16. Thus, by way of illustration, one may use oxygen, air, argon, nitrogen, and the like. It is preferred that the carrier gas used be a compressed gas under a pressure in excess 760 millimeters of mercury. In this embodiment, the use of the compressed gas facilitates the movement of the mist from the misting chamber 12 to the plasma region 22.

The misting container 12 may be any reaction chamber conventionally used by those skilled in the art and should preferably be constructed out of such acid-resistant materials such as glass, plastic, and the like.

The mist from misting chamber 12 is fed via misting outlet line 20 into the plasma region 22 of plasma reactor 24. In plasma reactor 24, the mist is mixed with plasma generated by plasma gas 26 and subjected to radio frequency radiation provided by a radio-frequency coil 28.

The plasma reactor 24 provides energy to form plasma and to cause the plasma to react with the mist. Any of the plasmas reactors well known to those skilled in the art may be used as plasma reactor 24. Some of these plasma reactors are described in J. Mort et al., "Plasma Deposited Thin Films" (CRC Press Inc., Boca Raton, Fla., 1986); "Methods of Experimental Physics," Volume 9—Parts A and B, Plasma Physics (Academic Press, New York, 1970/1971); N. H. Burlingame, "Glow Discharge Nitriding of Oxides," Ph.D. thesis (Alfred University, Alfred, N.Y., 1985), available from University Microfilm International, Ann Arbor, Mich. Each of these publications is hereby incorporated by reference into this specification.

In one preferred embodiment, the plasma reactor 24 was "model 56 torch" available from the TAFA Inc. of Concord, N.H. It was operated at a frequency of about 4 megahertz and an input power of 30 kilowatts.

Into feeding lines 30 and 32 is fed plasma gas 26. As is known to those skilled in the art, a plasma can be produced by passing gas into a plasma reactor. A discussion of the formation of plasma is contained in B. Chapman's "Glow Discharge Processes" (John Wiley & Sons, New York, 1980), the disclosure of which is hereby incorporated by reference into this specification.

In one preferred embodiment, the plasma gas used is a mixture of argon and oxygen. In another embodiment, the plasma gas is a mixture of nitrogen and oxygen. In yet another embodiment, the plasma gas is pure argon or pure nitrogen.

When the plasma gas is pure argon or pure nitrogen, it is preferred to introduce into the plasma reactor at a flow rate of from about 5 to about 30 liters per minute.

When a mixture of oxygen and either argon or nitrogen is used, the concentration of oxygen in the mixture should preferably be from about 1 to about 40 volume percent and, preferably, from about 15 to about 25 volume percent. When such a mixture is used, the flow rates of each gas in the mixture should be adjusted to obtain the desired gas concentrations. Thus, by way of illustration, in one embodiment which uses a mixture of argon and oxygen, the argon flow rate was 15 liters per minute, and the oxygen flow rate was 40 liters per minute.

In one embodiment, auxiliary oxygen 34 is fed into the top of reactor 24, between the plasma region 22 and the flame region 40, via lines 36 and 38. In this embodiment, the auxiliary oxygen is not involved in the formation of plasma but is involved in the enhancement of the oxidation of the ferrite material.

Radio frequency energy is applied to the reagents in the plasma reactor 24, and it causes vaporization of the mist.

In general, the energy is applied at a frequency of from about 100 to about 30,000 kilohertz. In one embodiment, the radio frequency used is from about 1 to 20 megahertz. In another embodiment, the radio frequency used is from about 3 to about 5 megahertz.

As is known to those skilled in the art, such radio frequency alternating currents may be produced by conventional radio frequency generators. Thus, by way of illustration, said TAPA Inc. "model 56 torch" is attached to a radio frequency generator rated for operation at 35 kilowatts which manufactured by Lepel Company (a division of TAFA Inc.) and which generates an alternating current with a frequency of 4 megaherz at a power input of 30 kilowatts. Thus, e.g., one may use an induction coil driven at 2.5–5.0 megahertz which is sold as the "PLASMOC 2" by ENI Power Systems, Inc. of Rochester, N.Y.

The use of these type of radio-frequency generators is described in the Ph.D. theses entitled (1) "Heat Transfer Mechanisms in High-Temperature Plasma Processing of Glasses," Donald M. McPherson (Alfred University, Alfred, N.Y., January, 1988) and (2) the aforementioned Nicholas H. Burlingame's "Glow Discharge Nitriding of Oxides."

The plasma vapor 23 formed in plasma reactor 24 is allowed to exit via the aperture 42 and can be visualized in the flame region 40. In this region, the plasma contacts air which is at a lower temperature than the plasma region 22, and a flame is visible. A theoretical model of the plasma/flame is presented on pages 88 et seq. of said McPherson thesis.

The vapor 44 present in flame region 40 is propelled upward towards substrate 46. Any material onto which vapor 44 will condense may be used as a substrate. Thus, by way of illustration, one may use nonmagnetic materials such alumina, glass, gold-plated ceramic materials, and the like. In one preferred embodiment, substrate 46 consists essentially of a magnesium oxide material such as single crystal magnesium oxide, polycrystalline magnesium oxide, and the like.

In another embodiment, the substrate 46 consists essentially of zirconia such as, e.g., yttrium stabilized cubic zirconia.

In another embodiment, the substrate 46 consists essentially of a material selected from the group consisting of strontium titanate, stainless steel, alumina, sapphire, and the like.

The aforementioned listing of substrates is merely meant to be illustrative, and it will be apparent that many other substrates may be used. Thus, by way of illustration, one may use any of the substrates mentioned in M. Sayer's "Ceramic Thin Films . . . "article, supra. Thus, for example, in one embodiment it is preferred to use one or more of the substrates described on page 286 of "Superconducting Devices," edited by S. T. Ruggiero et al. (Academic Press, Inc., Boston, 1990).

One advantage of applicants' process is that the substrate may be of substantially any size or shape, and it may be stationary or movable. Because of the speed of the coating process, the substrate 46 may be moved across the aperture 42 and have any or all of its surface be coated with the 48.

As will be apparent to those skilled in the art, in the embodiment depicted in FIG. 1, the substrate 46 and the coating 48 are not drawn to scale but have been enlarged to the sake of ease of representation.

Referring again to FIG. 1, the substrate 46 may be at ambient temperature. Alternatively, one may use additional heating means to heat the substrate prior to, during, or after deposition of the coating.

In one preferred embodiment, a heater (not shown) is used to heat the substrate to a temperature of from about 100 to about 800 degrees centigrade.

In one aspect of this embodiment, temperature sensing means (not shown) may be used to sense the temperature of the substrate and, by feedback means (not shown) adjust the output of the heater (not shown). In one embodiment, not shown, when the substrate 46 is relatively near flame region 40, optical pyrometry measurement means (not shown) may be used to measure the temperature near the substrate.

In one embodiment, shutter (not shown) is used to selectively interrupt the flow of vapor 44 to substrate 46. The use of this shutter is important prior to the time the flame region has become stable; and the vapor should preferably not be allowed to impinge upon the substrate prior to such time.

The substrate 46 may be moved in a plane which is substantially parallel to the top of plasma chamber 24. Alternatively, or additionally, it may be moved in a plane which is substantially perpendicular to the top of plasma chamber 24. In one embodiment, the substrate 46 is moved stepwise along a predetermined path to coat the substrate only at certain predetermined areas.

In one embodiment, rotary substrate motion is utilized to expose as much of the surface of a complex-shaped article to the coating. This rotary substrate motion may be effected by conventional means. See, e.g., "Physical Vapor Deposition," edited by Russell J. Hill (Temescal Division of The BOC Group, Inc., Berkeley, Calif., 1986).

The process of this embodiment of the invention allows one to coat an article at a deposition rate of from about 0.01 to about 10 microns per minute and, preferably, from about 0.1 to about 1.0 microns per minute, with a substrate with an exposed surface of 35 square centimeters. One may determine the thickness of the film coated upon said reference substrate material (with an exposed surface of 35 square centimeters) by means well known to those skilled in the art.

The film thickness can be monitored in situ, while the vapor is being deposited onto the substrate. Thus, by way of illustration, one may use an IC-6000 thin film thickness monitor (as referred to as "deposition controller") manufactured by Leybold Inficon Inc. of East Syracuse, N.Y.

The deposit formed on the substrate may be measured after the deposition by standard profilometry techniques. Thus, e.g., one may use a DEKTAK Surface Profiler, model number 900051 (available from Sloan Technology Corporation, Santa Barbara, Calif.).

In general, at least about 80 volume percent of the particles in the as-deposited film are smaller than about 1 microns. It is preferred that at least about 90 percent of such particles are smaller than 1 micron. Because of this fine grain size, the surface of the film is relatively smooth.

In one preferred embodiment, the as-deposited film is post-annealed.

It is preferred that the generation of the vapor in plasma rector 24 be conducted under substantially atmospheric pressure conditions. As used in this specification, the term "substantially atmospheric" refers to a pressure of at least about 600 millimeters of mercury and, preferably, from about 600 to about 1,000 millimeters of mercury. It is preferred that the vapor generation occur at about atmospheric pressure. As is well known to those skilled in the art, atmospheric pressure at sea level is 760 millimeters of mercury; see, e.g., page 60 of said "A dictionary of mining, mineral, and related terms," supra.

The process of this invention may be used to produce coatings on a flexible substrate such as, e.g., stainless steel strips, silver strips, gold strips, copper strips, aluminum strips, and the like. One may deposit the coating directly onto such a strip. Alternatively, one may first deposit one or more buffer layers onto the strip(s). In other embodiments, the process of this invention may be used to produce coatings on a rigid or flexible cylindrical substrate, such as a tube, a rod, or a sleeve.

Referring again to FIG. 1, and in the preferred embodiment depicted therein, as the coating 48 is being deposited onto the substrate 46, and as it is undergoing solidification thereon, it is preferably subjected to a magnetic field produced by magnetic field generator 50.

It is preferred that the magnetic field produced by the magnetic field generator 50 have a field strength of from about 2 Gauss to about 40 Tesla.

It is preferred to expose the deposited material for at least 10 seconds and, more preferably, for at least 30 seconds to the magnetic field, until the magnetic moments of the nano-sized particles being deposited have been substantially aligned.

As used herein, the term "substantially aligned" means that the inductance of the device being formed by the deposited nano-sized particles is at least 90 percent of its maximum inductance. One may determine when such particles have been aligned by measuring the inductance, the permeability, and/or the hysteresis loop of the deposited material.

One may measure the degree of alignment of the deposited particles with an impedance meter, a inductance meter, or a SQUID.

In one embodiment, the degree of alignment of the deposited particles is measured with an inductance. One may use a conventional conductance meter such as, e.g., the conductance meters disclosed in U.S. Pat. Nos. 4,779,462, 4,937,995, 5,728,814 (apparatus for determining and recording injection does in syringes using electrical inductance), U.S. Pat. Nos. 6,318,176, 5,014,012, 4,869,598, 4,258,315 (inductance meter), U.S. Pat. No. 4,045,728 (direct reading inductance meter), U.S. Pat. Nos. 6,252,923, 6,194,898, 6,006,023 (molecular sensing apparatus), U.S. Pat. No. 6,048,692 (sensors for electrically sensing binding events for supported molecular receptors), and the like. The entire disclosure of each of these United States patents is hereby incorporated by reference into this specification.

When measuring the inductance of the coated sample, the inductance is measured using an applied wave with a specified frequency. As the magnetic moments of the coated samples align, the inductance increases until a specified value; and it rises in accordance with a specified time constant in the measurement circuitry.

In one embodiment, the deposited material is contacted with the magnetic field until the inductance of the deposited material is at least about 90 percent of its maximum value under the measurement circuitry. At this time, the magnetic particles in the deposited material has been aligned to at least about 90 percent of the maximum extent possible for maximizing the inductance of the sample.

By way of illustration, a metal rod with a diameter of 1 micron and a length of 1 millimeter, when uncoated with magnetic nano-sized particles, might have an inductance of about 1 nanohenry. When this metal rod is coated with, e.g., nano-sized ferrites, then the inductance of the coated rod might be 5 nanohenries or more. When the magnetic moments of the coating are aligned, then the inductance might increase to 50 nanohenries, or more. As will be apparent to those skilled in the art, the inductance of the coated article will vary, e.g., with the shape of the article, and also with the frequency of the applied electromagnetic field.

One may use any of the conventional magnetic field generators known to those skilled in the art to produce such as magnetic field. Thus, by way of illustration and not limitation, one may use one or more of the magnetic field generators disclosed in U.S. Pat. Nos. 6,503,364, 6,377,149 (magnetic field generator for magnetron plasma generation), U.S. Pat. No. 6,353,375 (magnetostatic wave device), U.S. Pat. No. 6,340,888 (magnetic field generator for MRI), U.S. Pat. Nos. 6,336,989, 6,335,617 (device for calibrating a magnetic field generator), U.S. Pat. Nos. 6,313,632, 6,297,634, 6,275,128, 6,246,066 (magnetic field generator and charged particle beam irradiator), U.S. Pat. No. 6,114,929 (magnetostatic wave device), U.S. Pat. No. 6,099,459 (magnetic field generating device and method of generating and applying a magnetic field), U.S. Pat. Nos. 5,795,212, 6,106,380 (deterministic magnetorheological finishing), U.S. Pat. No. 5,839,944 (apparatus deterministic magnetorheological finishing), U.S. Pat. No. 5,971,835 (system for abrasive jet shaping and polishing of a surface using a magnetorheological fluid), U.S. Pat. Nos. 5,951,369, 6,506,102 (system for magnetorheological finishing of substrates), U.S. Pat. Nos. 6,267,651, 6,309,285 (magnetic wiper), and the like. The entire disclosure of each of these United States patents is hereby incorporated by reference into this specification.

In one embodiment, the magnetic field is 1.8 Tesla or less; in this embodiment, the magnetic field can be applied with, e.g., electromagnets disposed around a coated substrate.

For fields greater than about 2 Tesla, one may use superconducting magnets that produce fields as high as 40 Tesla. Reference may be had, e.g., to U.S. Pat. No. 5,319,333 (superconducting homogeneous high field magnetic coil), U.S. Pat. Nos. 4,689,563, 6,496,091 (superconducting magnet arrangement), U.S. Pat. No. 6,140,900 (asymmetric superconducting magnets for magnetic resonance imaging), U.S. Pat. No. 6,476,700 (superconducting magnet system), U.S. Pat. No. 4,763,404 (low current superconducting magnet), U.S. Pat. No. 6,172,587 (superconducting high field magnet), U.S. Pat. No. 5,406,204, and the like. The entire disclosure of each of these United States patents is hereby incorporated by reference into this specification.

In one embodiment, no magnetic field is applied to the deposited coating while it is being solidified. In this embodiment, as will be apparent to those skilled in the art, there still may be some alignment of the magnetic domains in a plane parallel to the surface of substrate as the deposited particles are locked into place in a matrix (binder) deposited onto the surface.

In one embodiment, depicted in FIG. 1, the magnetic field 52 is preferably delivered to the coating 48 in a direction that is substantially parallel to the surface 56 of the substrate 46. In another embodiment, depicted in FIG. 1, the magnetic field 58 is delivered in a direction that is substantially perpendicular to the surface 56. In yet another embodiment, the magnetic field 60 is delivered in a direction that is angularly disposed vis-à-vis surface 56 and may form, e.g., an obtuse angle (as in the case of field 62). As will be apparent, combinations of these magnetic fields may be used.

Figure 2:
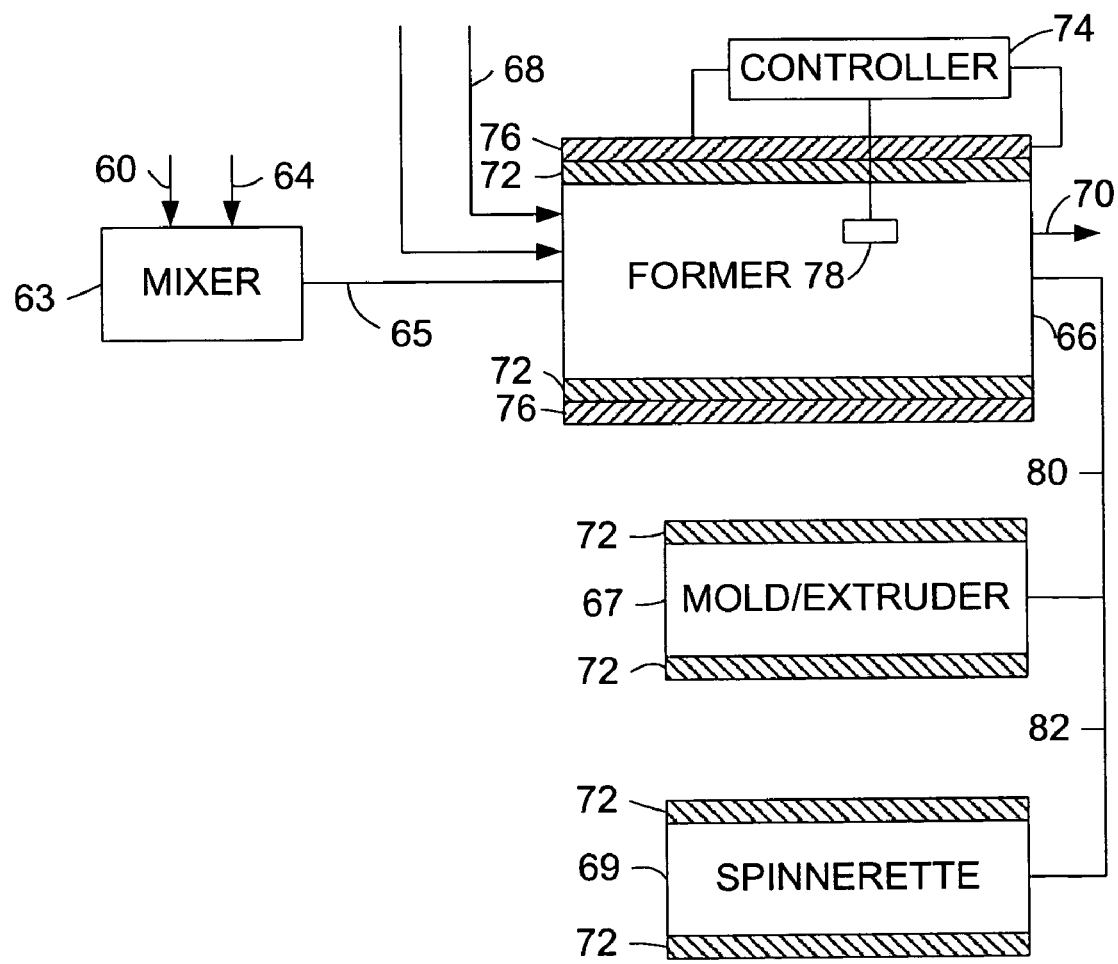
FIG. 2 is a schematic illustration of another preferred embodiment of the process of the invention.

FIG. 2 is a flow diagram of another process which may be used to make the nanomagnetic compositions of this invention. Referring to FIG. 2, and to the preferred process depicted therein, it will be seen that nano-sized ferromagnetic material(s), with a particle size less than about 100 nanometers, is preferably charged via line 60 to mixer 62. It is preferred to charge a sufficient amount of such nano-sized material(s) so that at least about 10 weight percent of the mixture formed in mixer 62 is comprised of such nano-sized material. In one embodiment, at least about 40 weight percent of such mixture in mixer 62 is comprised of such nano-sized material. In another embodiment, at least about 50 weight percent of such mixture in mixer 62 is comprised of such nano-sized material.

In one embodiment, one or more binder materials are charged via line 64 to mixer 62. In one embodiment, the binder used is a ceramic binder. These ceramic binders are well known. Reference may be had, e.g., to pages 172–197 of James S. Reed's "Principles of Ceramic Processing," Second Edition (John Wiley & Sons, Inc., New York, N.Y., 1995). As is disclosed in the Reed book, the binder may be a clay binder (such as fine kaolin, ball clay, and bentonite), an organic colloidal particle binder (such as microcrystalline cellulose), a molecular organic binder (such as natural gums, polyscaccharides, lignin extracts, refined alginate, cellulose ethers, polyvinyl alcohol, polyvinylbutyral, polymethyl methacrylate, polyethylene glycol, paraffin, and the like.)

In one embodiment, the binder may be a synthetic polymeric or inorganic composition. Thus, and referring to George S. Brady et al.'s "Materials Handbook," (McGraw-Hill, Inc., New York, N.Y. 1991), the binder may be acrylonitrile-butadiene-styrene (see pages 5–6), an acetal resin (see pages 6–7), an acrylic resin (see pages 10–12), an adhesive composition (see pages 14–18), an alkyd resin (see page 27–28), an allyl plastic (see pages 31–32), an amorphous metal (see pages 53–54), a biocompatible material (see pages 95–98), boron carbide (see page 106), boron nitride (see page 107), camphor (see page 135), one or more carbohydrates (see pages 138–140), carbon steel (see pages 146–151), casein plastic (see page 157), cast iron (see pages 159–164), cast steel (see pages 166–168), cellulose (see pages 172–175), cellulose acetate (see pages 175–177), cellulose nitrate (see pages 177), cement (see page 178–180), ceramics (see pages 180–182), cermets (see pages 182–184), chlorinated polyethers (see pages 191–191), chlorinated rubber (see pages 191–193), cold-molded plastics (see pages 220–221), concrete (see pages 225–227), conductive polymers and elastomers (see pages 227–228), degradable plastics (see pages 261–262), dispersion-strengthened metals (see pages 273–274), elastomers (see pages 284–290), enamel (see pages 299–301), epoxy resins (see pages 301–302), expansive metal (see page 313), ferrosilicon (see page 327), fiber-reinforced plastics (see pages 334–335), fluoroplastics (see pages 345–347), foam materials (see pages 349–351), fusible alloys (see pages 362–364), glass (see pages 376–383), glass-ceramic materials (see pages 383–384), gypsum (see pages 406–407), impregnated wood (see pages 422–423), latex (see pages 456–457), liquid crystals (see page 479), lubricating grease (see pages 488–492), magnetic materials (see pages 505–509), melamine resin (see pages 5210–521), metallic materials (see pages 522–524), nylon (see pages 567–569), olefin copolymers (see pages 574–576), phenol-formaldehyde resin (see pages 615–617), plastics (see pages 637–639), polyarylates (see pages 647–648), polycarbonate resins (see pages 648), polyester thermoplastic resins (see pages 648–650), polyester thermosetting resins (see pages 650–651), polyethylenes (see pages 651–654), polyphenylene oxide (see pages 644–655), polypropylene plastics (see pages 655–656), polystyrenes (see pages 656–658), proteins (see pages 666–670), refractories (see pages 691–697), resins (see pages 697–698), rubber (see pages 706–708), silicones (see pages 747–749), starch (see pages 797–802), superalloys (see pages 819–822), superpolymers (see pages 823–825), thermoplastic elastomers (see pages 837–839), urethanes (see pages 874–875), vinyl resins (see pages 885–888), wood (see pages 912–916), mixtures thereof, and the like.

Referring again to FIG. 2, one may charge to line 64 either one or more of these "binder material(s)" and/or the precursor(s) of these materials that, when subjected to the appropriate conditions in former 66, will form the desired mixture of nanomagnetic material and binder.

Referring again to FIG. 2, and in the preferred process depicted therein, the mixture within mixer 62 is preferably stirred until a substantially homogeneous mixture is formed. Thereafter, it may be discharged via line 65 to former 66.

One process for making a fluid composition comprising nanomagnetic particles is disclosed in U.S. Pat. No. 5,804,095, "Magnetorheological Fluid Composition", of Jacobs et al. The disclosure of this patent is incorporated herein by reference. In this patent, there is disclosed a process comprising numerous material handling steps used to prepare a nanomagnetic fluid comprising iron carbonyl particles. One suitable source of iron carbonyl particles having a median particle size of 3.1 microns is the GAF Corporation.

The process of Jacobs et al, is applicable to one aspect of the present invention, wherein such nanomagnetic fluid would further comprise a polymer binder, thereby forming a nanomagnetic paint. In one embodiment, the nanomagnetic paint would be formulated without abrasive particles of cerium dioxide. In another embodiment, the nanomagnetic fluid would further comprise a polymer binder, and AlN would be substituted for cerium dioxide.

It is known that there are many suitable mixing processes and apparatus for the milling, particle size reduction, and mixing of fluids comprising solid particles. For example, the iron carbonyl particles or other ferromagnetic particles of the paint could be further reduced to a size on the order of 100 nanometers or less, and/or thoroughly mixed with a binder polymer and/or a liquid solvent by the use of a ball mill, a sand mill, a paint shaker holding a vessel containing the paint components and hard steel or ceramic beads; a homogenizer, such as the Model Ytron Z made by the Ytron Quadro Corporation of Chesham, United Kingdom, or the Microfluidics M700 made by the MFIC Corporation of Newton, Mass.; a powder dispersing mixer such as the Ytron Zyclon mixer, or the Ytron Xyclon mixer, or the Ytron PID mixer by the Ytron Quadro Corporation; a grinding mill such as the Model F10 Mill by the Ytron Quadro Corporation; high shear mixers such as the Ytron Y mixer by the Ytron Quadro Corporation, the Silverson Laboratory Mixer by the Silverson Corporation of East Longmeadow, Mass. The use of one or more of these apparatus in series or in parallel may produce a suitably formulated nanomagnetic paint.

Referring again to FIG. 2, the former 66 is preferably equipped with an input line 68 and an exhaust line 70 so that the atmosphere within the former can be controlled. One may utilize an ambient atmosphere, an inert atmosphere, pure nitrogen, pure oxygen, mixtures of various gases, and the like. Alternatively, or additionally, one may use lines 68 and 70 to afford subatmospheric pressure, atmospheric pressure, or superatomspheric pressure within former 66.

In the embodiment depicted, former 66 is also comprised of an electromagnetic coil 72 that, in response from signals from controller 74, can control the extent to which, if any, a magnetic field is applied to the mixture within the former 66 (and also within the mold 67 and/or the spinnerette 69).

The controller 74 is also adapted to control the temperature within the former 66 by means of heating/cooling assembly.

In the embodiment depicted in FIG. 2, a sensor 78 determines the extent to which the desired nanomagnetic properties have been formed with the nano-sized material in the former 66; and, as appropriate, the sensor 78 imposes a magnetic field upon the mixture within the former 66 until the desired properties have been obtained.

In one embodiment, the sensor 78 is the inductance meter discussed elsewhere in this specification; and the magnetic field is applied until at least about 90 percent of the maximum inductance obtainable with the alignment of the magnetic moments has been obtained.

The magnetic field is preferably imposed until the nano-sized particles within former 78 (and the material with which it is admixed) have a mass density of at least about 0.001 grams per cubic centimeter (and preferably at least about 0.01 grams per cubic centimeter), a saturation magnetization of from about 1 to about 36,000 Gauss, a coercive force of from about 0.01 to about 5,000 Oersteds, and a relative magnetic permeability of from about 1 to about 500,000.

When the mixture within former 66 has the desired combination of properties (as reflected, e.g., by its substantially maximum inductance) and/or prior to that time, some or all of such mixture may be discharged via line 80 to a mold/extruder 67 wherein the mixture can be molded or extruded into a desired shape. A magnetic coil 72 also preferably may be used in mold/extruder 67 to help align the nano-sized particles.

Alternatively, or additionally, some or all of the mixture within former 66 may be discharged via line 82 to a spinnerette 69, wherein it may be formed into a fiber (not shown).

As will be apparent, one may make fibers by the process indicated that have properties analogous to the nanomagnetic properties of the coating 135 (see FIG. 6A), and/or nanoelectrical properties of the coating 141 (see FIG. 6B), and/or nanothermal properties of the coating 145 (see FIG. 6E). Such fiber or fibers may be made into fabric by conventional means. By the appropriate selection and placement of such fibers, one may produce a shielded fabric which provides protection against high magnetic voltages and/or high voltages and/or excessive heat.

Thus, in one embodiment, nanomagnetic and/or nanoelectrical and/or nanothermal fibers are woven together to produce a garment that will shield from the adverse effects of radiation such as, e.g., radiation experienced by astronauts in outer space.

Alternatively, or additionally, some or all of the mixture within former 66 may be discharged via line 84 to a direct writing applicator 90 such as a MicroPen applicator manufactured by OhmCraft Incorporated of Honeoye Falls, N.Y. Such an applicator is disclosed in U.S. Pat. No. 4,485,387, the disclosure of which is incorporated herein by reference. The use of this applicator to write circuits and other electrical structures is described in e.g. U.S. Pat. No. 5,861,558 of Buhl et al, "Strain Gauge and Method of Manufacture", the disclosure of which is incorporated herein by reference.

In the preferred embodiment, the nanomagnetic, nanoelectrical, and nanothermal compositions of the present invention, along with various conductor, resistor, capacitor, and inductor formulations are dispensed by the MicroPen device, to fabricate the circuits and structures of the present invention on devices such as, e.g. catheters and other biomedical devices.

In one preferred embodiment involving the writing of nanomagnetic circuit patterns and/or thin films, the direct writing applicator 90 as disclosed in U.S. Pat. No. 4,485,387 comprises an applicator tip 92 and an annular magnet 94, which provides a magnetic field 72. The use of such an applicator 90 to apply nanomagnetic coatings is particularly beneficial, because the presence of the magnetic field from magnet 94, through which the nanomagnetic fluid flows serves to orient the magnetic particles in situ as such nanomagnetic fluid is applied to a substrate. Such an orienting effect is described in U.S. Pat. No. 5,971,835, the disclosure of which is incorporated herein by reference. Once the nanomagnetic particles are properly oriented by such a field, or by another magnetic field source, the applied coating is cured by heating, by ultraviolet radiation, by an electron beam, or by other suitable means.

Nanomagnetic Compositions Comprised of Moieties A, B, and C.

The aforementioned process described in the preceding section of this specification may be adapted to produce other, comparable nanomagnetic structures, as is illustrated in FIG. 3.

Referring to FIG. 3, and in the preferred embodiment depicted therein, a phase diagram 100 is presented. As is illustrated by this phase diagram 100, the nanomagnetic material used in this embodiment of the invention preferably is comprised of one or more of moieties A, B, and C.

The moiety A depicted in phase diagram 100 is comprised of a magnetic element selected from the group consisting of a transition series metal, a rare earth series metal, or actinide metal, a mixture thereof, and/or an alloy thereof.

As is known to those skilled in the art, the transition series metals include chromium, manganese, iron, cobalt, and nickel. One may use alloys or iron, cobalt and nickel such as, e.g., iron-aluminum, iron-carbon, iron-chromium, iron-cobalt, iron-nickel, iron nitride ($Fe^3N$), iron phosphide, iron-silicon, iron-vanadium, nickel-cobalt, nickel-copper, and the like. One may use alloys of manganese such as, e.g., manganese-aluminum, manganese-bismuth, MnAs, MnSb, MnTe, manganese-copper, manganese-gold, manganese-nickel, manganese-sulfur and related compounds, manganese-antimony, manganese-tin, manganese-zinc, Heusler alloy W, and the like. One may use compounds and alloys of the iron group, including oxides of the iron group, halides of the iron group, borides of the transition elements, sulfides of the iron group, platinum and palladium with the iron group, chromium compounds, and the like.

One may use a rare earth and/or actinide metal such as, e.g., Ce, Pr, Nd, Pm, Sm, Eu, Gd, Tb, Dy, Ho, Er, Tm, Yb, Lu, La, mixtures thereof, and alloys thereof. One may also use one or more of the actinides such as, e.g., Th, Pa, U, Np, Pu, Am, Cm, Bk, Cf, Es, Fm, Md, No, Lr, Ac, and the like.

These moieties, compounds thereof, and alloys thereof are well known and are described, e.g., in the aforementioned text of R. S. Tebble et al. entitled "Magnetic Materials."

In one preferred embodiment, moiety A is selected from the group consisting of iron, nickel, cobalt, alloys thereof, and mixtures thereof. In this embodiment, the moiety A is magnetic, i.e., it has a relative magnetic permeability of from about 1 to about 500,000. As is known to those skilled in the art, relative magnetic permeability is a factor being a characteristic of a material, which is proportional to the magnetic induction produced in a material divided by the magnetic field strength; it is a tensor when these quantities are not parallel. See, e.g., page 4-128 of E. U. Condon et al.'s "Handbook of Physics" (McGraw-Hill Book Company, Inc., New York, N.Y., 1958).

The moiety A also preferably has a saturation magnetization of from about 1 to about 36,000 Gauss, and a coercive force of from about 0.01 to about 5,000 Oersteds.

The moiety A may be present in the nanomagnetic material either in its elemental form, as an alloy, in a solid solution, or as a compound.

It is preferred at least about 1 mole percent of moiety A be present in the nanomagnetic material (by total moles of A, B, and C), and it is more preferred that at least 10 mole percent of such moiety A be present in the nanomagnetic material (by total moles of A, B, and C). In one embodiment, at least 60 mole percent of such moiety A is present in the nanomagnetic material, (by total moles of A, B, and C.)

In addition to moiety A, it is preferred to have moiety B be present in the nanomagnetic material. In this embodiment, moieties A and B are admixed with each other. The mixture may be a physical mixture, it may be a solid solution, it may be comprised of an alloy of the A/B moieties, etc.

In one embodiment, the magnetic material A is dispersed within nonmagnetic material B. This embodiment is depicted schematically in FIG. 4.

Figure 4:
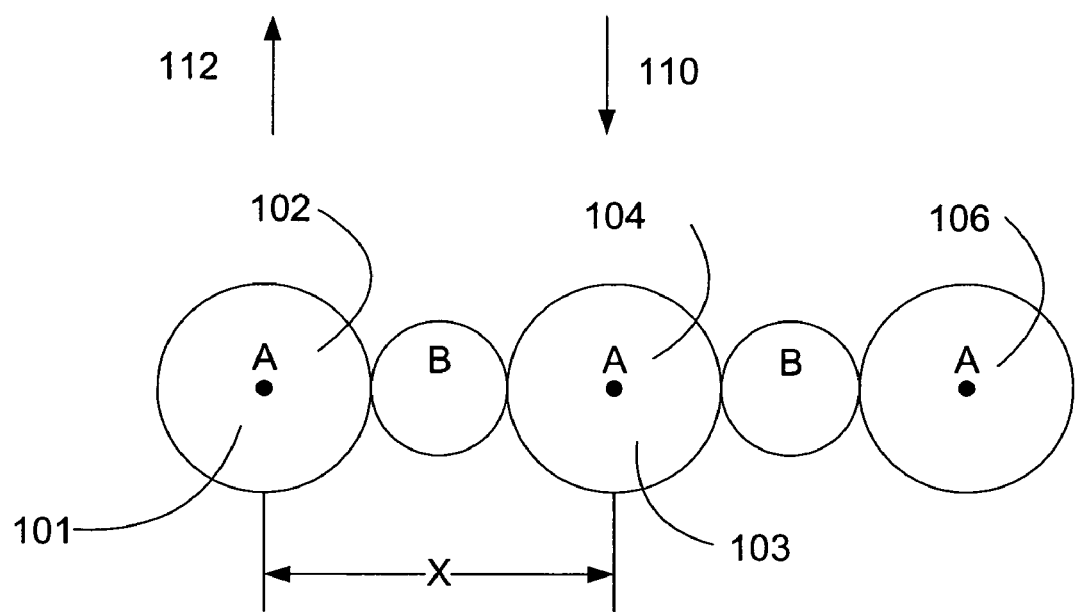
FIG. 4 is a schematic of the spacing between components of the nanomagnetic material of FIG. 3.

Referring to FIG. 4, and in the preferred embodiment depicted therein, it will be seen that A moieties 102, 104, and 106 are separated from each other either at the atomic level and/or at the nanometer level. The A moieties may be, e.g., A atoms, clusters of A atoms, A compounds, A solid solutions, etc; regardless of the form of the A moiety, it has the magnetic properties described hereinabove.

In the embodiment depicted in FIG. 4, each A moiety produces an independent magnetic moment. The coherence length (L) between adjacent A moieties is, on average, from about 0.1 to about 100 nanometers and, more preferably, from about 1 to about 50 nanometers.

Thus, referring again to FIG. 4, the normalized magnetic interaction between adjacent A moieties 102 and 104, and also between 104 and 106, is preferably described by the formula M=exp(-x/L), wherein M is the normalized magnetic interaction, exp is the base of the natural logarithm (and is approximately equal to 2.71828), x is the distance between adjacent A moieties, and L is the coherence length.

In one embodiment, and referring again to FIG. 4, x is preferably measured from the center 101 of A moiety 102 to the center 103 of A moiety 104; and x is preferably equal to from about 0.00001 times L to about 100 times L.

In one embodiment, the ratio of x/L is at least 0.5 and, preferably, at least 1.5.

Referring again to FIG. 3, the nanomagnetic material may be comprised of 100 percent of moiety A, provided that such moiety A has the required normalized magnetic interaction (M). Alternatively, the nanomagnetic material may be comprised of both moiety A and moiety B.

When moiety B is present in the nanomagnetic material, in whatever form or forms it is present, it is preferred that it be present at a mole ratio (by total moles of A and B) of from about 1 to about 99 percent and, preferably, from about 10 to about 90 percent.

The B moiety, in whatever form it is present, is nonmagnetic, i.e., it has a relative magnetic permeability of 1.0; without wishing to be bound to any particular theory, applicants believe that the B moiety acts as buffer between adjacent A moieties. One may use, e.g., such elements as silicon, aluminum, boron, platinum, tantalum, palladium, yttrium, zirconium, titanium, calcium, beryllium, barium, silver, gold, indium, lead, tin, antimony, germanium, gallium, tungsten, bismuth, strontium, magnesium, zinc, and the like.

In one embodiment, and without wishing to be bound to any particular theory, it is believed that B moiety provides plasticity to the nanomagnetic material that it would not have but for the presence of B. It is preferred that the bending radius of a substrate coated with both A and B moieties be no greater than 90 percent of the bending radius of a substrate coated with only the A moiety.

The use of the B material allows one to produce a coated substrate with a springback angle of less than about 45 degrees. As is known to those skilled in the art, all materials have a finite modulus of elasticity; thus, plastic deformation is followed by some elastic recovery when the load is removed. In bending, this recovery is called springback. See, e.g., page 462 of S. Kalparjian's "Manufacturing Engineering and Technology," Third Edition (Addison Wesley Publishing Company, New York, N.Y., 1995).

In one preferred embodiment, the B material is aluminum and the C material is nitride. Without wishing to be bound to any particular theory, applicants believe that aluminum nitride (and comparable materials) are both electrically insulating and thermally conductive, thus providing a excellent combination of properties.

Referring again to FIGS. 3 and 4, when an electromagnetic field 110 is incident upon the nanomagnetic material comprised of A and B (see FIG. 3), such a field will be reflected to some degree depending upon the ratio of moiety A and moiety B. In one embodiment, it is preferred that at least 1 percent of such field is reflected in the direction of arrow 112 (see FIG. 4). In another embodiment, it is preferred that at least about 10 percent of such field is reflected. In yet another embodiment, at least about 90 percent of such field is reflected. Without wishing to be bound to any particular theory, applicants believe that the degree of reflection depends upon the concentration of A in the A/B mixture.

M, the normalized magnetic interaction, preferably ranges from about $3 \times 10^{-44}$ to about 1.0.

In one preferred embodiment, M is from about 0.01 to 0.99. In another preferred embodiment, M is from about 0.1 to about 0.9.

Referring again to FIG. 3, and in one embodiment, the nanomagnetic material is comprised of moiety A, moiety C, and optionally moiety B. The moiety C is preferably selected from the group consisting of elemental oxygen, elemental nitrogen, elemental carbon, elemental fluorine, elemental chlorine, elemental hydrogen, and elemental helium, elemental neon, elemental argon, elemental krypton, elemental xenon, and the like.

It is preferred, when the C moiety is present, that it be present in a concentration of from about 1 to about 90 mole percent, based upon the total number of moles of the A moiety and/or the B moiety and C moiety in the composition.

Referring again to FIG. 3, and in the embodiment depicted, the area 114 produces a composition which optimizes the degree to which magnetic flux are initially trapped and/or thereafter released by the composition when a magnetic field is withdrawing from the composition.

Without wishing to be bound to any particular theory, applicants believe that, when a composition as described by area 114 is subjected to an alternating magnetic field, at least a portion of the magnetic field is trapped by the composition when the field is strong, and then this portion tends to be released when the field releases lessens in intensity.

Thus, e.g., when the magnetic field 110 is applied to the nanomagnetic material, it starts to increase, in a typical sine wave fashion. After a specified period of time a magnetic moment is created within the nanomagnetic material; but, because of the time delay, there is a phase shift.

The time delay will vary with the composition of the nanomagnetic material. By maximizing the amount of trapping, and by minimizing the amount of reflection and absorption, one may minimize the magnetic artifacts caused by the nanomagnetic shield.

Thus, one may optimize the A/B/C composition to preferably be within the area 114. In general, the A/B/C composition has molar ratios such that the ratio of A/(A and C) is from about 1 to about 99 mole percent and, preferably, from about 10 to about 90 mole percent. In one preferred embodiment, such ratio is from about 40 to about 60 molar percent.

The molar ratio of A/(A and B and C) generally is from about 1 to about 99 mole percent and, preferably, from about 10 to about 90 molar percent. In one embodiment, such molar ratio is from about 30 to about 60 molar percent.

The molar ratio of B/(A plus B plus C) generally is from about 1 to about 99 mole percent and, preferably, from about 10 to about 40 mole percent.

The molar ratio of C/(A plus B plus C) generally is from about 1 to about 99 mole percent and, preferably, from about 10 to about 50 mole percent.

In one embodiment, the composition of the nanomagnetic material is chosen so that the applied electromagnetic field 110 is absorbed by the nanomagnetic material by less than about 1 percent; thus, in this embodiment, the applied magnetic field 110 is substantially restored by correcting the time delay.

By utilizing nanomagnetic material that absorbs the electromagnetic field, one may selectively direct energy to various cells within a biological organism that are to treated. Thus, e.g., cancer cells can be injected with the nanomagnetic material and then destroyed by the application of externally applied electromagnetic fields. Because of the nano size of applicants' materials, they can readily and preferentially be directed to the malignant cells to be treated within a living organism. In this embodiment, the nanomagnetic material preferably has a particle size of from about 5 to about 10 nanometers.

OTHER EMBODIMENTS OF THE INVENTION

In the remainder of this specification, certain other preferred embodiments of applicants' invention will be described.

In one embodiment, the composition of this invention is comprised of nanomagnetic particles with a specified magnetization. As is known to those skilled in the art, magnetization is the magnetic moment per unit volume of a substance. Reference may be had, e.g., to U.S. Pat. Nos. 4,169,998, 4,168,481, 4,166,263, 5,260,132, 4,778,714, and the like. The entire disclosure of each of these United States patents is hereby incorporated by reference into this specification.

In this embodiment, the nanomagnetic particles are present within a layer that preferably has a saturation magnetization, at 25 degrees Centigrade, of from about 1 to about 36,000 Gauss, or higher. In one embodiment, the saturation magnetization at room temperature of the nanomagentic particles is from about 500 to about 10,000 Gauss. For a discussion of the saturation magnetization of various materials, reference may be had, e.g., to U.S. Pat. Nos. 4,705,613, 4,631,613, 5,543,070, 3,901,741 (cobalt, samarium, and gadolinium alloys), and the like. The entire disclosure of each of these United States patents is hereby incorporated by reference into this specification. As will be apparent to those skilled in the art, especially upon studying the aforementioned patents, the saturation magnetization of thin films is often higher than the saturation magnetization of bulk objects.

In one embodiment, it is preferred to utilize a thin film with a thickness of less than about 2 microns and a saturation magnetization in excess of 20,000 Gauss. The thickness of the layer of nanomagentic material is measured from the bottom surface of the layer that contains such material to the top surface of such layer that contains such material; and such bottom surface and/or such top surface may be contiguous with other layers of material (such as insulating material) that do not contain nanomagnetic particles.

Thus, e.g., one may make a thin film in accordance with the procedure described at page 156 of Nature, Volume 407, Sep. 14, 2000, that describes a multilayer thin film has a saturation magnetization of 24,000 Gauss.

By the appropriate selection of nanomagnetic particles, and the thickness of the films deposited, one may obtain saturation magnetizations of as high as at least about 36,000.

In one embodiment, the nanomagnetic materials used in the invention typically comprise one or more of iron, cobalt, nickel, gadolinium, and samarium atoms. Thus, e.g., typical nanomagnetic materials include alloys of iron and nickel (permalloy), cobalt, niobium, and zirconium (CNZ), iron, boron, and nitrogen, cobalt, iron, boron, and silica, iron, cobalt, boron, and fluoride, and the like. These and other materials are described in a book by J. Douglas Adam et al. entitled "Handbook of Thin Film Devices" (Academic Press, San Diego, Calif., 2000). Chapter 5 of this book beginning at page 185, describes "magnetic films for planar inductive components and devices;" and Tables 5.1 and 5.2 in this chapter describe many magnetic materials.

In one embodiment, the nanomagnetic material has a saturation magnetization of form about 1 to about 36,000 Gauss. In one embodiment, the nanomagnetic material has a saturation magnetization of from about 200 to about 26,000 Gauss.

In one embodiment, the nanomagnetic material also has a coercive force of from about 0.01 to about 5,000 Oersteds. The term coercive force refers to the magnetic field, H, which must be applied to a magnetic material in a symmetrical, cyclically magnetized fashion, to make the magnetic induction, B, vanish; this term often is referred to as magnetic coercive force. Reference may be had, e.g., to U.S. Pat. Nos. 4,061,824, 6,257,512, 5,967,223, 4,939,610, 4,741,953, and the like. The entire disclosure of each of these United States patents is hereby incorporated by reference into this specification.

In one embodiment, the nanomagnetic material has a coercive force of from about 0.01 to about 3,000 Oersteds. In yet another embodiment, the nanomagnetic material 103 has a coercive force of from about 0.1 to about 10.

In one embodiment, the nanomagnetic material preferably has a relative magnetic permeability of from about 1 to about 500,000; in one embodiment, such material has a relative magnetic permeability of from about 1.5 to about 260,000. As used in this specification, the term relative magnetic permeability is equal to B/H, and is also equal to the slope of a section of the magnetization curve of the film. Reference may be had, e.g., to page 4-28 of E. U. Condon et al.'s "Handbook of Physics" (McGraw-Hill Book Company, Inc., New York, 1958).

Reference also may be had to page 1399 of Sybil P. Parker's "McGraw-Hill Dictionary of Scientific and Technical Terms," Fourth Edition (McGraw Hill Book Company, New York, 1989). As is disclosed on this page 1399, permeability is " . . . a factor, characteristic of a material, that is proportional to the magnetic induction produced in a material divided by the magnetic field strength; it is a tensor when these quantities are not parallel.

Reference also may be had, e.g., to U.S. Pat. Nos. 6,181,232, 5,581,224, 5,506,559, 4,246,586, 6,390,443, and the like. The entire disclosure of each of these United States patents is hereby incorporated by reference into this specification.

In one embodiment, the nanomagnetic material has a relative magnetic permeability of from about 1.5 to about 2,000.

In one embodiment, the nanomagnetic material preferably has a mass density of at least about 0.001 grams per cubic centimeter; in one embodiment, such mass density is at least about 1 gram per cubic centimeter. As used in this specification, the term mass density refers to the mass of a give substance per unit volume. See, e.g., page 510 of the aforementioned "McGraw-Hill Dictionary of Scientific and Technical Terms." In one embodiment, the material has a mass density of at least about 3 grams per cubic centimeter. In another embodiment, the nanomagnetic material has a mass density of at least about 4 grams per cubic centimeter.

In one embodiment, it is preferred that the nanomagnetic material, and/or the article into which the nanomagnetic material has been incorporated, be interposed between a source a source of radiation and a substrate to be protected therefrom.

In one embodiment, the nanomagnetic material is in the form of a layer that preferably has a saturation magnetization, at 25 degree Centigrade, of from about 1 to about 36,000 Gauss, and preferably from about 1 to about 26,000 Gauss. In one embodiment, the saturation magnetization at room temperature of the nanomagnetic particles is from about 500 to about 10,000 Gauss.

In one embodiment, the nanomagnetic material is disposed within an insulating matrix so that any heat produced by such particles will be slowly dispersed within such matrix. Such matrix may be made from ceria, calcium oxide, silica, alumina, and the like. In general, the insulating material preferably has a thermal conductivity of less than about 20 (calories centimeters/square centimeters-degree Kelvin second)×10,000. See, e.g., page E-6 of the $63^{rd}$. Edition of the "Handbook of Chemistry and Physics" (CRC Press, Inc. Boca Raton, Fla., 1982).

In one embodiment, there is provided a coating of nanomagnetic particles that consists of a mixture of aluminum oxide ($Al_2O_3$), iron, and other particles that have the ability to deflect electromagnetic fields while remaining electrically non-conductive. Preferably the particle size in such a coating is approximately 10 nanometers. Preferably the particle packing density is relatively low so as to minimize electrical conductivity. Such a coating when placed on a fully or partially metallic object (such as a guide wire, catheter, stent, and the like) is capable of deflecting electromagnetic fields, thereby protecting sensitive internal components, while also preventing the formation of eddy currents in the metallic object or coating. The absence of eddy currents in a metallic medical device provides several advantages, to wit: (1) reduction or elimination of heating, (2) reduction or elimination of electrical voltages which can damage the device and/or inappropriately stimulate internal tissues and organs, and (3) reduction or elimination of disruption and distortion of a magnetic-resonance image.

Determination of the Heat Shielding Effect of the Magnetic Shield

In one preferred embodiment, the composition of this invention minimizes the extent to which a substrate increases its heat when subjected to a strong magnetic filed. This heat buildup can be determined in accordance with A.S.T.M. Standard Test F-2182-02, "Standard test method for measurement of radio-frequency induced heating near passive implant during magnetic resonance imaging."

In this test, the radiation used is representative of the fields present during MRI procedures. As is known to those skilled in the art, such fields typically include a static field with a strength of from about 0.5 to about 2 Teslas, a radio frequency alternating magnetic field with a strength of from about 20 microTeslas to about 100 microTeslas, and a gradient magnetic field that has three components—x, y, and z, each of which has a field strength of from about 0.05 to 500 milliTeslas.

During this test, a temperature probe is used to measure the temperature of an unshielded conductor when subjected to the magnetic field in accordance with such A.S.T.M. F-2182-02.

The same test is then is then performed upon a shielded conductor assembly that is comprised of the conductor and a magnetic shield.

The magnetic shield used may comprise nanomagnetic particles, as described hereinabove. Alternatively, or additionally, it may comprise other shielding material, such as, e.g., oriented nanotubes (see, e.g., U.S. Pat. No. 6,265,466).

In one embodiment, the shield is in the form of a layer of shielding material with a thickness of from about 10 nanometers to about 1 millimeter. In another embodiment, the thickness is from about 10 nanometers to about 20 microns.

In one preferred embodiment the shielded conductor is an implantable device and is connected to a pacemaker assembly comprised of a power source, a pulse generator, and a controller. The pacemaker assembly and its associated shielded conductor are preferably disposed within a living biological organism.

In one preferred embodiment, when the shielded assembly is tested in accordance with A.S.T.M. 2182-02, it will have a specified temperature increase ("$dT_S$"). The "$dT_C$" is the change in temperature of the unshielded conductor using precisely the same test conditions but omitting the shield. The ratio of $dT_S/dT_C$, is the temperature increase ratio; and one minus the temperature increase ratio ($1-dT_S/dT_C$) is defined as the heat shielding factor.

It is preferred that the shielded conductor assembly have a heat shielding factor of at least about 0.2. In one embodiment, the shielded conductor assembly has a heat shielding factor of at least 0.3.

In one embodiment, the nanomagnetic shield of this invention is comprised of an antithrombogenic material.

Antithrombogenic compositions and structures have been well known to those skilled in the art for many years. As is disclosed, e.g., in U.S. Pat. No. 5,783,570, the entire disclosure of which is hereby incorporated by reference into this specification, "Artificial materials superior in processability, elasticity and flexibility have been widely used as medical materials in recent years. It is expected that they will be increasingly used in a wider area as artificial organs such as artificial kidney, artificial lung, extracorporeal circulation devices and artificial blood vessels, as well as disposable products such as syringes, blood bags, cardiac catheters and the like. These medical materials are required to have, in addition to sufficient mechanical strength and durability, biological safety, which particularly means the absence of blood coagulation upon contact with blood, i.e., antithrombogenicity."

"Conventionally employed methods for imparting antithrombogenicity to medical materials are generally classified into three groups of (1) immobilizing a mucopolysaccharide (e.g., heparin) or a plasminogen activator (e.g., urokinase) on the surface of a material, (2) modifying the surface of a material so that it carries negative charge or hydrophilicity, and (3) inactivating the surface of a material. Of these, the method of (1) (hereinafter to be referred to briefly as surface heparin method) is further subdivided into the methods of (A) blending of a polymer and an organic solvent-soluble heparin, (B) coating of the material surface with an organic solvent-soluble heparin, (C) ionical bonding of heparin to a cationic group in the material, and (D) covalent bonding of a material and heparin."

"Of the above methods, the methods (2) and (3) are capable of affording a stable antithrombogenicity during a long-term contact with body fluids, since protein adsorbs onto the surface of a material to form a biomembrane-like surface. At the initial stage when the material has been introduced into the body (blood contact site) and when various coagulation factors etc. in the body have been activated, however, it is difficult to achieve sufficient antithrombogenicity without an anticoagulant therapy such as heparin administration."

Other antithrombogenic methods and compositions are also well known. Thus, by way of further illustration, United States published patent application 20010016611 discloses an antithrombogenic composition comprising an ionic complex of ammonium salts and heparin or a heparin derivative, said ammonium salts each comprising four aliphatic alkyl groups bonded thereto, wherein an ammonium salt comprising four aliphatic alkyl groups having not less than 22 and not more than 26 carbon atoms in total is contained in an amount of not less than 5% and not more than 80% of the total ammonium salt by weight. The entire disclosure of this published patent application is hereby incorporated by reference into this specification.

Thus, e.g., U.S. Pat. No. 5,783,570 discloses an organic solvent-soluble mucopolysaccharide consisting of an ionic complex of at least one mucopolysaccharide (preferably heparin or heparin derivative) and a quaternary phosphonium, an antibacterial antithrombogenic composition comprising said organic solvent-soluble mucopolysaccharide and an antibacterial agent (preferably an inorganic antibacterial agent such as silver zeolite), and to a medical material comprising said organic solvent soluble mucopolysaccharide. The organic solvent-soluble mucopolysaccharide, and the antibacterial antithrombogenic composition and medical material containing same are said to easily impart antithrombogenicity and antibacterial property to a polymer to be a base material, which properties are maintained not only immediately after preparation of the material but also after long-term elution. The entire disclosure of this United States patent is hereby incorporated by reference into this specification.

By way of further illustration, U.S. Pat. No. 5,049,393 discloses anti-thrombogenic compositions, methods for their production and products made therefrom. The anti-thrombogenic compositions comprise a powderized anti-thrombogenic material homogeneously present in a solidifiable matrix material. The anti-thrombogenic material is preferably carbon and more preferably graphite particles. The matrix material is a silicon polymer, a urethane polymer or an acrylic polymer. The entire disclosure of this United States patent is hereby incorporated by reference into this specification.

By way of yet further illustration, U.S. Pat. No. 5,013,717 discloses a leach resistant composition that includes a quaternary ammonium complex of heparin and a silicone. A method for applying a coating of the composition to a surface of a medical article is also disclosed in the patent. Medical articles having surfaces that are both lubricious and antithrombogenic are produced in accordance with the method of the patent.

A Process for Preparation of an Iron-Containing Thin Film

In one preferred embodiment of the invention, a sputtering technique is used to prepare an AlFe thin film as well as comparable thin films containing other atomic moieties, such as, e.g., elemental nitrogen, and elemental oxygen. Conventional sputtering techniques may be used to prepare such films by sputtering. See, for example, R. Herrmann and G. Brauer, "D.C.- and R.F. Magnetron Sputtering," in the "Handbook of Optical Properties: Volume I—Thin Films for Optical Coatings," edited by R. E. Hummel and K. H. Guenther (CRC Press, Boca Raton, Fla., 1955). Reference also may be had, e.g., to M. Allendorf, "Report of Coatings on Glass Technology Roadmap Workshop," Jan. 18–19, 2000, Livermore, Calif.; and also to U.S. Pat. No. 6,342,134, "Method for producing piezoelectric films with rotating magnetron sputtering system." The entire disclosure of each of these prior art documents is hereby incorporated by reference into this specification.

Although the sputtering technique is advantageously used, the plasma technique described elsewhere in this specification also may be used.

One may utilize conventional sputtering devices in this process. By way of illustration and not limitation, a typical sputtering system is described in U.S. Pat. No. 5,178,739, the entire disclosure of which is hereby incorporated by reference into this specification. As is disclosed in this patent, " . . . a sputter system 10 includes a vacuum chamber 20, which contains a circular end sputter target 12, a hollow, cylindrical, thin, cathode magnetron target 14, a RF coil 16 and a chuck 18, which holds a semiconductor substrate 19. The atmosphere inside the vacuum chamber 20 is controlled through channel 22 by a pump (not shown). The vacuum chamber 20 is cylindrical and has a series of permanent, magnets 24 positioned around the chamber and in close proximity therewith to create a multiple field configuration near the interior surface 15 of target 12. Magnets 26, 28 are placed above end sputter target 12 to also create a multipole field in proximity to target 12. A singular magnet 26 is placed above the center of target 12 with a plurality of other magnets 28 disposed in a circular formation around magnet 26. For convenience, only two magnets 24 and 28 are shown. The configuration of target 12 with magnets 26, 28 comprises a magnetron sputter source 29 known in the prior art, such as the Torus-10E system manufactured by K. Lesker, Inc. A sputter power supply 30 (DC or RF) is connected by a line 32 to the sputter target 12. A RF supply 34 provides power to RF coil 16 by a line 36 and through a matching network 37. Variable impedance 38 is connected in series with the cold end 17 of coil 16. A second sputter power supply 39 is connected by a line 40 to cylindrical sputter target 14. A bias power supply 42 (DC or RF) is connected by a line 44 to chuck 18 in order to provide electrical bias to substrate 19 placed thereon, in a manner well known in the prior art."

By way of yet further illustration, other conventional sputtering systems and processes are described in U.S. Pat. No. 5,569,506 (a modified Kurt Lesker sputtering system), U.S. Pat. No. 5,824,761 (a Lesker Torus 10 sputter cathode), U.S. Pat. Nos. 5,768,123, 5,645,910, 6,046,398 (sputter deposition with a Kurt J. Lesker Co. Torus 2 sputter gun), U.S. Pat. Nos. 5,736,488, 5,567,673, 6,454,910, and the like. The entire disclosure of each of these United States patents is hereby incorporated by reference into this specification.

By way of yet further illustration, one may use the techniques described in a paper by Xingwu Wang et al. entitled "Technique Devised for Sputtering AlN Thin Films," published in "the Glass Researcher," Volume 11, No. 2 (Dec. 12, 2002). The entire disclosure of this publication is hereby incorporated by reference into this specification.

In one preferred embodiment, a magnetron sputtering technique is utilized, with a Lesker Super System III system The vacuum chamber of this system is cylindrical, with a diameter of approximately one meter and a height of approximately 0.6 meters. The base pressure used is from about 0.001 to 0.0001 Pascals. In one aspect of this process, the target is a metallic FeAl disk, with a diameter of approximately 0.1 meter. The molar ratio between iron and aluminum used in this aspect is approximately 70/30. Thus, the starting composition in this aspect is almost non-magnetic. See, e.g., page 83 (FIG. 3.1$aii$) of R. S. Tebble et al.'s "Magnetic Materials" (Wiley-Interscience, New York, N.Y., 1969); this Figure discloses that a bulk composition containing iron and aluminum with at least 30 mole percent of aluminum (by total moles of iron and aluminum) is substantially non-magnetic.

In this aspect, to fabricate FeAl films, a DC power source is utilized, with a power level of from about 150 to about 550 watts (Advanced Energy Company of Colorado, model MDX Magnetron Drive). The sputtering gas used in this aspect is argon, with a flow rate of from about 0.0012 to about 0.0018 standard cubic meters per second. To fabricate FeAlN films in this aspect, in addition to the DC source, a pulse-forming device is utilized, with a frequency of from about 50 to about 250 MHz (Advanced Energy Company, model Sparc-le V). One may fabricate FeAlO films in a similar manner but using oxygen rather than nitrogen.

In this aspect, a typical argon flow rate is from about $(0.9$ to about $1.5) \times 10^{-3}$ standard cubic meters per second; a typical nitrogen flow rate is from about $(0.9$ to about $1.8) \times 10^{-3}$ standard cubic meters per second; and a typical oxygen flow rate is from about. $(0.5$ to about $2) \times 10^{-3}$ standard cubic meters per second. During fabrication, the pressure typically is maintained at from about 0.2 to about 0.4 Pascals. Such a pressure range is found to be suitable for nanomagnetic materials fabrications.

In this aspect, the substrate used may be either flat or curved. A typical flat substrate is a silicon wafer with or without a thermally grown silicon dioxide layer, and its diameter is preferably from about 0.1 to about 0.15 meters. A typical curved substrate is an aluminum rod or a stainless steel wire, with a length of from about 0.10 to about 0.56 meters and a diameter of from (about 0.8 to about $3.0) \times 10^{-3}$ meters. The distance between the substrate and the target is preferably from about 0.05 to about 0.26 meters.

In this aspect, in order to deposit a film on a wafer, the wafer is fixed on a substrate holder. The substrate may or may not be rotated during deposition. In one embodiment, to deposit a film on a rod or wire, the rod or wire is rotated at a rotational speed of from about 0.01 to about 0.1 revolutions per second, and it is moved slowly back and forth along its symmetrical axis with a maximum speed of about 0.01 meters per second.

In this aspect, to achieve a film deposition rate on the flat wafer of $5 \times 10^{-10}$ meters per second, the power required for the FeAl film is 200 watts, and the power required for the FeAlN film is 500 watts. The resistivity of the FeAlN film is approximately one order of magnitude larger than that of the metallic FeAl film. Similarly, the resistivity of the FeAlO film is about one order of magnitude larger than that of the metallic FeAl film.

Iron containing magnetic materials, such as FeAl, FeAlN and FeAlO, have been fabricated by various techniques. The magnetic properties of those materials vary with stoichiometric ratios, particle sizes, and fabrication conditions; see, e.g., R. S. Tebble and D. J. Craik, "Magnetic Materials", pp. 81–88, Wiley-Interscience, New York, 1969 As is disclosed in this reference, when the iron molar ratio in bulk FeAl materials is less than 70 percent or so, the materials will no longer exhibit magnetic properties.

However, it has been discovered that, in contrast to bulk materials, a thin film material often exhibits different properties due to the constraint provided by the substrate.

Figure 5:
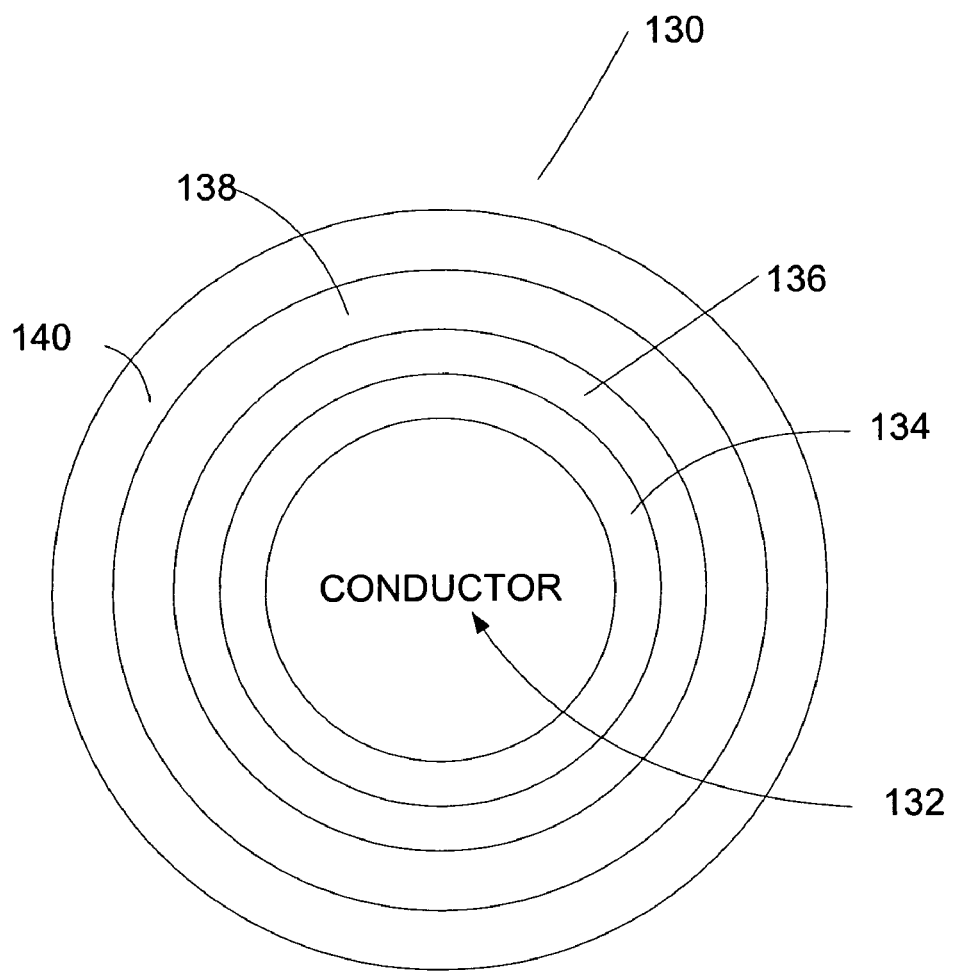
FIG. 5 is a schematic of a preferred magnetically shielded assembly.

FIG. 5 is a schematic sectional view, not drawn to scale, of a shielded conductor assembly 130 is comprised of a conductor 132 and, disposed around such conductor, a film 134 of nanomagnetic material. The conductor 132 preferably has a resistivity at 20 degrees Centigrade of from about 1 to about 100-microohm-centimeters.

The film 134 is preferably comprised of nanomagnetic material that has a maximum dimension of from about 10 to about 100 nanometers. The film 134 also preferably has a saturation magnetization of from about 200 to about 26,000 Gauss and a thickness of less than about 2 microns. In one embodiment, the magnetically shielded conductor assembly 130 is flexible, having a bend radius of less than 2 centimeters. Reference may be had, e.g., to U.S. Pat. No. 6,506,972, the entire disclosure of which is hereby incorporated by reference into this specification.

As used in this specification, the term flexible refers to an assembly that can be bent to form a circle with a radius of less than 2 centimeters without breaking. Put another way, the bend radius of the coated assembly is preferably less than 2 centimeters. Reference may be had, e.g., to U.S. Pat. Nos. 4,705,353, 5,946,439, 5,315,365, 4,641,917, 5,913,005, and the like. The entire disclosure of each of these United States patents is hereby incorporated by reference into this specification.

Without wishing to be bound to any particular theory, applicants believe that the use of nanomagnetic materials in their coatings and their articles of manufacture allows one to produce a flexible device that otherwise could not be produced were not the materials so used nano-sized (less than 100 nanometers).

Referring again to FIG. 5, one or more electrical filter circuit(s) 136 are preferably disposed around the nanomagnetic film 134. These circuit(s) may be deposited by conventional means.

In one embodiment, the electrical filter circuit(s) are deposited onto the film 134 by one or more of the techniques described in U.S. Pat. No. 5,498,289 (apparatus for applying narrow metal electrode), U.S. Pat. No. 5,389,573 (method for making narrow metal electrode), U.S. Pat. No. 5,973,573 (method of making narrow metal electrode), U.S. Pat. No. 5,973,259 (heated tool positioned in the X, Y, and 2-directions for depositing electrode), U.S. Pat. No. 5,741,557 (method for depositing fine lines onto a substrate), and the like. The entire disclosure of each of these United States patents is hereby incorporated by reference into this specification.

Referring again to FIG. 5, and in the preferred embodiment depicted therein, disposed around electrical filter circuit(s) 136 is a second film of nanomagnetic material 138, which may be identical to or different from film layer 134. In one embodiment, film layer 138 provides a different filtering response to electromagnetic waves than does film layer 134.

Disposed around nanomagnetic film layer 138 is a second layer of electrical filter circuit(s) 140. Each of circuit(s) 136 and circuit(s) 140 comprises at least one electrical circuit. It is preferred that the at least two circuits that comprise assembly 130 provide different electrical responses.

At high-frequencies, as is known to those skilled in the art, the inductive reactance of a coil is great. The inductive reactance $(X_L)$ is equal to $2\pi FL$, wherein F is the frequency (in hertz), and L is the inductance (in Henries).

At low-frequencies, by comparison, the capactitative reactance $(X_C)$ is high, being equal to $1/2\pi FC$, wherein C is the capacitance in Farads. The impedance of a circuit, Z, is equal to the square root of $(R^2+[X_L-X_C]^2)$, wherein R is the resistance, in ohms, of the circuit, and $X_L$ and $X_C$ are the inductive reactance and the capacitative reactance, respectively, in ohms, of the circuit.

Thus, for any particular alternating frequency electromagnetic wave, one can, by the appropriate selection of values for R, L, and C, pick a circuit that is purely resistive (in which case the inductive reactance is equal to the capacitative reactance at that frequency), is primarily inductive, or is primarily capacitative.

Maximum power transfer occurs at resonance, when the inductance reactance is equal to the capactitative reactance and the difference between them is zero. Conversely, minimum power transfer occurs when the circuit has little resistance in it (all circuits have some finite resistance) but is predominantly inductive or predominantly capacitative.

An LC tank circuit is an example of a circuit in which minimum power is transmitted. A tank circuit is a circuit in which an inductor and capacitor are in parallel; such a circuit appears, e.g., in the output stage of a radio transmitter.

An LC tank circuit exhibits the well-known flywheel effect, in which the energy introduced into the circuit continues to oscillate between the capacitor and inductor after an input signal has been applied; the oscillation stops when the tank-circuit finally loses the energy absorbed, but it resumes when a new source of energy is applied. The lower the inherent resistance of the circuit, the longer the oscillation will continue before dying out.

A typical tank circuit is comprised of a parallel-resonant circuit; and it acts as a selective filter. As is known to those skilled in the art, and as is disclosed in Stan Gibilisco's "Handbook of Radio & Wireless Technology" (McGraw-Hill, New York, N.Y., 1999), a selective filter is a circuit designed to tailor the way an electronic circuit or system responds to signals at various frequencies (see page 62).

The selective filter may be a bandpass filter (see pages 62–63 of the Gibilisco book) that comprises a resonant circuit, or a combination of resonant circuits, designed to discriminate against all frequencies except a specified frequency, or a band of frequencies between two limiting frequencies. In a parallel LC circuit, a bandpass filter shows a high impedance at the desired frequency or frequencies and a low impedance at unwanted frequencies. In a series LC configuration, the filter has a low impedance at the desired frequency or frequencies, and a high impedance at unwanted frequencies.

The selective filter may be a band-rejection filter, also known as a band-stop filter (see pages 63–65 of the Gibilisco book). This band-rejection filter comprises a resonant circuit adapted to pass energy at all frequencies except within a certain range. The attenuation is greatest at the resonant frequency or within two limiting frequencies.

The selective filter may be a notch filter; see page 65 of the Gibilisco book. A notch filter is a narrowband-rejection filter. A properly designed notch filter can produce attenuation in excess of 40 decibels in the center of the notch.

The selective filter may be a high-pass filter; see pages 65–66 of the Gibilisco book. A high-pass filter is a combination of capacitance, inductance, and/or resistance intended to produce large amounts of attenuation below a certain frequency and little or no attenuation above that frequency. The frequency above which the transition occurs is called the cutoff frequency.

The selective filter may be a low-pass filter; see pages 67–68 of the Gibilisco book. A low-pass filter is a combination of capacitance, inductance, and/or resistance intended to produce large amounts of attenuation above a certain frequency and little or no attenuation below that frequency.

FIG. 6A is a sectional schematic view of one preferred shielded assembly 131 that is comprised of a conductor 133 and, disposed around such conductor 133, a layer of nanomagnetic material 135.

In the embodiment depicted in FIG. 6A, the layer 135 of nanomagnetic material preferably has a thickness 137 of at least 150 nanometers and, more preferably, at least about 200 nanometers. In one embodiment; the thickness of layer 135 is from about 500 to about 1,000 nanometers.

The layer 135 of nanomagnetic material 137 preferably is comprised of nanomagnetic material formed, e.g., by subjecting the material in layer 137 to a magnetic field of from about 10 Gauss to about 40 Tesla for from about 1 to about 20 minutes. The layer 135 preferably has a mass density of at least about 0.001 grams per cubic centimeter (and preferably at least about 0.01 grams per cubic centimeter), a saturation magnetization of from about 1 to about 36,000 Gauss, and a coercive force of from about 0.01 to about 5,000.

In one embodiment, the B moiety is added to the nanomagnetic A moiety, preferably with a B:A molar ratio of from about 5:95 to about 95:5. In one aspect of this embodiment, the resistivity of the mixture of the B moiety and the A moiety is from about 1 micro-ohm-cm to about 10,000 micro-ohm-cm.

Without wishing to be bound to any particular theory, applicants believe that such a mixture of the A and B moieties provides two mechanisms for shielding the magnetic fields. One such mechanism/effect is the shielding provided by the nanomagnetic materials, described elsewhere in this specification. The other mechanism/effect is the shielding provided by the electrically conductive materials.

In one particularly preferred embodiment, the A moiety is iron, the B moiety is aluminum, and the molar ratio of A:B is about 70:30; the resistivity of this mixture is about 8 micro-ohms-cm.

FIG. 6B is a schematic sectional view of a magnetically shielded assembly 139 that is similar to assembly 131 but differs therefrom in that a layer 141 of nanoelectrical material is disposed around layer 135.

The layer of nanoelectrical material 141 preferably has a thickness of from about 0.5 to about 2 microns. The nanoelectrical material comprising layer 141 has a resistivity of from about 1 to about 100 microohm-centimeters. As is known to those skilled in the art, when nanoelectrical material is exposed to electromagnetic radiation, and in particular to an electric field, it will shield the substrate over which it is disposed from such electrical field. Reference may be had, e.g., to International patent publication WO9820719 in which reference is made to U.S. Pat. No. 4,963,291; each of these patents and patent applications is hereby incorporated by reference into this specification.

As is disclosed in U.S. Pat. No. 4,963,291 of Bercaw, one may produce electromagnetic shielding resins comprised of electroconductive particles, such as iron, aluminum, copper, silver and steel in sizes ranging from 0.5 to 0.50 microns. The entire disclosure of this United States patent is hereby incorporated by reference into this specification.

The nanoelectrical particles used in this invention preferably have a particle size within the range of from about 1 to about 100 microns, and a resistivity of from about 1.6 to about 100 microohm-centimeters. In one embodiment, such nanoelectrical particles comprise a mixture of iron and aluminum. In another embodiment, such nanoelectrical particles consist essentially of a mixture of iron and aluminum. It is preferred that, in such nanoelectrical particles, and in one embodiment, at least 9 moles of aluminum are present for each mole of iron. In another embodiment, at least about 9.5 moles of aluminum are present for each mole of iron. In yet another embodiment, at least 9.9 moles of aluminum are present for each mole of iron.

In one embodiment, the layer 141 of nanoelectrical material has a thermal conductivity of from about 1 to about 4 watts/centimeter-degree Kelvin.

In one embodiment, not shown, in either or both of layers 135 and 141 there is present both the nanoelectrical material and the nanomagnetic material One may produce such a layer 135 and/or 141 by simultaneously depositing the nanoelectrical particles and the nanomagnetic particles with, e.g., sputtering technology.

FIG. 6C is a sectional schematic view of a magnetically shielded assembly 143 that differs from assembly 131 in that it contains a layer 145 of nanothermal material disposed around the layer 135 of nanomagnetic material. The layer 145 of nanothermal material preferably has a thickness of less than 2 microns and a thermal conductivity of at least about 150 watts/meter-degree Kelvin and, more preferably, at least about 200 watts/meter-degree Kelvin. It is preferred that the resistivity of layer 145 be at least about $10^{10}$ microohm-centimeters and, more preferably, at least about $10^{12}$ microohm-centimeters. In one embodiment, the resistivity of layer 145 is at least about $10^{13}$ microohm centimeters. In one embodiment, the nanothermal layer is comprised of AlN.

In one embodiment, depicted in FIG. 6C, the thickness 147 of all of the layers of material coated onto the conductor 133 is preferably less than about 20 microns.

In FIG. 6D, a sectional view of an assembly 149 is depicted that contains, disposed around conductor 133, layers of nanomagnetic material 135, nanoelectrical material 141, nanomagnetic material 135, and nanoelectrical material 141.

In FIG. 6E, a sectional view of an assembly 151 is depicted that contains, disposed around conductor 133, a layer 135 of nanomagnetic material, a layer 141 of nanoelectrical material, a layer 135 of nanomagnetic material, a layer 145 of nanothermal material, and a layer 135 of nanomagnetic material. Optionally disposed in layer 153 is antithrombogenic material that is biocompatible with the living organism in which the assembly 151 is preferably disposed.

In the embodiments depicted in FIGS. 6A through 6E, the coatings 135, and/or 141, and/or 145, and/or 153, are disposed around a conductor 133. In one embodiment, the conductor so coated is preferably part of medical device, preferably an implanted medical device (such as, e.g., a pacemaker). In another embodiment, in addition to coating the conductor 133, or instead of coating the conductor 133, the actual medical device itself is coated.

Devices Incorporating the Shielded Conductor Assembly

In this section of the specification, various devices that incorporate the shielded conductor assemblies disclosed in FIGS. 6A through 6E are described. The invention described in this section of the specification relates generally to an implantable device that is immune or hardened to electromagnetic insult or interference. More particularly, and in one preferred embodiment, the invention is directed to implantable medical leads that utilize shielding to harden or make these systems immune from electromagnetic insult, namely magnetic-resonance imaging insult.

The coatings of this invention may be used to coat a single conductor 133. Alternatively, or additionally, one may coat a multiple strand conductor. It is to be understood that multiple strand conductors may be shielded by coating each strand separately, or by coating the multiple strand bundle. It is also to be understood that the multiple conductors within a single lead may be positioned concentrically to one another, or positioned spaced apart. It is also to be understood that the internally positioned conductors may be free to move, for example to rotate or translate, to for example control the motion of an active fixation electrode. By way of illustration, the shielded conductors may be used in the lead designs shown in U.S. Pat. Nos. 6,289,251, 6,285,910, 6,192,280, 6,185,463, 6,178,355, 6,144,882, 6,119,042, 6,096,069, 6,066,166, 6,061,598, 6,040,369, 6,038,463, 6,026,567, 6,018,683, 6,016,436, 6,006,122, 5,999,858, 5,991,668, 5,968,087, 5,968,086, 5,967,977, 5,964,795, 5,957,970, 5,957,967, 5,957,965, 5,954,759, 5,948,015, 5,935,159, 5,897,585, 5,871,530, 5,871,528, 5,853,652, 5,796,044, 5,760,341, 5,702,437, 5,676,694, 5,584,873, 5,522,875, 5,423,881, 5,411,545, 5,354,327, 5,336,254, 5,336,253, 5,324,321, 5,303,704, 5,238,006, 5,217,027, and 5,007,435. The entire disclosure of each of these United States patents is hereby incorporated by reference into this specification.

In one embodiment, a conductor assembly comprised of a multifilar coiled conductor with a spiral configuration; is coated with the coating constructs of this invention. Reference to such a multifilar conductor is made, e.g., in U.S. Pat. No. 5,954,759, the entire disclosure of which is hereby incorporated by reference into this specification.

In one embodiment, one or more of such coating constructs are applied to a monofilar coiled conductor such as, e.g., the monofilar coiled conductor disclosed in U.S. Pat. No. 5,954,759. The entire disclosure of such United States patent is hereby incorporated by reference into this specification.

By way of further illustration, the coating constructs may be used to coat one or more of the lead designs shown in U.S. Pat. Nos. 6,289,251, 6,285,910, 6,192,280, 6,185,463, 6,178,355, 6,144,882, 6,119,042, 6,096,069, 6,066,166, 6,061,598, 6,040,369, 6,038,463, 6,026,567, 6,018,683, 6,016,436, 6,006,122, 5,999,858, 5,991,668, 5,968,087, 5,968,086, 5,967,977, 5,964,795, 5,957,970, 5,957,967, 5,957,965, 5,954,759, 5,948,015, 5,935,159, 5,897,585, 5,871,530, 5,871,528, 5,853,652, 5,796,044, 5,760,341, 5,702,437, 5,676,694, 5,584,873, 5,522,875, 5,423,881, 5,411,545, 5,354,327, 5,336,254, 5,336,253, 5,324,321, 5,303,704, 5,238,006, 5,217,027, and 5,007,435, the entire disclosure of each of which is hereby incorporated by reference into this specification. When so used, the modified assemblies thus produced are resistant to electromagnetic radiation.

In one embodiment, the coating constructs are used to coat a conductor assembly comprised of a multifilar conductor disposed inside a monofilar conductor. In another embodiment, the coating constructs are used to coat a conductor assembly wherein the multifiar conductor is disposed outside the monofilar conductor. In one aspect of this embodiment, only portions of the conductors are shielded.

By way of further illustration, a discontinuous shield is produced by a discontinuous coating of nanomagnetic particles and/or other coating constructs. This coating, e.g., may be may be intermittingly discontinuous along its axial dimension, to provide for example, reduced exposure to an externally applied electromagnetic field. This coating may be, e.g., discontinuous at its proximal end, to provide for example, an electrically conductive surface for attachment to a medical device, such as an implantable pulse generator, a cardioversion-defibrilator pacemaker, an insulin pump, or other tissue or organ stimulating or sensing device. This coating, e.g., may be discontinuous along its distal end, to provide for example, an electrically conductive surface for contacting tissues or organs.

A discontinuous shield may be applied to non-wire conductors, such as for example a solid rod or other geometry conductor, used for example as an electrode for transmitting and/or receiving electrical signals to/from tissues or organs. The discontinuous shield may be applied to any of the conductor or lead configurations described above and/or in U.S. Pat. Nos. 6,289,251, 6,285,910, 6,192,280, 6,185,463, 6,178,355, 6,144,882, 6,119,042, 6,096,069, 6,066,166, 6,061,598, 6,040,369, 6,038,463, 6,026,567, 6,018,683, 6,016,436, 6,006,122, 5,999,858, 5,991,668, 5,968,087, 5,968,086, 5,967,977, 5,964,795, 5,957,970, 5,957,967, 5,957,965, 5,954,759, 5,948,015, 5,935,159, 5,897,585, 5,871,530, 5,871,528, 5,853,652, 5,796,044, 5,760,341, 5,702,437, 5,676,694, 5,584,873, 5,522,875, 5,423,881, 5,411,545, 5,354,327, 5,336,254, 5,336,253, 5,324,321, 5,303,704, 5,238,006, 5,217,027, and 5,007,435, the entire disclosure of each which is hereby incorporated by reference into this specification. Because these devices are coated with nanomagnetic particles, they are resistant to electromagnetic radiation.

In one embodiment, one or more of the coating constructs are used to coat a multiple discontinuously shielded conductor assembly that is comprised of a multiplicity of shielded conductors each of which is coated discontinuously or continuously with nanomagnetic shielding. The centrally disposed conductor is preferably a pacing lead, and the other shielded conductors are preferably cardioversion defibrillation leads. In the embodiment depicted, the entire assembly is shielded with a layer of nanomagnetic material. As will be apparent, the use of discontinuous coating enables the multiple conductors to make electrical contact at one or more points along their axial dimension, to provide redundant electrical channels, in the event one channel should break. The discontinuous coating provides reduced exposure to externally applied electromagnetic fields. The discontinuous shield may be; intermittingly discontinuous along its axial dimension, discontinuous at its proximal end, or discontinuous along its distal end. It is to be understood that the discontinuous shield may be applied to any of the conductor or lead configurations described above.

By way of further illustration, one may use one or more of the coating constructs of this invention to coat a multi-conductor lead connected to a catheter and a sheath. This assembly is similar to the assembly depicted in U.S. Pat. No. 6,178,355, the entire disclosure of which is hereby incorporated by reference into this specification, but differs therefrom in that the use of nanomagnetic particle shielding provides resistance to electromagnetic radiation.

Thus, by way of further illustration, the coating constructs illustrated in FIGS. 6A through 6E may be used in the lead designs shown in U.S. Pat. Nos. 6,285,910, 6,178,355, 6,119,042, 6,061,598, 6,018,683, 5,968,086, 5,957,967, 5,954,759, 5,871,530, 5,676,694, the entire disclosure of each of which is hereby incorporated by reference into this specification.

In one embodiment, the coating constructs are used to prepare a discontinuously shielded conductor similar to the assembly depicted in FIG. 1 of U.S. Pat. No. 6,016,436. The entire disclosure of this patent is hereby incorporated by reference into this specification.

In one embodiment, the coated substrate is a lead body that carries at its distal end an insulative electrode head which may be fabricated of a relatively rigid biocompatible plastic, such as a polyurethane; the electrode head carries an advanceable helical electrode. At its proximal end, the lead carries a trifurcated connector assembly provided with two connector pins each coupled to one of two elongated defibrillation electrode coils.

In one embodiment, a coated substrate is produced in which the coating is intermittingly discontinuous along its axial dimension, to enable for example direct stimulation and sensing of tissues and organs, while providing for example, reduced exposure to an externally applied electromagnetic field. Reference may be had, e.g., to the lead designs shown in U.S. Pat. Nos. 6,289,251, 6,285,910, 6,119,042, 6,066,166, 6,061,598, 6,038,463, 6,018,683, 5,957,970, 5,957,967, 5,935,159, 5,871,530, 5,702,437, 5,676,694, 5,584,873, 5,336,254, 5,336,253, 5,238,006, 5,217,027, the entire disclosure of each of which is hereby incorporated by reference into this specification. The conductor assemblies so modified are resistant to electromagnetic radiation.

In one embodiment, the layer of nanomagnetic material 135 is comprised of electrical circuitry.

One may use the nanomagnetic coating(s) used to shield electronic components located within leads. One may use these coatings to shield medical leads with stranded conductors similar to those depicted in U.S. Pat. No. 6,026,567, the entire disclosure of which is hereby incorporated by reference into this specification. In the embodiment depicted therein, the assembly is comprised of a ring electrode a core 254, a distal insulative sleeve a conductor, a lumen, cross bores, a distal portion and a point adjacent to a shoulder (but see FIGS. 2, 3, and 4 of U.S. Pat. No. 6,026,567).

One may use the coatings constructs to coat a guidewire placed implantable lead with tip seal, such as that disclosed in U.S. Pat. No. 6,192,280 (the entire disclosure of which is hereby incorporated by reference into this specification). Such a lead is preferably comprised of an elongated insulative lead body, a laterally extending ridge, an internal conductive sleeve, a bore, a cup-shaped seal member, a plastic band, a controlled release device, an electrode, a distal tip, and a coiled conductor.

One may use the coating constructs to coat a catheter assembly that is similar to the catheter assembly disclosed in U.S. Pat. No. 6,144,882, the entire disclosure of which is hereby incorporated by reference into this specification.

By way of further illustration, one may use the coating constructs to coat conductor assemblies similar to those depicted in U.S. Pat. No. 5,935,159, the entire disclosure of which is hereby incorporated by reference into this specification. Thus, e.g., one may use the coatings to coat a medical electrical lead system having a torque transfer stylet assembly similar to the assembly depicted in U.S. Pat. No. 5,522,875, the entire disclosure of which is hereby incorporated by reference into this specification.

By way of yet further illustration, the coating constructs may be used to coat a stylet, similar to the stylet depicted in FIG. 7A of U.S. Pat. No. 5,522,875, supra.

In one embodiment, the coating constructs form a film with a thickness of about 100 nanometers or larger, and they produce an article with a specified modulus of elasticity (Young's Modulus). As is known to those skilled in the art, the modulus of elasticity is the ratio of the stress acting on a substance to the strain produced. In general, the nanomagnetic particle coatings and films produced by the process of this invention have a tensile modulus of elasticity of at least about $15 \times 10^6$ pounds per square inch.

The coating constructs may be used to coat a steerable wire. Steerable guide wires can be created, for example, by producing differential strain through tension wires electrically exciting piezoelectric elements. Each of these configurations is electrically conductive and susceptible to externally applied electromagnetic fields. The present invention preferably coats these elements with a nanomagnetic coating shield to protect these elements during magnetic resonance imaging-guided installation.

The coating constructs of this invention may be used to coat a transesophageal medical lead similar to the device depicted in U.S. Pat. No. 5,967,977 (see FIG. 1), the entire disclosure of which is hereby incorporated by reference into this specification.

The coating constructs of this invention may be used to coat a torque stylet used to activate a helix in a bent lead; see, e.g., U.S. Pat. No. 5,522,875. The entire disclosure of this United States patent is hereby incorporated by reference into this specification.

The coating constructs of this invention may be used to coat a sheath, in order to shield uncoated conductors positioned within the sheath. Multiple concentrically positioned sheaths are also used to provide additional protection of uncoated conductors positioned within the sheaths. In one embodiment, this sheath is constructed of a tube impregnated with nanomagnetic particles, or a braided wire mesh coated with nanomagnetic particles. In one embodiment, an internally positioned conductor is free to move, e.g., free to rotate or translate. In another embodiment, the motion of the active fixation electrode is controlled. By way of illustration, the shielded conductors described in FIG. 17A may be used in the lead designs illustrated in U.S. Pat. Nos. 6,289,251, 6,285,910, 6,192,280, 6,185,463, 6,178,355, 6,144,882, 6,119,042, 6,096,069, 6,066,166, 6,061,598, 6,040,369, 6,038,463, 6,026,567, 6,018,683, 6,016,436, 6,006,122, 5,999,858, 5,991,668, 5,968,087, 5,968,086, 5,967,977, 5,964,795, 5,957,970, 5,957,967, 5,957,965, 5,954,759, 5,948,015, 5,935,159, 5,897,585, 5,871,530, 5,871,528, 5,853,652, 5,796,044, 5,760,341, 5,702,437, 5,676,694, 5,584,873, 5,522,875, 5,423,881, 5,411,545, 5,354,327, 5,336,254, 5,336,253, 5,324,321, 5,303,704, 5,238,006, 5,217,027, and 5,007,435. The entire disclosure of each of these United States patent is hereby incorporated by reference into this specification.

The coating constructs disclosed in FIGS. 6A through 6E may be used to shield one or more medical devices and/or portions thereof, and, when so used, they provide a certain degree of shielding form the effects of electromagnetic radiation. They made be used in conjunction with auxiliary filter circuits which augment the shielding effects of the coating constructs.

Figure 7:
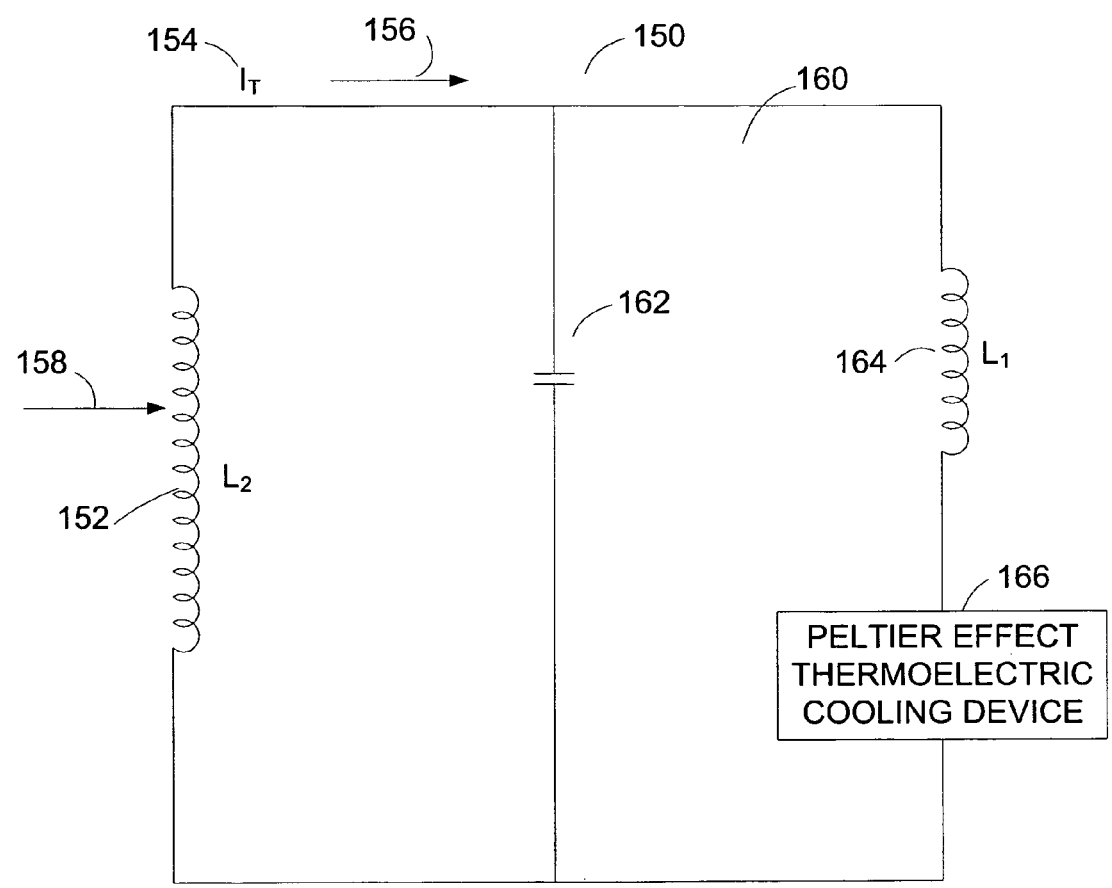
FIG. 7 is a schematic of circuit for cooling a substrate that is subjected to electromagnetic radiation.

One such filter circuit is illustrated in FIG. 7.

In the filter circuit 150 depicted in FIG. 7, a large coil 154 is chosen so that it generates a substantial amount of current 154 ($I_T$) when exposed to the high-frequency electromagnetic wave produced during the MRI process. This current 154 flows in the direction of arrow 156 supplies energy to the resonant circuit 160 defined by capacitor 162, inductor 164, and load 166.

In the embodiment depicted in FIG. 7, the load 166 is a thermoelectric cooling device. As is known to those skilled in the art, thermoelectric cooling is cooling based upon the Peltier effect. An electric current is sent to a thermocouple whose cold junction is thermally coupled to a substrate to be cooled, while the hot junction dissipates heat to the surroundings. In the Peltier effect, heat is absorbed when current is sent through a junction of two dissimilar metals. See, e.g., page 1917 of the McGraw-Hill Dictionary of Scientific and Technical Terms, Fourth Edition (McGraw-Hill Book Company, New York, N.Y., 1989).

Thermoelectric coolers are often used to maintain a constant temperature; see, e.g., U.S. Pat. Nos. 5,313,333, 4,628,277, 5,347,869, 6,4445,487, 5,956,569, 5,930,430, 5,717,804, 5,596,228, 5,561,685, 6,240,113, 6,107,6390, and the like.

By way of illustration and not limitation, U.S. Pat. No. 5,956,569 discloses an integrated thermoelectric cooler formed on the backside of a substrate. It appears that the device of this patent requires a direct current input; one may utilize an appropriate D.C. power supply adapted to convert the alternating current to the required direct current.

From the foregoing, it will be apparent that, for each of the electromagnetic radiations produced during an magnetic resonance imaging (MRI) process, one may utilize a series of energy-modifying devices to minimize the extent to which that particular electromagnetic radiation heats a particular substrate. One may convert much of the energy in the particular radiation into energy required to sustain a flywheel effect. One may absorb some of the energy (which will cause an increase in heat) and, with another portion of the energy, drive a thermoelectric cooler to cool the device, so that the neat heat change is zero.

One may combine one or more selective filtering devices together with the nanomagnetic shield of this invention to provide an assembly that is more effective in protecting against the adverse effects of high-frequency electromagnetic radiation that either device by itself. One such combined device is illustrated in FIG. 8.

Figure 8:
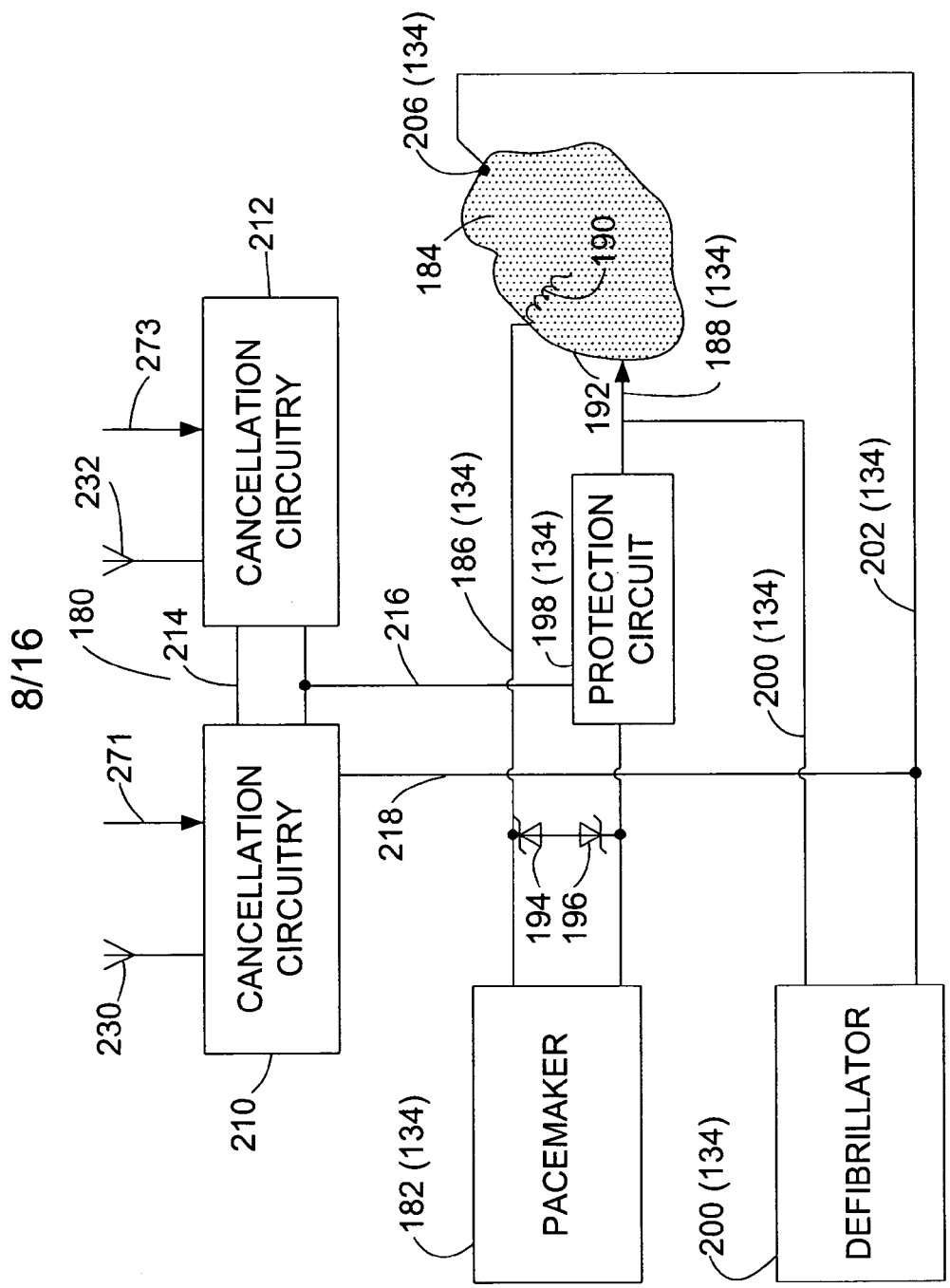
FIG. 8 is a schematic illustration of one preferred assembly for shielding cardiac tissue from the adverse effects of electromagnetic radiation.

FIG. 8 is a schematic of a magnetically shielded assembly 180 that is similar to the device depicted in FIG. 1 of U.S. Pat. No. 4,745,923. The entire disclosure of such U.S. Pat. No. 4,745,923 is hereby incorporated by reference into this specification. This patent describes and claims: "An apparatus for protecting an implantable electrical device having a plurality of electrically conductive terminals, including output and return terminals and electrically conductive leads connected to said terminals against excessive currents comprising: means connected to form an electrically conductive low-impedance path for connection in circuit with at least one of said leads; means connected to form an electrically conductive high-impedance path for connection in circuit with said at least one lead; means for generating a signal representative of the current flowing in said low-impedance path; switch means for opening and closing said low-impedance path; and means responsive to said signal representative of said current for controlling said switch means to open said low-impedance path when said current exceeds a predetermined level so that said current flows in said high-impedance path, whereby the current flowing into said electrical device is limited to a safe level."

As is disclosed in U.S. Pat. No. 4,745,923, "The invention disclosed herein relates generally to protection devices used to protect other devices from damage or destruction resulting from voltage or current surges. In particular, the present invention relates to such a protection device which is implantable in the body of a patient with a heart pacemaker to protect the pacemaker against current surges, particularly those resulting from the operation of an external or implanted heart defibrillator."

"It is well known that in many instances an implanted heart pacemaker can successfully regulate the otherwise faulty operation of a damaged or diseased heart. Generally, a typical pacemaker senses electrical activity or lack of such activity in the heart muscle, and supplies electrical stimulus pulses to the heart to stimulate contractions when necessary. The electrical stimulus pulses generated by a pacemaker, however, are ineffective to stop the lethal condition of fibrillation. However, it is well known that the application of a series of high-voltage pulses to the heart is often effective in arresting fibrillation. Of course it is desirable following defibrillation of the heart for the pacemaker to resume its normal regulatory role. A serious problem in this regard, however, is that without adequate protection against the large current flow induced by the application of high-voltage defibrillation pulses to the heart, a pacemaker can be damaged or destroyed. Obviously, from the standpoint of the patient's continued well being, this is a totally unacceptable consequence."

"In the past, a number of attempts have been made to provide adequate protection against excessive currents and voltages for pacemakers and other medical devices such as electrocardiogram (ECG) amplifiers. For example, it is known to connect one or more zener diodes between the opposite leads of a pacemaker to limit the voltage differential therebetween."

"However, as discussed in U.S. Pat. No. 4,320,763 to Money, this approach is not effective to limit the current flow between the heart tissue and the electrode at the distal end of the pacemaker lead. As a result, the heart tissue near the point of contact with the electrode can be severely damaged when high-voltage defibrillation pulses are applied to the heart. The U.S. Pat. No. 4,320,763 discloses that such tissue damage can be prevented by connecting a current limiting device such as a diode or a pair of field effect transistors (FETs) in series between a pacemaker output terminal and a distal electrode. However, it is apparent that the current limiting device thereby becomes a permanent part of the pacemaker circuit. When current limiting is not needed, for example during normal pacing operation, it is desirable to remove the current limiting device from the circuit to avoid unnecessary noise generation as well as loading effects."

"An approach for protecting the pacemaker circuitry itself is disclosed in U.S. Pat. No. 4,440,172 to Langer. The U.S. Pat. No. 4,440,172 discloses an implantable pacemaker and defibrillator unit in which the pacemaker and defibrillator share common output and return lines. The pacemaker generates negative-going stimulus pulses and is protected against the positive-going high-voltage defibrillator pulses by a resistor and forward biased diode connected in series between the common output line and ground. This approach only provides limited protection to the pacemaker from unidirectional defibrillation pulses. Recent medical research has shown, however, that a number of benefits are obtained by using a bidirectional or "biphasic" pulse train to defibrillate the heart. Some of the benefits of "biphasic" defibrillation, which forms no part of the present invention, are discussed in Schuder, Defibrillation of 100 kg Calves With Asymmetrical, Bidirectional, Rectangular Pulses, Cardiovascular Research 419–426 (1984), and Jones, Decreased Defibrillator-Induced Dysfunction With Biphasic Rectangular Waveforms, Am. J. Physiol. 247 (Heart Circ. Physiol. 16): H792–H796 (1984)."

" . . . the present invention has as an object to provide a protection device that protects both a pacemaker or other implantable device and the heart tissue near a lead thereof against damage from high current and voltage levels . . . ."

Referring again to FIG. 8, and in the preferred embodiment depicted therein, a heart pacemaker 182 implanted in the body of a patient is electrically connected in circuit with the patient's heart 184 via conventional electrically conductive pacing/sensing and return leads 186/188. Pacing/sensing lead 186 contains an electrically conductive barbed or screw-shaped pacing/sensing electrode 190 at its distal end for making firm electrical contact with the heart 184. Return lead 188 contains at its distal end a conductive patch 192 which may be sewn to the wall of the heart 184 to ensure a solid electrical connection. Electrically connected between the pacing/sensing and return leads 186,188 are oppositely polled first and second zener diodes 194, 196 to limit the voltage differential between the terminals of the pacemaker 182. First zener diode 194 preferably limits the positive voltage differential to approximately +3 v. Second zener diode 196 preferably limits the negative differential to approximately −10 v. A protection circuit 198 is implanted with the pacemaker 182 and is electrically connected in series with return lead 188 and patch 192 between the heart 184 and the pacemaker 182.

In addition, a defibrillator 200, which may be either an external or an implanted unit, is also electrically connected in circuit with the heart 184. If implanted, the defibrillator 200 is electrically connected to the heart 184 via conventional electrically conductive output and return leads 202, 204. Output lead 202 has attached to its distal end a conductive patch 206 which may be sewn to the wall of the heart 184. In this embodiment, return lead 204 is electrically connected at its distal end by any suitable means to return lead 188 between the heart 184 and the protection circuit 198 so that the pacemaker 182 and the defibrillator 200 share a common return lead to some extent. Of course, if the defibrillator 200 is an external unit, then no direct connections to the heart 184 are present. Instead, electrically conductive paddles of a type well known to those skilled in the art are supplied externally to the chest of a patient in the vicinity of the heart 184 as output and return electrodes.

The pacemaker 182 and defibrillator 200 described above are exemplary devices only and that the protection circuit 198 comprising a presently preferred embodiment of the present invention will find use in many other applications where protection of a device against high voltages and currents is desirable.

As is illustrated in FIG. 2 of U.S. Pat. No. 4,745,923 (the entire disclosure of which is hereby incorporated by reference into this specification), the protection circuit 16 is electrically connected to conductive patch 15 via return lead 13. In series with return lead 13 are a first and a second field effect transistor (FET) 22, 23 and a 5 ohm sensing resistor 24. The drain of the second FET 23 connects to return lead 13 on the heart 11 side. The source of the second FET 23 connects to one end of the sensing resistor 24 and the source of the first FET 22 connects to the opposite end. The drain of the first FET 16 connects to the opposite end of return lead 13 on the pacemaker 10 side. The gates of the first and second FETs 22,23 are connected in parallel to one end of a 390 K ohm current limiting resistor 29 and to the collectors of first and second parallel bipolar transistors 25,26. The other end of the 390 K ohm current limiting resistor 29 connects to a DC voltage source 30.

In one preferred embodiment, illustrated in FIG. 8, one or more of the pacemaker 182, the defibrillator 200, the leads 186 and 188, the protection circuit 198, the leads 202 and 204, and the patches 192 and 206 are coated with film 134 of nanomagnetic material. This is indicated by the use of "(134)" after the element in question. Thus, e.g., "186(134)" indicates that lead 186 is coated with nanomagnetic film 134.

In this preferred embodiment, the film 134 that is disposed about one or more of the components of the assembly 180 is preferably comprised of at least about 30 weight percent of nanomagnetic material with a mass density of at least about 0.01 grams per cubic centimeter, a saturation magnetization of from about 1 to about 36,000 Gauss, a coercive force of from about 0.01 to about 5,000 Oersteds, a relative magnetic permeability of from about 1 to about 500,000, and an average particle size of less than about 100 nanometers.

U.S. Pat. No. 4,745,923 discloses but one type of current-limiting protection circuit that may be used in the assembly 180 of FIG. 8. One may use other such protection circuits disclosed in the prior art.

Thus, by way of illustration and not limitation, U.S. Pat. No. 4,320,763 discloses a device for preventing tissue damage when high-currents flow through the tissue as a result of high voltage differentials. The patent claims: "In a pacemaker assembly comprising pulse-generator means for generating electrical pulses and electrode means having a proximal end coupled to said pulse-generating means and a distal end designed to be placed adjacent to body tissue for delivering said pulses to said tissue, the improvement comprising: current-limiting means coupled in series with said pulse-generating means and said electrode means for permitting passage of said electrical pulses to said tissue and for protecting said tissue against tissue damaging current flow between said distal end of said electrode means and said tissue as may occur with cardioversion."

"The object of the invention claimed in U.S. Pat. No. 4,320,763 was set forth in column 1 of the patent, wherein it was stated that: "It is therefore an object of the present invention to protect the heart tissue of a pacemaker implantee form damage upon application of high voltages to the users body." The entire disclosure of this United States patent is hereby incorporated by reference into this specification.

By way of further illustration, U.S. Pat. No. 5,197,468 discloses a "device for protecting an electronic prosthesis from adverse effects of RF . . . energy." This device includes " . . . a Ferrite body electrically and thermally connected to the lead wire and to a ground element." In particular, U.S. Pat. No. 5,197,468 discloses and claims: "an electronic prosthesis that is implantable into a user's body including:
A) an electronic device that is implantable into a user's body and includes a dc power source, electronic control elements, tissue stimulating elements and an electronic lead wire electrically connecting said power source, said electronic control elements and said tissue stimulating elements; and B) a protective device for protecting said electronic device from undesired RF energy induced operation and from undesired electrostatic energy induced operation, said protective device including (1) a ground element having a first impedance and electrically separated from said lead wire be said first impedance, and (2) an impedance element in said lead wire connected between said dc power source and said tissue stimulating elements having an impedance that is greater than said first impedance when exposed to RF energy." The entire disclosure of this United States patent is hereby incorporated by reference into this specification.

As is disclosed in column 3 of U.S. Pat. No. 5,197,468, " . . . such external influences as RF energy . . . have been identified as causing problems with artificial cardiac pacers . . . . The literature is replete with examples of cardiac pacer malfunctions traced to . . . MRI techniques . . . . "

By way of further illustration, U.S. Pat. No. 5,584,870 discloses a device for protecting a cochlear implant from external electrostatic charges. The entire disclosure of this United States patent is hereby incorporated by reference into this specification.

By way of further illustration, U.S. Pat. No. 5,833,710 provides a device for protecting cardiac tissue near low energy implanted electrodes; the entire disclosure of this United States patent is hereby incorporated by reference into this specification. There is disclosed and claimed in this patent: "An implantable medical device comprising: an electronic circuit operable to provide low energy cardiac tissue stimulation and detection and at least two inputs to receive respectively, at least two low energy stimulation and detection electrodes, wherein the electronic circuitry has a reference potential as a system ground which is isolated from an earth ground; and an automatic, unidirectional current limiting circuit interposed in series between said electronic circuitry and each input and coupled to said reference potential, said automatic unidirectional current limiting circuitry having a protected output connected to said electronic circuitry and an unprotected input."

As is disclosed in column 3 of U.S. Pat. No. 5,833,710, " . . . the present invention pertains to protecting the circuitry connected to the low energy leads, and protecting the patient's tissue at the low energy lead sites, from the high energy pulses . . . and from high energy pulses from other medical electronic devices . . . . "

By way of yet further illustration, U.S. Pat. No. 5,591,218 describes a "current limiter for implantable electronic device lead" which, like the device of U.S. Pat. No. 5,833,710, " . . . protects cardiac tissue near the low energy electrodes" (see the abstract); the entire disclosure of this U.S. Pat. No. 5,591,218 is hereby incorporated by reference into this specification. This patent discloses and claims: "A unidirectional current limiting circuit for use in series with the lead of an implanted medical device having low energy stimulation and detection electrodes, comprising: an unprotected input and a protected output; a current flow from the unprotected input to the protected output; a reference potential corresponding to a ground potential; a bias voltage; a first switch having an open circuit condition, a current limiting condition, and a closed circuit condition, the first switch having an input connected to the unprotected input and an output; a low value resistor connected to the output of the first switch producing a first voltage in response to said current flow through the first switch; a second switch having an open circuit condition and a closed circuit condition the second switch being operatively connected between the bias voltage and the protected output; a voltage divider connected to the unprotected input and the protected output, said voltage provider and producing a control voltage corresponding to a voltage across the unprotected input and the protected output; and a voltage clamp circuit connected between the reference potential and the protected output and operable to maintain the protected output voltage within a preset voltage range of the reference voltage; wherein the first switch is biased in the closed circuit condition when the voltage of the low value resistor is below the bias voltage by a first predetermined amount, the first switch is biased in the current limiting condition when the voltage of the low value resistor is not below the bias voltage by the first predetermined amount, and wherein the second switch is automatically biased in the open circuit condition when the control voltage is less than a second predetermined amount and in the closed circuit condition when the control voltage is greater than the second predetermined amount, the second switch closed circuit condition effectively lowering the bias voltage to place and maintain the first switch in the open circuit condition."

By way of yet further illustration, one may use the "current limiter for an implantable cardiac device disclosed in U.S. Pat. No. 6,161,040, the entire disclosure of which is hereby incorporated by reference into this specification. This patent describes and claims: "A defibrillator for implantation into a patient to provide therapy to a patient's heart, comprising: a pulse generator generating selectively defibrillation pulses, said defibrillation pulses having positive and negative phases; defibrillator electrodes for delivering said defibrillation pulses to said heart; first and sensing electrodes extending to said heart; a sensing circuit sensing intrinsic activity within said heart; and a protection circuit arranged between sensing electrodes and said sensing circuit to protect said sensing circuit from an overvoltage resulting from said defibrillation pulses, said protection circuit including a first section and a second section; wherein said first section and a second section each include an electronic element arranged to limit current during said positive phase and said negative, respectively; and a biasing circuit disposed in said protection circuit and shared by said first and second sections for biasing said electronic elements." As is disclosed in column 1 of U.S. Pat. No. 6,161,040, " . . . because the impedance of the heart tissues through which the shocks are discharged are unknown, it is difficult to control the current delivered through the shocks. Abnormally high current levels are undesirable because a high current may damage the heart tissues."

Referring again to FIG. 8, and in the preferred embodiment depicted therein, it will be seen that the assembly 180 is comprised of one or more cancellation circuits 210 and/or 212. These cancellation circuits 210,212, in one embodiment, are not connected to any other circuitry or device. Alternatively, the circuits 210/212 may be connected to each other (via line 214) and/or to the protection circuit 198 (via line 216) and/or to lines 186, and/or 202 and/or 204 (via line 218), and/or to defibrillator 206 and/or to heart 184. Other possible circuit arrangements will be apparent to those skilled in the art.

The cancellation circuits 210 and 212 preferably minimize the effects of high frequency electromagnetic radiation by the mechanism of cancellation. Cancellation is the elimination of one quantity by another, as when a voltage is reduced to zero by another voltage of equal magnitude and opposite sign. See, e.g., page 91 of Stan Gibilisco's "The Illustrated Dictionary of Electronics," Sixth Edition (Tab Books, Blue Ridge Summit, Pa., 1994).

One may use one or more of the cancellation circuits disclosed in the prior art, or variations thereof especially adapted to cancel the high-frequency electromagnetic waves present in a biological organism during MRI analyses. Some of these prior art cancellation circuits are discussed below.

U.S. Pat. No. 3,720,941 discloses a clutter cancellation circuit used in a monopulse radar system. This clutter cancellation circuit comprises: a means for deriving first and second signals respectively indicative of first and second reception lobe responses of a monopulse antenna; first and second channels respectively coupled to said first and second signals; signal combining means for algebraically combining the signals in said first and second channels, for providing a difference signal indicative of the algebraic difference of the signals in the said first and second channels, whereby a clutter cancelled output is provided when the phase and amplitude differences between the signals in said first and second channels are nulled; phase shifting means connected in series in said first channel for nulling the phase difference of the signals in said first and second channels; and amplitude adjusting means connected in said first channel for nulling the amplitude difference between the signals in said first and second channels." The entire disclosure of this United States patent is hereby incorporated by reference into this specification.

U.S. Pat. No. 3,935,533 discloses a microwave transceiver comprised of a cancellation circuit. As is disclosed in claim 1 of this patent, the single oscillator microwave receiver comprises: "antenna means for transmitting and receiving microwave energy; means for coupling energy from said oscillator to said antenna means for transmission thereby, and for simultaneously coupling energy received at said antenna means and a small portion of the energy of said oscillator in mixed fashion to the input of said FM receiver; an AFC circuit connected to the output of said FM receiver; means for providing a substantially DC voltage suitable for controlling the carrier frequency of said microwave oscillator; summing means, the output of said summing means being connected to said frequency-controlling voltage input of said microwave oscillator; input means for applying transmitter input modulation to one input of said summing means; and first selectively operable means for connecting said AFC circuit or carrier voltage means to a second input of said summing means, alternatively, whereby said microwave oscillator provides a carrier frequency selectively determined by said AFC circuit or by said carrier voltage means, which is frequency modulated in accordance with said transmitter input modulation; wherein said input means includes a variable gain amplifier having a signal input and a gain control input, said signal input being connected to transmitter input modulation, the output of said variable gain amplifier being connected to the first input of said summing means; delay means responsive to transmitter input modulation for providing delayed transmitter input modulation which is delayed by a period of time substantially equal to the circuit signal propagation time from the input of said variable gain amplifier through said FM receiver; second selectively operable means responsive to the output of said FM receiver and to the output of said delay means for selectively combining said delayed transmitter input modulation with the output of said FM receiver in a voltage polarity relationship to provide a receiver output signal having transmitter input modulation substantially cancelled therefrom; and means responsive to said receiver output signal and to said delayed transmitter input modulation for providing a gain control signal to the gain control input of said variable gain amplifier, said gain control signal adjusting the gain of said variable gain amplifier so that the magnitude of transmitter input modulation included in the output of said FM receiver is adjusted with respect to the magnitude of delayed transmitter input modulation provided by said delay unit so that the transmitter input modulation in said receiver output signal is substantially nulled to zero." The entire disclosure of this United States patent is hereby incorporated by reference into this specification."

U.S. Pat. No. 4,535,476 an offset geometry, interference canceling receiver that comprises: antenna means for receiving signals from a desired signal source and from an interference signal source located adjacent to the desired signal source, said antenna means comprising a main feedhorn which is focused on said desired signal source and an auxiliary feedhorn which is focused on said interference signal source, the antenna means being responsive to signals from the desired signal source for generating a composite signal including a desired message signal and a first interference signal, the antenna means also being responsive to signals from the interference signal source for generating a second interference signal comprising the first interference signal, combining means including a first feedback control circuit responsive to a representation of the desired message signal for generating appropriate control signals to cause variations of the phase and amplitude of the first interference signal, means responsive to the control signals for adjusting the phase and amplitude of the first interference signal, and a combiner for combining the adjusted first interference signal with the composite signal to generate said representation of the desired message signal, and signal translation means including a first duplexer coupled to the antenna means for interfacing the composite signal received therefrom, a first amplifier means for adjusting the amplitude of the composite signal to a predetermined level, a second duplexer coupled to the antenna means for interfacing the second interference signal received therefrom, and a second amplifier means for adjusting the amplitude of the second interference signal to a predetermined level. The entire disclosure of this United States patent is hereby incorporated by reference into this specification.

U.S. Pat. No. 4,698,634 discloses a subsurface insection radar signal comprised of a clutter cancellation circuit. As is disclosed in claim 1 of this patent, the clutter cancellation circuit is comprised of " . . . clutter cancellation means operatively connected to said receiver means for eliminating internal reflections developed in said system to prevent interference by said internal reflections with the desired external reflections to enhance the system detection capability and reliability of evaluation of said external reflections, said internal reflections comprising signals generated within said system by said antenna means, said transmitter means and said receiver means." The entire disclosure of this United States patent application is hereby incorporated by reference into this specification.

U.S. Pat. No. 5,280,290 discloses a self-oscillating mixer circuit that comprises "cancellation means for combining the IF signal with the modulating signal to cancel from the IF signal a modulation corresponding to that of the modulated RF signal, said cancellation means including a first input coupled to the output of the mixer, a second input for receiving the modulating signal, and an output for producing a demodulated signal." The entire disclosure of this United States patent is hereby incorporated by reference into this specification.

U.S. Pat. No. 5,407,027 also discloses a " . . . cancellation circuit for canceling offset voltage by storing, when said inverter is stopped while said current command generating circuit keeps generating the current command value, the output signal of said current detector, and by adding, when the inverter is in operation, the stored output signal to the present output signal of the current detector." The entire disclosure of this United States patent is hereby incorporated by reference into this specification.

U.S. Pat. No. 6,008,760 discloses a cancellation system for frequency reuse in microwave communications. This patent discloses and claims: ". A free-space electromagnetic wave communications system for canceling co-channel interference and transmit signal leakage, said communications system transmitting a plurality of signals from at least one transmit location to at least one receive location, said communications system utilizing spatial gain distribution processing of the transmitted signals for providing frequency-reuse of the transmitted signals, utilizing distributed frequency compensation for compensating for frequency dependent variations of transmitted and received antenna beam patterns, utilizing interferometric beam-shaping for controlling beamwidth of antenna beam patterns, and utilizing interference cancellation for reducing transmit signal leakage in received signals, said communications system comprising: a signal transmitter located at the transmit location for transmitting a plurality of transmission signals, each of said transmission signals having a predetermined spatial gain distribution at the receive location, an antenna array comprising a plurality of spatially-separated antenna elements located at the receive location, each of said antenna elements being responsive to at least one of said transmission signals for generating a desired receive communications signal and being responsive to one or more said transmission signals for generating a noise signal, a cancellation circuit coupled to each of said plurality of antenna elements for receiving said desired communications signals and said noise signals, said cancellation circuit providing weights to said desired communications signals and said noise signals wherein said weights are determined from said spatial gain distribution of said transmission signals, said cancellation circuit combining said weighted noise and desired communications signals for canceling said noise signals, thereby separating said communications signals from said noise signals, an excitation means coupled to said antenna elements for generating a predetermined distribution of excitation signals to electrically excite said antenna elements for producing a predetermined beam pattern, the excitation signals having distributed frequency characteristics, a transmit beam-shaping processor coupled to said excitation means for providing a frequency-dependent weight distribution to the excitation signals with respect to signal frequency such that a plurality of frequency-dependent beam patterns is generated by said array, each of the beam patterns corresponding to one of a plurality of different excitation signal frequencies, the beam patterns being substantially equal within a predetermined spatial region, a receiver coupled to said antenna elements for providing a predetermined weight distribution to the receive signals, the weighted receive signals being summed to provide a beam pattern that indicates responsiveness to the incident radiation with respect to an angle of incidence of the incident radiation, a receive beam-shaping processor coupled to said antenna elements for providing a frequency-dependent weight distribution to the receive signals with respect to receive signal frequency to produce a plurality of frequency-dependent beam patterns, each of the beam patterns corresponding to one of a plurality of different receive signal frequencies, the beam patterns being substantially equal within a predetermined spatial region, an interferometric receive beam-shaping processor coupled to said receiver for providing a plurality of weight distributions to the receive signals for providing a plurality of interfering receive beam patterns, the receive beam patterns being combined to produce a combined interferometric receive beam pattern, the combined interferometric receive beam pattern providing a predetermined receiver response in at least one direction, an interferometric transmit beam-shaping processor coupled to said excitation means for providing a plurality of weight distributions to the excitation signals for providing a plurality of interfering transmit beam patterns, the beam patterns being combined to produce a combined interferometric transmit beam pattern, the combined interferometric transmit beam pattern providing a predetermined transmit signal profile in at least one direction, and an isolator circuit coupled between said excitation means, said antenna array, and said receiver, for electrically isolating said receiver from said excitation means, said isolator circuit comprising: an active branch, said active branch comprising an active reference branch coupled to a splitting circuit for receiving a reference signal, and a transmit branch, said transmit branch comprising a transmit input port for receiving an input transmit signal, a splitting circuit coupled to the input port for splitting the input transmit signal into an output transmit signal and a reference signal, and an output transmit port coupled to an antenna for conducting the output transmit signal to the antenna, a reference sensing element coupled to said active reference branch, said reference sensing element being responsive to the reference signal in said active reference branch, a transmit sensing element coupled to said transmit branch, said transmit sensing element being responsive to the output transmit signal and a receive signal generated by said antenna in response to incident electromagnetic radiation, a combining circuit coupled to said reference sensing element and said transmit sensing element for combining the responses of said reference sensing element and said transmit sensing element for canceling the reference sensing element response to the reference signal and the transmit sensing element response to the output transmit signal, said combining circuit having an output port for coupling the response of said transmit sensing element to the receive signal to a receiver, a passive reference branch coupled to said splitting circuit for receiving the second reference signal, said passive reference branch comprising a reference splitting circuit coupled to a dummy reference branch and a dummy antenna branch, said reference splitting circuit splitting the second reference signal into a dummy reference branch signal and a dummy transmit signal, the dummy reference branch signal being coupled into said dummy reference branch, said dummy reference branch having a complex impedance that is proportional to the complex impedance of said active reference branch, and the dummy transmit signal being coupled into said dummy antenna branch, said dummy antenna branch comprising a variable impedance element, said dummy antenna branch having an impedance that is proportional to the impedance of said transmit branch, an injection circuit coupled between said combining circuit and said dummy antenna branch for injecting the receive signal at the output port of said combining circuit into said second reference branch, a control-signal generator coupled to said active signal branch and said passive reference branch, said control-signal generator being responsive to electrical signals in said active signal branch and said passive reference branch for generating a difference signal therefrom, the difference signal representing differences in the proportion of the complex impedance of said active signal branch to the complex impedance of said passive reference branch, and an impedance controller coupled between said control-signal generator and said variable impedance element for receiving the difference signal and adjusting the impedance of said variable impedance element in order to minimize the difference signal." The entire disclosure of this United States patent is hereby incorporated by reference into this specification.

U.S. Pat. No. 6,211,671 discloses a cancellation circuit that removes interfering signals from desired signals in electrical systems having antennas or other electromagnetic pickup systems. This patent claims: An electromagnetic receiver system adapted to receive and separate at least one desired electromagnetic transmission signal from at least one interfering electromagnetic transmission signal, the receiver system including: a plurality of electromagnetic receivers adapted to be responsive to the at least one transmitted desired electromagnetic signal and the at least one transmitted interfering electromagnetic signal, the receivers generating a plurality of receive signals, each of the receive signals including at least one desired signal component and at least one interfering signal component, the receivers being spatially separated to receive different proportions of the at least one transmitted desired electromagnetic signal and the at least one transmitted interfering electromagnetic signal and a canceller coupled to the receivers adapted to process the receive signals, the canceller including an amplitude-adjustment circuit adapted to provide amplitude adjustment to at least one of the receive signals to compensate for amplitude differences between the at least one interfering signal component in each of a plurality of the receive signals resulting from at least one of a) differences in propagation of the at least one transmitted interfering signal to the plurality of electromagnetic receivers, and b) differences in the responsiveness of the electromagnetic receivers to the at least one transmitted interfering signal, the canceller including a phase-adjustment circuit adapted to provide phase adjustment to at least one of the receive signals to compensate for phase differences between the at least one interfering signal component in each of a plurality of the receive signals resulting from at least one of: a) differences in propagation of the at least one transmitted interfering signal to the plurality of electromagnetic receivers, and b) differences in the responsiveness of the electromagnetic receivers to the at least one transmitted interfering signal, the canceller adapted to combine the receive signals to separate at least one of the desired signal components by canceling at least one of the interfering signal components." The entire disclosure of this United States patent is hereby incorporated by reference into this specification.

U.S. Pat. No. 6,348,791 discloses an electromagnetic transceiver in which a cancellation circuit removes interfering signals. This patent claims: "1. An electromagnetic transceiver capable of simultaneously transmitting and receiving electromagnetic signals, the transceiver including: an antenna system capable of transmitting and receiving the electromagnetic signals, a signal transmitter coupled to the antenna system, the transmitter adapted to couple electromagnetic signals to the antenna system for transmission, a receiver coupled to the antenna system, the receiver adapted to be responsive to the transmitted electromagnetic signals and electromagnetic signals received by the antenna system, a cancellation circuit coupled to the transmitter and to the receiver, the cancellation circuit adapted to couple at least one cancellation signal to the receiver that reduces the responsiveness of the receiver to the transmitted signals, the cancellation circuit characterized by at least one of: an amplitude-adjustment circuit adapted to compensate for amplitude differences between the at least one cancellation signal and the receiver response to the transmitted signals resulting from at least one of: a) differences in propagation between the transmitted signals and the at least one cancellation signal to the receiver, and b) differences in the responsiveness of the receiver to the transmitted signals and the at least one cancellation signal, and a phase-adjustment circuit adapted to compensate for phase differences between the at least one cancellation signal and the receiver response to the transmitted signals resulting from at least one of: a) differences in propagation between the transmitted signals and the at least one cancellation signal to the receiver, and b) differences in the responsiveness of the receiver to the transmitted signals and the at least one cancellation signal." The entire disclosure of this United States patent is hereby incorporated by reference into this specification.

It will be apparent that not every component, or every circuit, or every device of these patents will be suitable for use in the cancellation circuitry 210 and/or the cancellation circuitry 212. What will also be apparent is that many of these components, devices, and circuits, and the principles on which they operate, will be suitable for use in cancellation circuitry 210,212, taking into account the high-frequency MRI electromagnetic waves such circuitry is designed to cancel and the goal of minimizing the amount of heat produced by such MRI electromagnetic waves. In particular, many of these components, devices, and/or circuits, and the principles on which they operate, will be suitable for modifying the current flow through biological tissue with which the medical device is contiguous or near to. Thus, in one embodiment, the applicants provide a magnetically shielded assembly comprised of a medical device implanted in a biological organism, wherein said medical device is disposed near biological tissue, wherein said magnetically shielded assembly is comprised of a nanomagnetic coating disposed on at least a portion of said medical device, wherein said magnetically shielded assembly is further comprised of means for limiting the flow of current through said biological tissue, and wherein said nanomagnetic coating has the properties described elsewhere in this specification.

Figure 9:
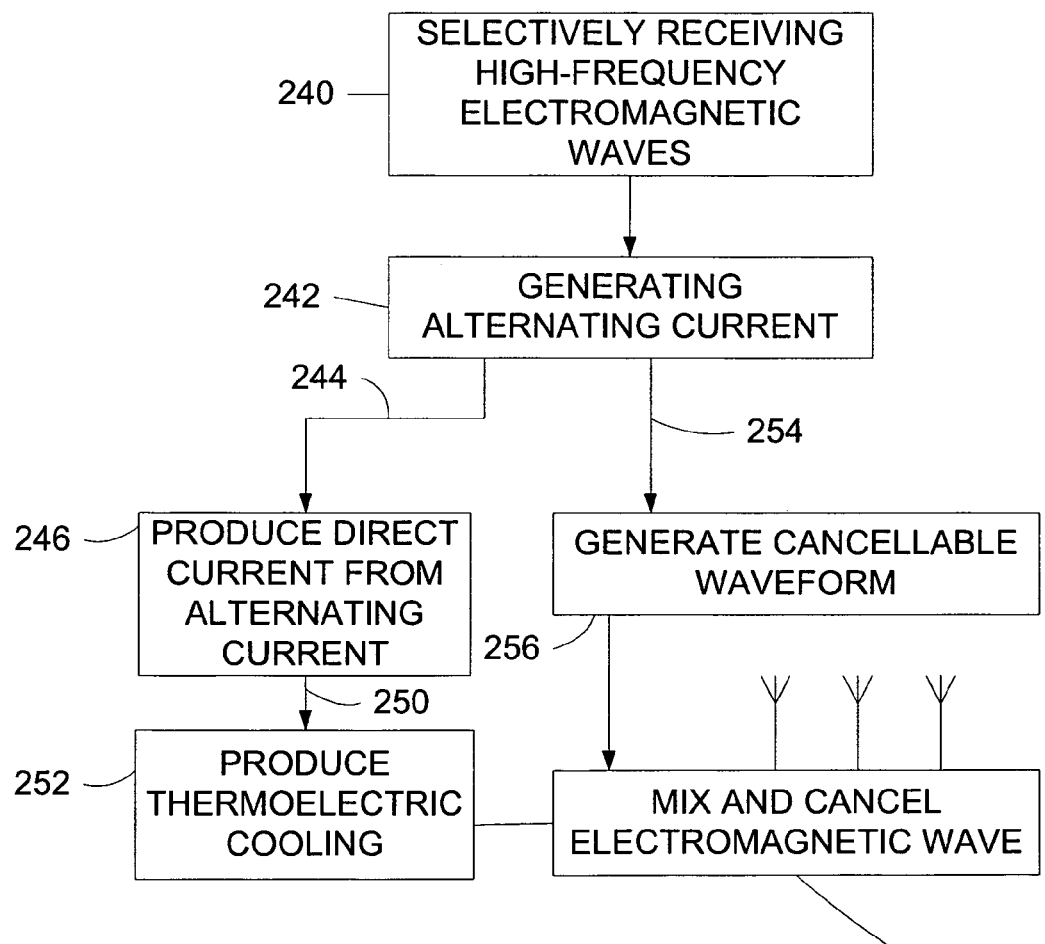
FIG. 9 is a flow diagram of a preferred process for shielding biological tissue from electromagnetic radiation.

In general, the cancellation circuitry 210,212, and the rest of the devices depicted in FIG. 8, will enable one to follow the process depicted in FIG. 9.

As will be apparent to those skilled in the art, there were many United States patents that disclosed cancellation circuits and/or means for limiting current flow that issued prior to the filing of this patent application. However, none of these prior art publications solved the very serious problem presented by MRI imaging of patients with implanted pacemakers.

Several publications refer to this serious problem. See, e.g., FDA Medical Device Report (MDR) records, in the FDA MDR database at www.FDA.gov, for reports of patient death during or after MRI examination. Reference also may be had to an article in the Feb. 22, 2002 edition of the Wall Street Journal. Reference also may be had to The Journal of the Tennessee Medical Association, 1988; 81(8): 523, Loss Prevention Case of the Month entitled "Not My Responsibility!" Additionally, reference may also be had to the publications discussed in the "Background of the invention" section of this specification.

Unlike the prior art devices, the assembly provided by the applicants is especially adapted to solve this problem. It provides a means for protecting biological tissue from the effects of heating comprising a conductor in contact with said biological tissue and forming an electrical circuit comprising said biological tissue, wherein said assembly is comprised of means for modifying the impedance of said electrical circuit such that, at a frequency of from about 20 megahertz to about 150 megahertz, such impedance is at least about 0.5 ohms per centimeter of length of said conductor, and wherein the assembly is comprised of means for limiting the flow of current through said tissue such that, when the assembly is exposed to an alternating current electromagnetic wave at a frequency of 64 megahertz and a magnetic field strength of from about 1.5 Tesla for at least about 15 minutes, the temperature of said biological tissue does not exceed 42 degrees Celsius. In another embodiment, under these conditions, the temperature of the biological tissue does not exceed 40 degrees. In yet another embodiment, under these conditions, the temperature of the biological tissue does not exceed 39 degrees.

In one embodiment, in this assembly, when the frequency of the MRI electromagnetic wave is from about 50 to about 70 megahertz, said impedance is at least about 2 ohms per centimeter of length of the conductor.

In one embodiment, in this assembly, the temperature rise of the biological tissue is controlled by a means for cooling the biological tissue.

FIG. 9 is a flow diagram illustrating one process of the instant invention. Referring to FIG. 9, and in step 240 thereof, the high-frequency electromagnetic waves produced during the MRI analyses are selectively received by the cancellation circuitry assemblies 210 and/or 212 by means of antennas 230 and 232. As is disclosed at page 110 of Stan Gibilisco's "Handbook of Radio and Wireless Technology," Sixth Edition, supra, " . . . an antenna is a . . . transducer . . . . A receiving antenna converts an electromagnetic field (EM) into an alternating current (AC)."

The antennas 232,232 are preferably tuned antennas that, with the appropriate combinations of antenna length, inductance, and/or capacitance, produce the maximum amount of AC current at the high frequencies produced during MRI analyses. Tuned antennas are well known to those skilled in the art. Reference may be had, e.g., to U.S. Pat. No. 6,310,346 (wavelength-tunable coupled antenna), U.S. Pat. No. 5,999,138 (switched diversity antenna system), U.S. Pat. No. 6,496,153 (magnetic-field sending antenna with RLC circuit), U.S. Pat. No. 5,614,917 (RF sail pumped tuned antenna), U.S. Pat. No. 5,528,251 (double tuned dipole antenna), U.S. Pat. Nos. 5,241,160, 5,231,355 (automatically tuned antenna), U.S. Pat. No. 4,984,296 (tuned radio apparatus), U.S. Pat. No. 4,739,516 (frequency tuned antenna assembly), U.S. Pat. Nos. 4,660,039, 4,450,588 4,280,129 (variable mutual inductance tuned antenna), U.S. Pat. Nos. 4,194,154, 3,571,716 (electronically tuned antenna), and the like. The entire disclosure of each of these United States patents is hereby incorporated by reference into this specification.

Referring again to FIG. 9, and in the preferred process depicted therein, in step 242, an alternating current is produced by the interaction of the antennas 230,232 with the high-frequency electromagnetic waves 273. This alternating current is then distributed to several different locations.

A portion of the alternating current is fed via line 244 to a power supply (not shown), which converts the alternating current to direct current in step 246. Thereafter, the direct current so produced is preferably fed via line 250 to a thermoelectric cooling assembly (such as the Peltier device cooling assembly 166 depicted in FIG. 7), and in step 252 thermoelectric cooling is produced.

Referring again to FIG. 9, another portion of the alternating current produced in step 242 is fed via 254 to a wave generator (not shown), and in step 256 a waveform is generated.

One may use, e.g., a conventional signal generator to produce the desired electromagnetic wave(s) in step 256. As is known to those skilled in the art, a signal generator is an instrument that delivers signals of precise frequency and amplitude, usually over a wide range. Reference may be had, e.g., to U.S. Pat. No. 6,256,157 (method for removing noise spikes), reissue 35,574 (method for acoustical echo cancellation), U.S. Pat. No. 5,126,681 (in-wire selective active cancellation system), U.S. Pat. No. 4,612,549 (interference canceller loop having automatic nulling of the loop phase shift for use in a reception system), U.S. Pat. No. 5,054,118 (balanced mixer using filters), U.S. Pat. No. 5,046,010 (fixed-echo canceling radio altimeter), U.S. Pat. No. 3,604, 947 (variable filter device), U.S. Pat. No. 5,950,119 (image-reject mixers), U.S. Pat. No. 4,520,475 (duplex communication transceiver with modulation cancellation), U.S. Pat. No. 5,131,032 (echo canceller), U.S. Pat. No. 6,169,912 (RF front end with signal cancellation), U.S. Pat. No. 6,114,983 (electronic counter measures in radar), U.S. Pat. No. 5,023, 620 (cross-polarization interference cancellation system), U.S. Pat. Nos. 5,924,024, 4,992,798 (interference canceller), U.S. Pat. No. 6,211,671 (interference-cancellation system for electromagnetic receivers), U.S. Pat. No. 6,208,135 (inductive noise cancellation for electromagnetic pickups), U.S. Pat. No. 6,269,165 (apparatus for reduction of unwanted feedback), U.S. Pat. No. 5,768,699 (amplifier with detuned test signal cancellation), U.S. Pat. No. 4,575,862 (cross-polarization distortion canceller), U.S. Pat. No. 6,147,576 (filter designs using parasitic and field effects), U.S. Pat. No. 4,438,530 (adaptive cross-polarization interference cancellation system), and the like. The entire disclosure of each of these United States patents is hereby incorporated by reference into this specification.

Referring again to FIG. 9, in step 256 one or more electromagnetic waves will be generated so that, when such wave(s) is mixed with the high-frequency electromagnetic waves produced by antennas 258, 260, and 262 in a mixer, some or all of such high-frequency electromagnetic waves will be cancelled.

Thus, as will be apparent, the process of FIG. 9 converts some of the high-frequency electromagnetic energy produced during MRI analyses to energy used for thermoelectric cooling (step 252), for conversion from alternating current to direct current (in step 246), for producing cancellable waveforms, and for mixing. All of this energy is energy that is not used to produce undesired heating of cardiac tissue.

Figure 10:
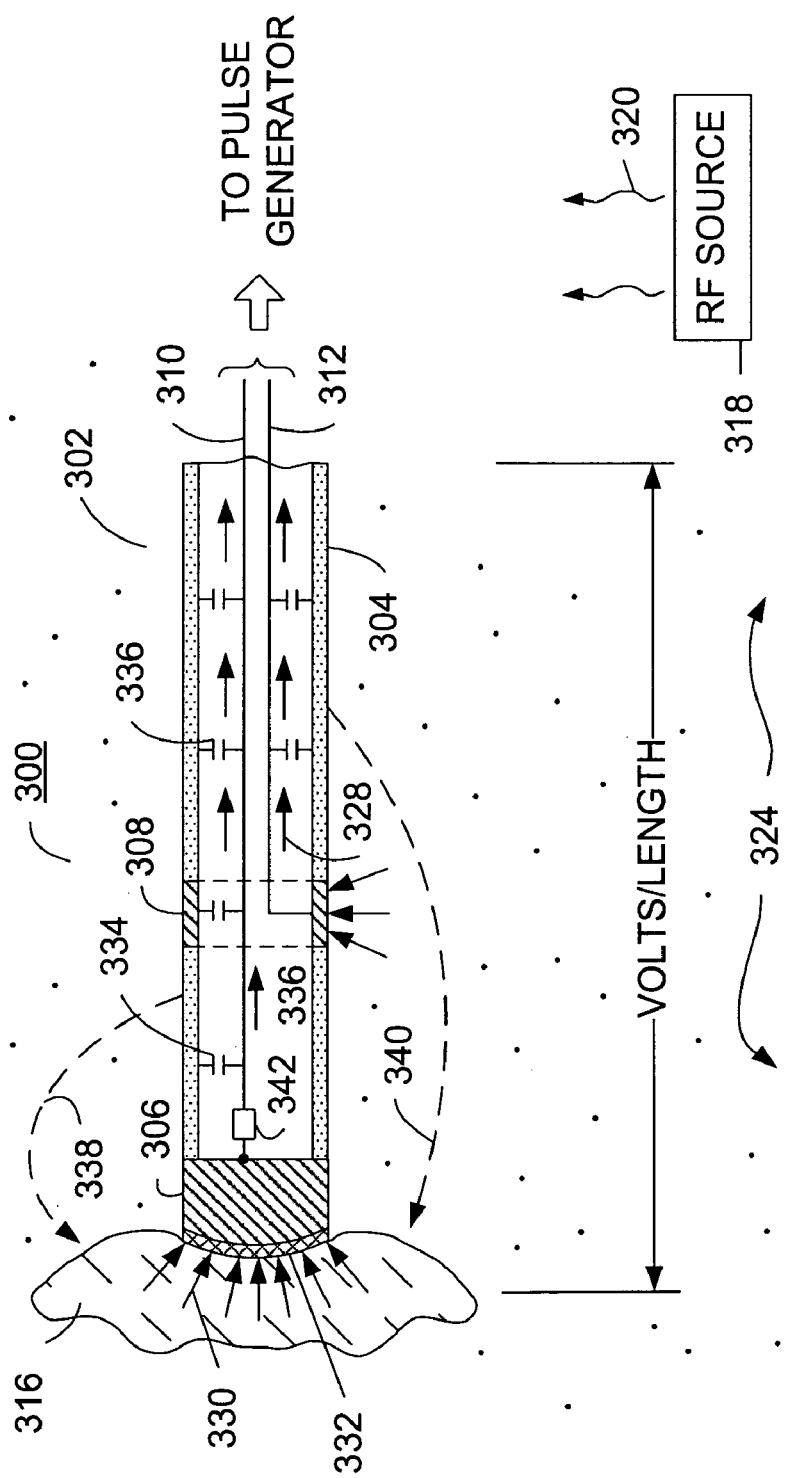
FIG. 10 is a schematic of one preferred assembly of the invention.

FIG. 10 is schematic view of an assembly 300 comprised an implanted electrical lead 302 that contains a catheter 304, electrodes 306 and 308, conductors 310 and 312, and a pulse generator (not shown). This assembly 300 provides another means for limiting the temperature rise in tissue 316 during MRI imaging.

Referring again to FIG. 10, and in the preferred embodiment depicted therein, the electrode 306 is contact with biological tissue 316. A source 318 of high frequency electromagnetic radiation 320, that preferably is at a frequency of from about 20 to about 150 megahertz and that has a field strength of from about 1 to about 100 microTesla induces a voltage 322 in tissue 324 that is from about 10 to about 1,000 volts per meter length of the tissue.

Without wishing to be bound to any particular theory, applicants believe that this potential difference induces a current flow 326/328 in leads 310 and 312. This current flow creates a high current density 330 at the interface 332 between the electrode 306 and the biological tissue 316. This high current density 330 creates heat at interface 332 that tends to damage the biological tissue 316.

It is believed that, in such a system 300, there is, effectively, a electrical circuit that includes an effective distributed capacitance network 334 which may comprise a multiplicity of effective capacitors 336. As will be apparent to those skilled in the art, there need not be actual capacitor elements in this system, but, at the specified frequency and field strength, the elements of the system act as capacitor network 334.

Referring again to FIG. 10, it is believed that current flows, in part, through paths 338 and 340.

Regardless of the actual mechanism of heat induction at interface 332, it has been found that the inclusion of a choke coil 342 in the system 300 reduces the temperature build up at interface 332 from a temperature rise of up to 20 degrees Celsius or more (when the choke coil is not present) to a temperature rise of only 1 degrees Celsius or less, when the system is exposed to radiation 320 for at least about 3 minutes.

Without wishing to be bound to any particular theory, applicants believe that the use of such a choke coil 342 increases the impedance of conductors 310, 312 such that this impedance is least about 0.5 ohms per centimeter of conductor length and, more preferably, at least about 2 ohms per centimeter of conductor length. This is one means of limiting the current through the biological tissue 316 which, in turn, limits the increase in temperature of the tissue 316; another such means is the thermoelectric cooling described elsewhere in this specification.

Without wishing to bound by any particular theory, applicants believe that the use of the choke coil 342 limits the current through the conductors 310 and 312, limits the current density 330 at electrode 306, and thus limits the temperature rise at interface 332.

Figure 11:
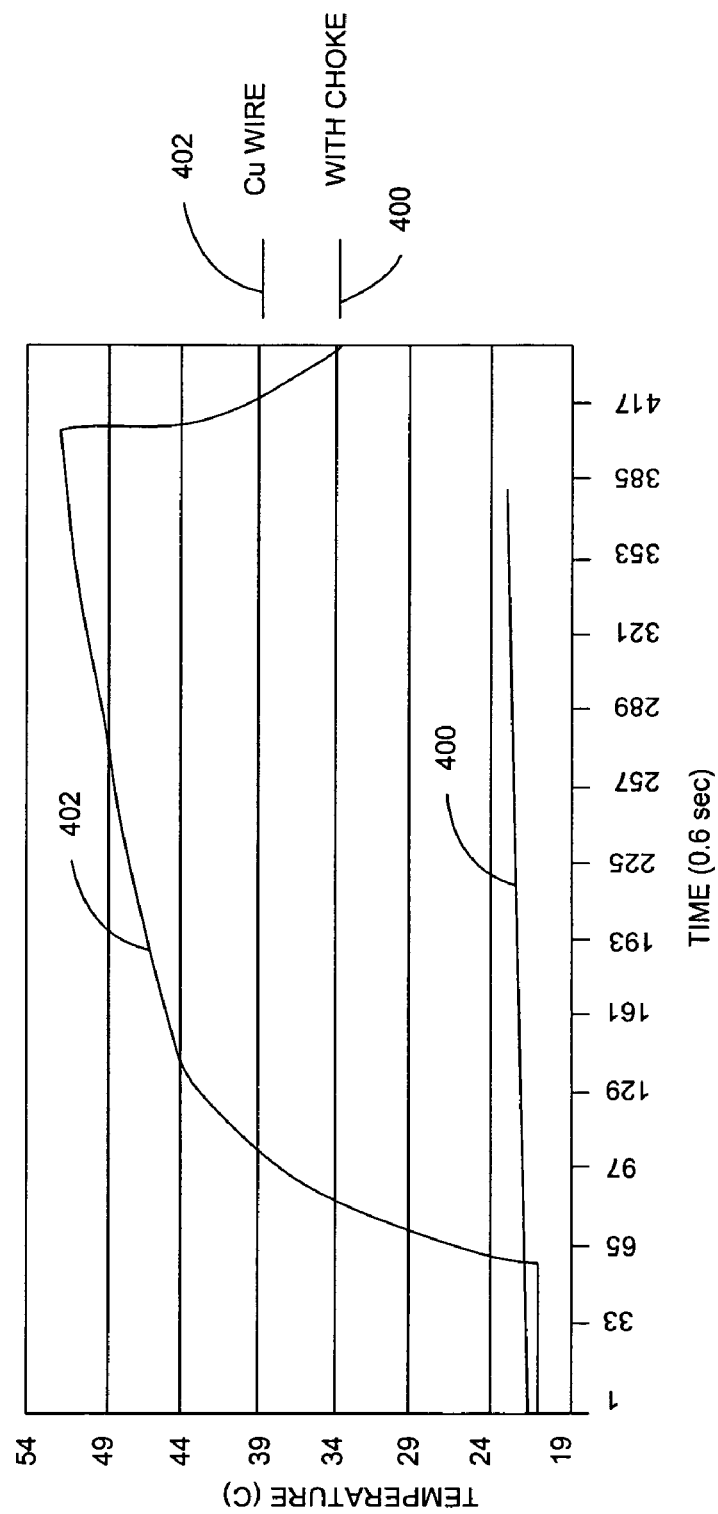
FIG. 11 is a graph illustrating the effects of the use of a choke coil in the assembly of FIG. 10.

FIG. 11 is a graph of the temperature response of two copper wires, one of which (wire 400) is connected to a choke coil, and the other of which (wire 402) is not subjected to a choke coil. As can be seen from this Figure, when both wires are subjected to an alternating electromagnetic field of 64 megahertz with a secondary static magnetic field strength of 1.5 Teslas for about seven minutes, the temperatures of both wires increases. However, the temperature rise in the wire 400 is substantially less than the temperature rise in wire 402.

Means for Limiting Induced Voltage

In prior art implantable devices, voltages that are induced during MRI imaging of patients with implanted pacemakers presented very serious problems. This MRI imaging often caused electromagnetic interference with cardiac pacing/sensing functions and inappropriate pacing of the heart (e.g. arrhythmias, incorrect inhibition/triggering, etc.), damage to the pulse generator, complete pacing failure, and serious risk to the patient including death. For reports of MRI-related deaths in patients with implanted leads see, e.g., FDA Medical Device Report (MDR) records, in the FDA MDR database at www.FDA.gov, for reports of patient death during or after MRI examination. Reference also may be had to an article in the Feb. 22, 2002 edition of the Wall Street Journal. Reference also may be had to The Journal of the Tennessee Medical Association, 1988; 81(8): 523, Loss Prevention Case of the Month entitled "Not My Responsibility!"

Many publications describe this and other problems associated with MRI imaging of patients with implanted pacemakers. See, e.g., an article by R. Boutin, et al., "Injuries associated with MRI: Survey of safety records and methods used to screen patients for metallic foreign bodies before imaging," AJR 1994: 162: 189–194.

Thus, the Food and Drug Administration considers the presence of a cardiac pacemaker a "strict contraindication" for patients referred for MR procedures. See, e.g., Food and Drug Administration, "Magnetic Resonance Diagnostics Device: Panel Recommendations and Report on Petitions for MR Reclassification," Federal Register 1988, 53.

It is known that sustained pacing inhibition is potentially catastrophic in pacemaker dependent patients. Depending on the duration of inhibition and emergence of escape rhythms, lightheadedness, syncope, or death could result. At high sensitivity levels (required to ensure detection of ventricular fibrillation), EMI induced prolonged inhibition and spurious tachyarrhythmia detection become likely.

It is also known that in vitro and in vivo animal studies show that application of 64 MHz RF power, required to produce MRI scans, can result in rapid pacing at pulses between 200 and 1,000 ms.

Induction of voltages and currents within a pacemaker-lead-myocardial loop can result in cardiac arrhythmias that yield cardiac outputs incompatible with sustaining life. Several cardiac pacemaker studies have shown human subjects to become tachyarrhythmic and/or hypotensive during MR studies. This mechanism seems to be the cause of death in some of the cardiac pacemaker patients that underwent MR procedures.

Time-varying MRI magnetic fields can induce voltage in leads (up to 20 volts in unipolar leads, much less in bipolar leads) that can pace the heart or interfere with sensing, and; very strong electromagnetic fields could induce voltage in the lead(s) that may directly capture the myocardium. For example, 58-kHz acoustomagnetic EAS (anti-theft) systems are capable of inducing 3.7 volts in pacemaker leads.

Figure 12:
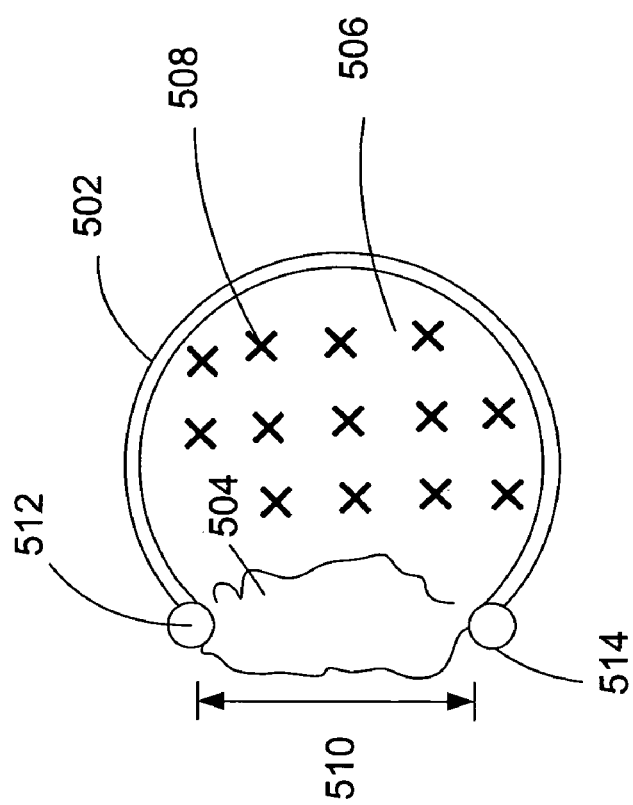
FIG. 12 is a schematic illustration of how a voltage is induced across a lead in contact with biological tissue when the lead is exposed to high frequency electromagnetic radiation.

FIG. 12 is a schematic representation the problem described above. Referring to FIG. 12, it will be seen that conductive lead 502 in contact with biological tissue 504 defines a cross sectional area 506 of from about 20 to about 40 square centimeters. The gradient field 508 present during MRI imaging generates a voltage 510 between electrodes 512 and 514 in accordance with Lenz' Law. In one embodiment, the magnitude of the induced voltage 510 is about 0.4 volts.

This induced voltage is sufficient to trigger undesirable biological reactions within the biological tissue 504. It is desired to reduce this induced voltage to a value of less than about 0.1 volts.

Figure 13:
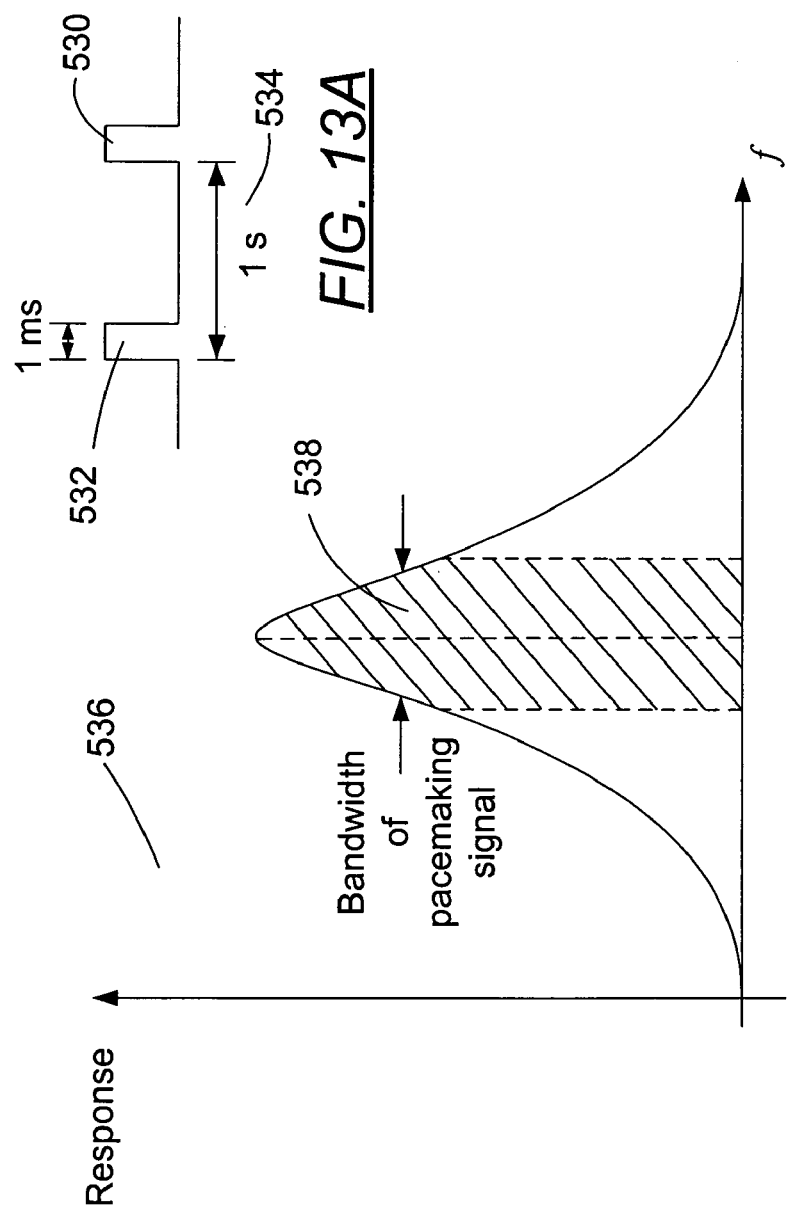
FIG. 13A is a schematic illustration of a pacemaker pacemaking waveform.
FIG. 13B is a graph of a frequency response curve for a band pass filter.

In one embodiment of the invention, depicted in FIG. 13, a construct is provided that furnishes an electrical band-pass capability such that is adapted to pass only pacemaking electrical signals.

FIG. 13A is a depicts a pacemaking signal 530 which has a pulse width duration 532 of about 1 millisecond and a repetition period 534 of about 1 second. It is desired to pass only this signal 530.

For the signal 530, a frequency response curve 536 can be constructed with so that it is adapted to pass signals only in area 538 of curve 536 and to block everything outside of area 538. One may design the desired frequency response curve taking into account the resistance, inductance, and capacitance of the system in accordance with well known electrical filter principles.

Figure 14:
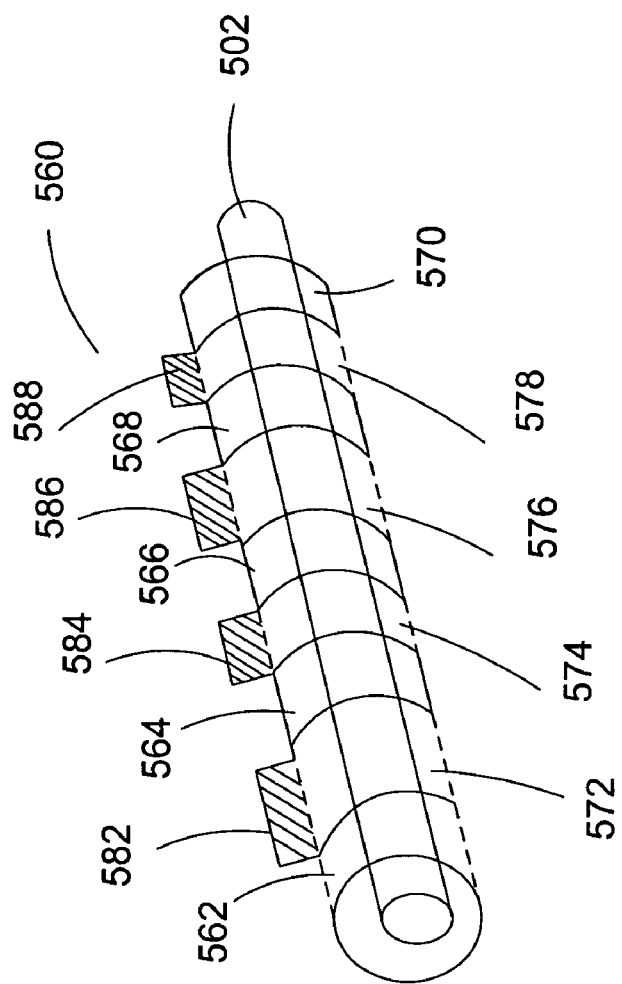
FIG. 14 is a schematic illustration of a lead assembly with a composite coating that provides a desired frequency response curve.

One means of providing the desired frequency response curve 536 is illustrated in FIG. 14. Referring to FIG. 14, it will be seen that assembly 560 is comprised of a conductor 502 and, discontinuously disposed therein, nanomagnetic coatings 562, 564, 566, 568, and 570. The nanomagnetic coatings have the properties described hereinbefore for nanomagnetic films (see FIGS. 6A through 6E).

Disposed in between adjacent nanomagnetic coatings 562/564, 564/566, 566/568, and 568/570 are nanodielectric coatings 572, 574, 576, and 578. These nanodielectric coatings have resistivities of from about of from about $50 \times 10^{-6}$ ohm-meters to about 1,000 ohm-meters; and they preferably have a dielectric constant of from about 1.5 to about 15,000.

One may use any of the nanodielectric materials and/or coatings that are commercially available. These nano-sized dielectric materials generally nave a particle size of less than 100 nanometers. They are available, e.g., from the Nanodielectric Corporation of 18683 Sheldon Road, Middleburg Heights, Ohio 44130, United States of America. Reference also may be had, e.g., to International Patent Publications W003003439A1 and W003003438A1, the entire disclosure of each of which is hereby incorporated by reference into this specification.

In one embodiment, the nanodielectric material is comprised of nano-sized silica. In another embodiment, nano-sized alumina is used. In yet another embodiment, nano-sized aluminum nitride is used.

Referring again to FIG. 14, and in the embodiment depicted therein, it will be apparent that the adjacent layers of nanomagnetic material (such as 562) and dielectric material (such as 572) form an RLC circuit in combination with the conductor 502. The nanomagnetic material contributes to the inductive reactance, the nanodielectric material contributes to the capacitative reactance, and the conductor contributes to the resistance. By the appropriate selection of material properties and sizes, one may combine the desired quantities of inductance, capacitance, and resistance to construct the desired frequency response curve (see FIG. 13B).

Referring again to FIG. 14, and in the embodiment depicted therein, one can selectively coat sections of the dielectric material with conductors 582, 584, 586, and 588 to, as desired, for parallel circuits, series circuits, parallel series circuits, and the like to obtained the desired reactances. Thus, e.g., one may connect the dialectics in parallel so that their capacitances add, or one may connect the inductances in series so that, e.g., their inductances may add. As will be apparent, one may obtain any desired value of capacitance and/or inductance by any desired series, parallel, and/or series circuits or combinations thereof.

In the embodiment depicted in FIG. 14, the connections between dielectric materials and/or inductances have not been shown for the sake of simplicity of representation.

Figure 15:
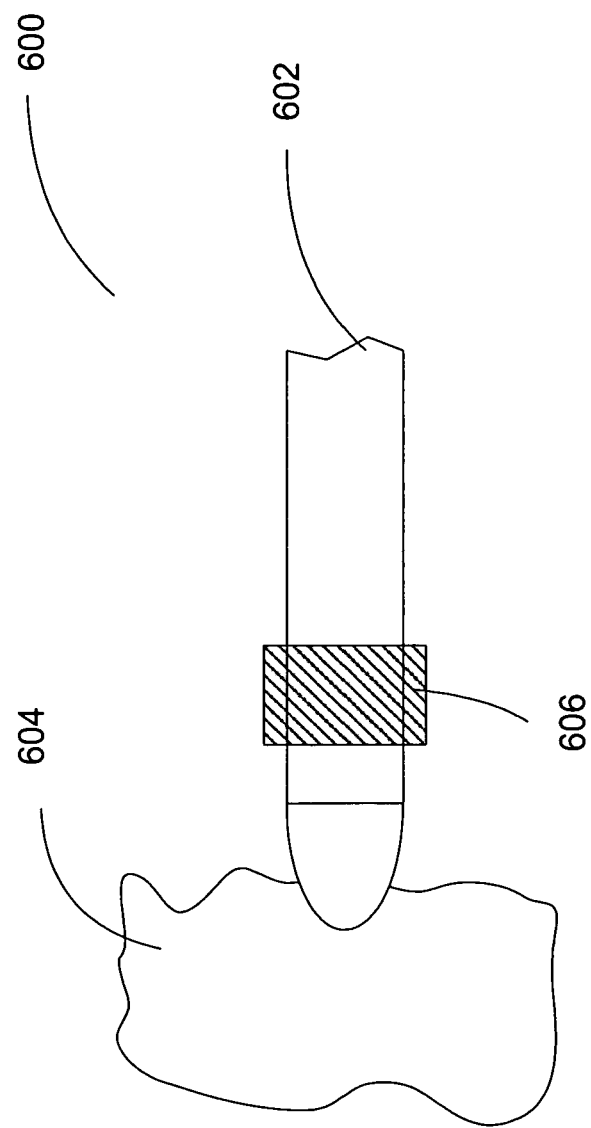
FIG. 15 is a schematic of a lead assembly in contact with cardiac tissue.

FIG. 15 illustrates an assembly 600 comprised of a lead 602 in contact with cardiac tissue 604. In this embodiment, only one section, section 606, of the lead 602 is coated with nanomagnetic material described elsewhere in this specification. In one embodiment, not shown, the section 606 is coated with a combination of nanomagnetic material and nanodielectric material to produce a desired frequency response curve as is discussed elsewhere in this specification.

Figure 16A:
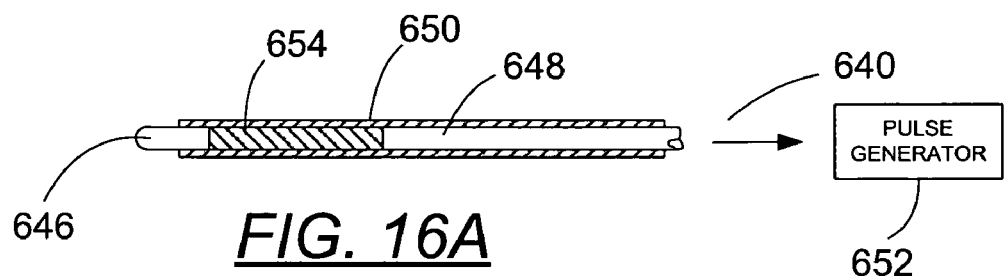
FIGS. 16A, 16B, and 16C are schematic illustrations of lead assemblies that comprise separately coated components.
Figure 16B:
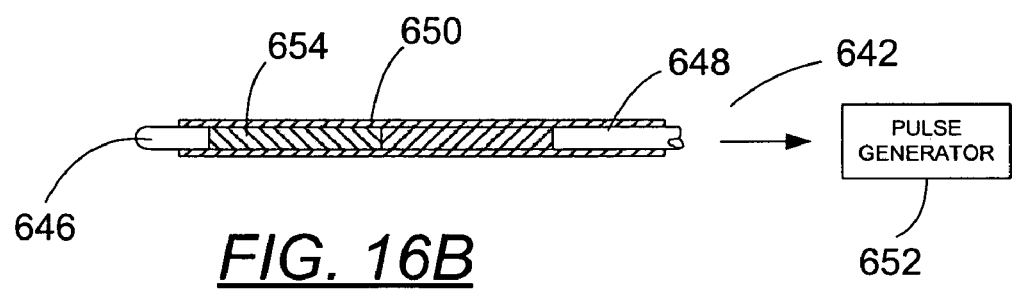
Figure 16C:
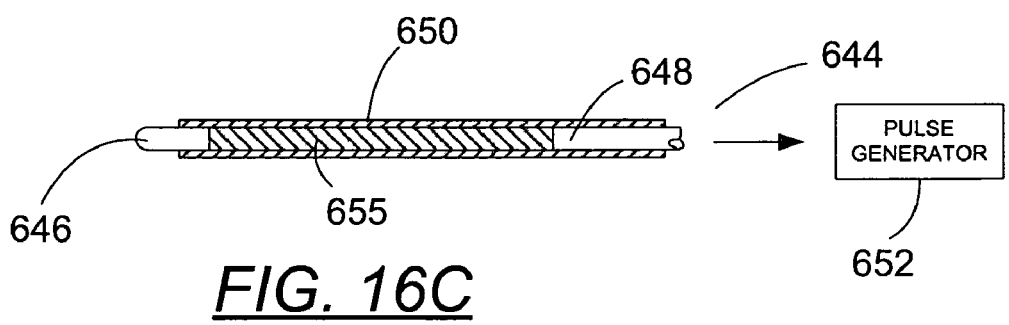

FIGS. 16A, 16B and 16C illustrate leads 640, 642, and 644, each of which is comprised of a serial element (serial with a distal electrode 646 and a conductor 648), and each of which is coated with a coating 650 to increase the inductance reactance (and thus the impedance) between the distal electrode 646 and the pulse generator 652.

In the embodiment illustrated in FIG. 16A, a single coating element 654 is contiguous with the conductor 648, and the entire assembly is coated with coating 650. In the embodiment illustrated in FIG. 16B, coated element 654 is contiguous with a separate coated element 655 which, in turn, is contiguous with conductor 648; and the entire assembly is coated with coating 650. In the Figure depicted in FIG. 16C, a longer coating element 655 is contiguous with conductor 648, and the entire assembly is coated with coating 650.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention.

We claim:

1. An assembly for protecting biological tissue from the effects of heating comprising a conductor in contact with said biological tissue and forming an electrical circuit comprising said biological tissue, wherein said assembly is comprised of means for modifying the impedance of said electrical circuit such that, at a frequency of from about 20 megahertz to about 150 megahertz, said impedance is at least about 0.5 ohms per centimeter of length of said conductor, and wherein said assembly is comprised of means for limiting the flow of current through said tissue such that, when said assembly is exposed to an alternating electromagnetic wave at a frequency of 64 megahertz and a direct current magnetic field strength of 1.5 Tesla for at least about 15 minutes, the temperature of said biological tissue does not exceed 42 degrees Celsius.

2. The assembly as recited in claim 1 wherein, when said assembly is exposed to an alternating electromagnetic wave at a frequency of 64 megahertz and a direct current magnetic field strength of 1.5 Tesla for at least about 15 minutes, the temperature of said biological tissue does not exceed 39 degrees Celsius.

3. The assembly as recited in claim 1, wherein, at a frequency of from about 50 to about 70 megahertz, said impedance is at least about 2 ohms per centimeter of length of said conductor.

4. The assembly as recited in claim 3, wherein said assembly further comprises a means for cooling said biological tissue.

5. The assembly as recited in claim 3, wherein said assembly further comprises a magnetic shield.

6. The assembly as recited in claim 1, wherein said means for limiting current flow through said biological tissue comprises an a radio frequency choke electrically connected to said conductor.

7. An assembly for protecting biological tissue from the effects of heating comprising a conductor in contact with said biological tissue and forming an electrical circuit comprising said biological tissue, wherein said assembly is comprised of means for limiting the flow of current through said tissue such that, when said assembly is exposed to an alternating electromagnetic wave at a frequency of 64 megahertz and a direct current magnetic field strength of from about 1.5 Tesla for at least about 15 minutes, the temperature of said biological tissue does not exceed 39 degrees Celsius, wherein said assembly is a magnetically shielded assembly comprised of a medical device implanted in a biological organism, wherein said medical device is disposed near said biological tissue, and wherein said magnetically shielded assembly is comprised of a magnetic shield disposed on at least a portion of said medical device.

8. The assembly as recited in claim 7, wherein said magnetic shield is comprised of a first layer of nanomagnetic material.

9. The assembly as recited in claim 8, wherein: said first layer of nanomagnetic material has a thickness of at least about 150 nanometers, a mass density of at least about 0.001 grams per cubic centimeter, a saturation magnetization of from about 1 to about 36,000 Gauss, a coercive force of from about 0.01 to about 5,000 Oersteds, and a relative magnetic permeability of from about 1 to about 500,000.

10. The assembly as recited in claim 9, wherein said first layer of nanomagnetic material has a thickness of from about 500 to about 1,000 nanometers.

11. The assembly as recited in claim 9, wherein said magnetic shield is disposed on at least a portion of an implantable medical lead.

12. The assembly as recited in claim 9, wherein said magnetic shield is disposed on at least a portion of a multiple strand conductor.

13. The assembly as recited in claim 9, wherein said first layer of nanomagnetic material is comprised of electrical circuitry.

14. The assembly as recited in claim 9, wherein said medical device is a catheter assembly.

15. The assembly as recited in claim 9, wherein said magnetic shield is comprised of a first layer of nanoelectrical material disposed around said first layer of nanomagnetic material, and wherein said first layer of nanoelectrical material has a thickness of from about 0.5 to about 2 microns and a resistivity of from about 1 to about 100 microohm-centimeters.

16. The assembly as recited in claim 9, wherein said magnetic shield is comprised of a first layer of nanothermal material disposed around said first layer of nanomagnetic material, and wherein said first layer of nanothermal material has a thermal conductivity of at least about 150 watts/meter-degree Kelvin and a resistivity of at least about 1010 microohm-centimeters.

17. The assembly as recited in claim 15, wherein said first layer of nanoelectrical material has a thermal conductivity of from about 1 to about 4 watts/centimeter-degrees Kelvin.

18. The assembly as recited in claim 17, further comprising a second layer of nanomagnetic material disposed around said first layer of nanoelectrical material, wherein said second layer of nanomagnetic material has a mass density of at least about 0.001 grams per cubic centimeter, a saturation magnetization of from about 1 to about 36,000 Gauss, a coercive force of from about 0.01 to about 5,000 Oersteds, and a relative magnetic permeability of from about 1 to about 500,000.

19. The assembly as recited in claim 17, further comprising a layer of nanothermal material disposed around said first layer of nanoelectrical material, wherein said first layer of nanothermal material has a thermal conductivity of at least about 150 watts/meter-degree Kelvin and a resistivity of at least about $10^{10}$ microohm-centimeters.

20. The assembly as recited in claim 18, wherein said assembly further comprises a layer of nanothermal material disposed around said second layer of nanomagnetic material, and wherein said layer of nanothermal material material has a thermal conductivity of at least about 150 watts/meter-degree Kelvin and a resistivity of at least about $10^{10}$ microohm-centimeters.

21. The assembly as recited in claim 9, wherein said magnetic shield further comprises antithrombogenic material.

22. An assembly for protecting biological tissue from the effects of induced voltages produced by high frequency electromagnetic radiation, wherein said assembly comprises a conductor and pulse generator in contact with said biological tissue and forming an electrical induction loop comprising said biological tissue, wherein said assembly is comprised of a magnetic shield disposed between said high frequency electromagnetic radiation and said conductor, and wherein said assembly is comprised of means for limiting the voltage induced in said electrical induction loop such that, when said high frequency electromagnetic radiation contacts said assembly, said induced voltage is less than about 0.5 volts.

23. The assembly as recited in claim 22, wherein said magnetic shield is comprised of nanomagnetic material.

24. The assembly as recited in claim 23, wherein said nanomagnetic material is present in the form of a first layer of nanomagnetic material with a thickness of at least about 150 nanometers.

25. The assembly as recited in claim 24, wherein said first layer of nanomagnetic material has a mass density of at least about 0.001 grams per cubic centimeter, a saturation magnetization of from about 1 to about 36,000 Gauss, a coercive force of from about 0.01 to about 5,000 Oersteds, and a relative magnetic permeability of from about 1 to about 500,000.

26. The assembly as recited in claim 25, wherein said first layer of nanomagnetic material has a thickness of from about 500 to about 1,000 nanometers.

27. The assembly as recited in claim 25, wherein said magnetic shield is disposed on at least a portion of an implantable medical lead.

28. The assembly as recited in claim 25, wherein said wherein said magnetic shield is disposed on at least a portion of a multiple strand conductor.

29. The assembly as recited in claim 25, wherein said magnetic shield is disposed on at least a portion of a multifilar coiled conductor.

30. The assembly as recited in claim 25, wherein said magnetic shield is disposed on at least a portion of a monfilar coiled conductor.

31. The assembly as recited in claim 25, wherein said first layer of nanomagnetic material is comprised of electrical circuitry.

32. The assembly as recited in claim 25, wherein said means for means for limiting the voltage induced in said electrical induction loop is comprised of electrical circuitry.

33. An assembly for protecting biological tissue from the effects of induced voltages produced by high frequency electromagnetic radiation, wherein said assembly comprises a medical device in contact with said biological tissue and forming an electrical induction loop comprising said biological tissue, wherein said assembly is comprised of a magnetic shield disposed between said high frequency electromagnetic radiation and said medical device, and wherein said assembly is comprised of means for limiting the voltage induced in said electrical induction loop such that, when said high frequency electromagnetic radiation contacts said assembly, said induced voltage is less than about 0.5 volts.

34. The assembly as recited in claim 33, wherein said medical device is a cathether assembly.

35. The assembly as recited in claim 33, wherein said medical device is a guidewire.

36. The assembly as recited in claim 33, wherein said medical device is a stylet.

37. The assembly as recited in claim 33, wherein said medical device is a transesophagal medical lead.

38. The assembly as recited in claim 33, wherein a sheath is disposed over said medical device.

39. The assembly as recited in claim 38, wherein said magnetic shield is disposed over said sheath.

40. The assembly as recited in claim 33, wherein said wherein said magnetic shield is comprised of a first layer of nanoelectrical material disposed around said first layer of nanomagnetic material, wherein: said first layer of nanoelectrical material has a thickness of from about 0.5 to about 2 microns and a resistivity of from about 1 to about 100 microohm-centimeters.

41. The assembly as recited in claim 24, wherein said wherein said magnetic shield is comprised of a first layer of nanoelectrical material disposed around said first layer of nanomagnetic material, wherein: said first layer of nanoelectrical material has a thickness of from about 0.5 to about 2 microns and a resistivity of from about 1 to about 100 microohm-centimeters.

42. The magnetically shielded assembly as recited in claim 40, further comprising a second layer of nanomagnetic material disposed around said first layer of nanoelectrical material, wherein said second layer of nanomagnetic material has a mass density of at least about 0.001 grams per cubic centimeter, a saturation magnetization of from about 1 to about 36,000 Gauss, a coercive force of from about 0.01 to about 5,000 Oersteds, and a relative magnetic permeability of from about 1 to about 500,000.

43. The magnetically shielded assembly as recited in claim 41, further comprising a second layer of nanomagnetic material disposed around said first layer of nanoelectrical material, wherein said second layer of nanomagnetic material has a mass density of at least about 0.001 grams per cubic centimeter, a saturation magnetization of from about 1 to about 36,000 Gauss, a coercive force of from about 0.01 to about 5,000 Oersteds, and a relative magnetic permeability of from about 1 to about 500,000.

44. The assembly as recited in claim 24, wherein said magnetic shield further comprises antithrombogenic material.

45. The assembly as recited in claim 33, wherein said magnetic shield further comprises antithrombogenic material.

* * * * *